(12) United States Patent
Sidelman

(10) Patent No.: US 7,741,274 B2
(45) Date of Patent: *Jun. 22, 2010

(54) CASEIN DERIVED PEPTIDES AND USES THEREOF IN THERAPY

(75) Inventor: Zvi Sidelman, Tel Aviv (IL)

(73) Assignee: Peptera Pharmaceuticals Ltd., Tel Aviv (IL)

( * ) Notice: Subject to any disclaimer, the term of this patent is extended or adjusted under 35 U.S.C. 154(b) by 207 days.

This patent is subject to a terminal disclaimer.

(21) Appl. No.: 11/518,400

(22) Filed: Sep. 8, 2006

(65) Prior Publication Data

US 2007/0161557 A1 Jul. 12, 2007

Related U.S. Application Data

(63) Continuation of application No. 09/942,121, filed on Aug. 30, 2001, now abandoned, which is a continuation-in-part of application No. PCT/IL01/00198, filed on Mar. 1, 2001.

(30) Foreign Application Priority Data

Mar. 1, 2000 (IL) ..................................... 134830

(51) Int. Cl.
| | |
|---|---|
| A23C 11/04 | (2006.01) |
| A23J 1/20 | (2006.01) |
| A23J 1/22 | (2006.01) |
| A61K 38/08 | (2006.01) |
| A61K 38/10 | (2006.01) |
| A61K 38/00 | (2006.01) |

(52) U.S. Cl. .......................... 514/2; 514/775; 530/360; 530/361; 530/407; 424/278.1

(58) Field of Classification Search ........................ None
See application file for complete search history.

(56) References Cited

U.S. PATENT DOCUMENTS

| | | | | |
|---|---|---|---|---|
| 3,778,426 A | * | 12/1973 | Najjar et al. ................. | 530/326 |
| 4,636,384 A | * | 1/1987 | Stolle et al. ............... | 424/157.1 |
| 4,959,455 A | * | 9/1990 | Clark et al. ................. | 530/351 |
| 5,700,662 A | * | 12/1997 | Chance et al. ............. | 435/69.4 |
| 5,763,392 A | * | 6/1998 | Hansen et al. ................. | 514/2 |
| 6,358,508 B1 | * | 3/2002 | Ni et al. .................... | 424/139.1 |

OTHER PUBLICATIONS

[Attachment 1] NCBI Sequence Viewer (2007, updated) CAA42516, alpha-S1-casein, http://www.ncbi.nlm.nih.gov/entrez/viewer.fcgi?db=protein&val=92, pp. 1-2.*
[Attachment 2] NCBI Sequence Viewer (2007, updated) CAA55185, alpha-S1-casein, http://www.ncbi.nlm.nih.gov/entrez/viewer.fcgi?db=protein&val=854086, pp. 1-2.*
[Attachment 1] NCBI Sequence Viewer (2007, updated) P09115, alpha-S1-casein precursor, http://www.ncbi.nlm.nih.gov/entrez/viewer.fcgi?db=protein&val=115651, pp. 1-2.*
Hematopoiesis (2007, updated) "Hematopoiesis", http://www.som.tulane.edu/classware/pathology/Krause/Blood/HP.html, p. 1.*
Thrombopoiesis (2007, updated) "Thrombopoiesis", http://www.tau.ac.il/~inter05/throm.htm, p. 1.*
Chabance et al., "Casein peptide release and passage to be blood in humans during digestion of milk or yogurt", *Biochimie*, 80:155-165 (1998).
McSweeney et al., "Proteolytic specificity of chymosin on bovine alpha S1-casein", *J. Dairy Res.*, 60(3):401-412 (1993).

* cited by examiner

*Primary Examiner*—Maryam Monshipouri
*Assistant Examiner*—Samuel W Liu
(74) *Attorney, Agent, or Firm*—D. Graeser Ltd.

(57) ABSTRACT

Biologically active peptides that are derived from or are similar to sequences identical with the N-terminus of the αS1 fraction of milk casein. These peptides are capable of stimulating and enhancing immune response, protecting against viral infection, normalizing serum cholesterol levels, and stimulating hematopoiesis. The casein-derived peptides are non-toxic and can be used to treat and prevent immune pathologies, hypercholesterolemia, hematological disorders and viral-related diseases.

56 Claims, 21 Drawing Sheets

Effect of Peptides Derived from Natural Casein on Human Natural Killer (NK) Cell Activity in Cells from a Single Donor

| Dose> | 0 | 5 | 10 | 25 | 50 | 100 | 250 | 500 |
|---|---|---|---|---|---|---|---|---|
| 1:50 | 3.9 | 5.4 | 11.3 | 10.9 | 9.1 | 8.3 | 12.5 | 15.5 |
| 1:100 | 4.6 | 5.1 | 12.4 | 12.8 | 11.9 | 10.8 | 12.1 | 14.9 |

Selective Stimulation of Human Natural Killer (NK) Cell Activity by Peptides Derived from Natural Casein

| Patient | Type | 0 | 10 | 25 | 100 | 250 | 500 |
|---|---|---|---|---|---|---|---|
| 1 | Normal | 13 | 15 | 15 | 12 | 13 | 15 |
| 2 | NHL | 10.1 | 13.8 | 14.3 | - | 15.8 | 13.7 |
| 3 | NHL | 3.5 | 10.4 | 8.4 | 10.8 | - | - |
| 4 | Br. Ca. | 4.2 | 2.7 | 7.1 | 7.7 | 5.9 | 10.1 |
| 5 | - | | 12.2 | 18.1 | 19.1 | 14.3 | 13.4 | 15.8 |
| 6 | - | | 17 | 15 | 15 | 15 | 13 | 9 |

Peptides Derived from Natural Casein Stimulate
Proliferation of Human $CD_{56}$ Surface Antigen Positive (NK) Cells

| Patient | Control | Chay-13 |
|---------|---------|---------|
| 1 | 0.60 | 0.20 |
| 2 | 0.60 | 1.90 |
| 3 | 0.10 | 0.90 |
| 4 | 0.40 | 3.30 |
| 5 | 1.50 | 3.70 |
| Mean | 0.64 | 2.00 |
| SD | 0.52 | 1.50 |

Peptides Derived from Natural Casein Stimulate
Proliferation of Human CD$_3$ Surface Antigen Positive (T) Cells

| Patient | Control | Chay-13 |
|---------|---------|---------|
| 1 | 7.90 | 10.40 |
| 2 | 8.19 | 10.46 |
| 3 | 12.82 | 58.64 |
| 4 | 62.86 | 50.44 |
| 5 | 5.49 | 47.76 |
| Mean | 19.45 | 35.54 |
| SD | 24.41 | 23.27 |

Peptides Derived from Natural Casein Stimulate
Proliferation of Human $CD_{56}$ and $CD_3$ Surface Antigen Positive
(NK/T) Cells

| Patient | Control | Chay-13 |
|---|---|---|
| 1 | 8.00 | 25.00 |
| 2 | 1.1 | 4.3 |
| 3 | 0.1 | 0.85 |
| 4 | 2.77 | 3.89 |
| 5 | 1.74 | 4.34 |
| 6 | 0.84 | 4.53 |
| 7 | 0 | 2.55 |
| Mean | 2.08 | 6.49 |
| SD | 2.78 | 8.27 |

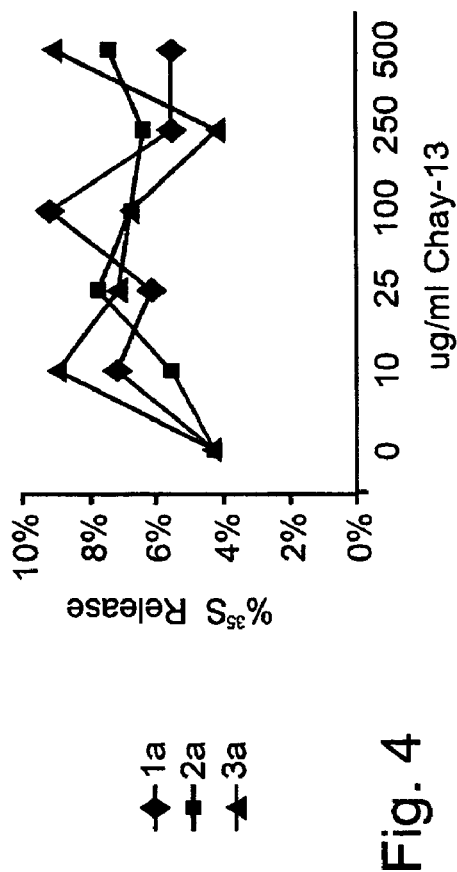
Fig. 4 — The Effect of Synthetic Peptides on the Stimulation of NK Cells Activity in Cultured Human PBC
| PEPTIDE | 0 | 10 | 25 | 100 | 250 | 500 | µg/ml |
|---|---|---|---|---|---|---|---|
| 1a | 4.3% | 1880 7.3% | 1803 6.2% | 2006 9.2% | 1761 5.6% | 1768 5.6% | 1a |
| 2a | 4.3% | 1762 5.6% | 1908 7.7% | 1840 6.7% | 1805 6.2% | 1883 7.4% | 2a |
| 3a | 4.3% | 2003 9.1% | 1868 7.1% | 1847 6.8% | 1671 4.2% | 1997 9.1% | 3a |

Peptides Derived from Natural Casein Stimulate Proliferation of Cultured Human Peripheral Blood Stem Cells

| Blood origin | Incubation period (days) | Control | 50 (µg/ml) | 100 (µg/ml) | 300 (µg/ml) | 600 (µg/ml) |
|---|---|---|---|---|---|---|
| PBSC | 20 | 1663 | 3007 | 1800 | 4306 | 3310 |
| PBSC | 15 | 741 | 1612 | 784 | - | 920 |
| BM normal | 21 | 675 | - | 660 | 834 | 817 |
| BM Auto | 21 | 945 | - | 916 | 1537 | 1284 |
| BM 1 | 21 | 1829 | 4217 | 4396 | 9178 | 1446 |
| BM 2 | 21 | 1829 | 5039 | 2939 | 1496 | - |
| CB1 | 14 | 1159 | 1191 | 1694 | 3961 | 3297 |
| CB2 | 14 | 3434 | - | 10882 | - | 13560 |

Peptides Derived from Natural Casein Stimulate Proliferation of Normal Human Hematopoietic Cells

| Donor | Days Of Incubation | Factors Added | Relative Cell No. X 10⁴/ml µg Chay-13/ml | | | | |
|---|---|---|---|---|---|---|---|
| | | | 0 | 25 | 100 | 250 | 500 |
| Bone Marrow | 14 | EPO, hIL-3, hSCF, AB serum | 41 | 64 | - | 67 | 51 |
| Cord Blood | 13 | EPO, hIL-3, hSCF, AB serum | 27 | 158 | 66 | 50 | - |

Fig. 6

Synthetic Casein-Derived Peptides
Effect of Peptide Length on Relative Cell Distribution (Differential Count) (%)

| Identification | PEPTIDE'S LENGTH | CONC. (μg) | Mcb | PMN | EARLY MK | LATE MK | TOTAL MK | EARLY RBC | LATE RBC | TOTAL RBC | PLASMA CELLS | DENDRITIC CELLS | EOS BAS | MITOSES | TOTAL |
|---|---|---|---|---|---|---|---|---|---|---|---|---|---|---|---|
| 74 | 2 | 25 | 17.8 | 2.6 | 3.5 | 3.7 | 7.2 | 15.8 | 20.4 | 36.2 | 8.3 | 23.0 | 2.8 | 4 | 544 |
| 1P | 3 | 25 | 11.3 | 2.9 | 8.8 | 5.4 | 14.2 | 16.5 | 38.6 | 55.1 | 6.7 | 7.5 | 2.3 | 9 | 521 |
| 2P | 4 | 25 | 6.1 | 2.3 | 7.4 | 9.1 | 16.5 | 19.4 | 51.8 | 71.2 | - | - | 0.6 | 4 | 700 |
| 3P | 5 | 25 | 12.9 | 1.8 | 16.0 | 16.9 | 32.9 | 18.9 | 23.4 | 42.3 | 2.2 | 7.4 | 0.5 | 2 | 551 |
| 4P | 6 | 25 | 22.0 | 3.1 | 21.6 | 24.6 | 46.2 | 5.7 | 11.5 | 17.2 | 0.1 | 4.5 | 4.6 | 4 | 842 |
| 5P | 7 | 25 | 30.1 | 9.0 | 7.8 | 7.5 | 15.3 | 12.9 | 12.8 | 25.7 | 2.4 | 14.0 | 3.5 | 5 | 744 |
| X | 9 | 25 | 30.0 | 6.6 | 5.6 | 3.0 | 8.6 | 16.4 | 18.5 | 34.9 | 0.5 | 15.2 | 4.3 | 2 | 762 |
| 2a | 11 | 25 | 8.6 | 1.6 | 14.2 | 28.9 | 43.1 | 13.5 | 26.5 | 40.0 | 3.0 | 3.0 | 0.6 | 12 | 931 |
| 2a | 11 | 250 | 8.4 | 0.9 | 19.4 | 19.8 | 39.2 | 12.6 | 35.0 | 47.6 | 2.2 | 0.5 | 1.2 | 11 | 651 |
| 3a | 12 | 25 | 9.5 | 1.8 | 24.1 | 22.5 | 46.6 | 14.0 | 23.4 | 37.4 | - | 3.7 | 1.0 | 16 | 779 |
| D | 16 | 25 | 41.0 | 4.5 | 7.0 | 7.6 | 14.6 | 9.6 | 20.2 | 29.8 | 3.4 | - | 6.8 | 7 | 471 |

Control (without synthetic peptides)

Fig. 7

| Identification | PEPTIDE'S LENGTH | CONC. (μg) | Mcb | PMN | EARLY MK | LATE MK | TOTAL MK | EARLY RBC | LATE RBC | TOTAL RBC | PLASMA CELLS | DENDRITIC CELLS | EOS BAS | MITOSES | TOTAL |
|---|---|---|---|---|---|---|---|---|---|---|---|---|---|---|---|
| D | 16 | 250 | 26.6 | 4.8 | 11.9 | 19.4 | 31.3 | 4.2 | 13.1 | 17.3 | 12.3 | 2.4 | 4.5 | 6 | 620 |
| E | 17 | 100 | 15.4 | 5.1 | 12.9 | 14.5 | 27.4 | 20.5 | 23.6 | 44.1 | 4.5 | 1.4 | 2.2 | 7 | 552 |
| E | 17 | 1250 | 7.0 | 2.1 | 12.7 | 19.2 | 31.9 | 15.2 | 36.2 | 51.4 | 3.2 | 0.7 | 3.8 | 11 | 759 |
| F | 18 | 25 | 17.8 | 4.8 | 14.5 | 19.3 | 33.8 | 8.6 | 24.3 | 32.9 | 7.2 | - | 3.4 | 9 | 580 |
| F | 18 | 250 | 9.9 | 6.1 | 18.3 | 19.5 | 37.8 | 15.0 | 27.9 | 42.9 | 2.2 | 0.5 | 0.6 | 13 | 791 |
| G | 19 | 25 | 19.9 | 9.7 | 14.4 | 17.0 | 31.4 | 8.8 | 15.3 | 24.1 | 9.7 | - | 5.2 | 5 | 659 |
| H | 20 | 25 | 12.8 | 3.3 | 17.0 | 31.2 | 48.2 | 15.4 | 17.6 | 33.0 | 1.8 | 0.6 | 0.4 | 11 | 826 |
| I | 21 | 25 | 19.2 | 9.0 | 11.9 | 30.0 | 41.9 | 7.9 | 20.9 | 28.8 | 1.4 | - | . | 8 | 708 |
| J | 22 | 25 | 15.0 | 4.5 | 13.2 | 14.0 | 27.2 | 18.9 | 28.4 | 47.3 | 4.0 | 0.2 | 1.8 | 15 | 952 |
| K | 23 | 25 | 28.6 | 14.9 | 3.9 | 6.5 | 10.4 | 3.2 | - | 3.2 | 6.5 | 14.3 | 22.1 | 1 | 154 |
| L | 24 | 25 | 10.4 | 3.6 | 18.9 | 36.8 | 55.7 | 10.3 | 12.2 | 22.5 | 4.6 | 2.2 | 0.9 | 14 | 768 |
| N | 26 | 100 | 13.8 | 3.6 | 13.6 | 16.4 | 30.0 | 12.4 | 14.2 | 26.6 | 1.5 | 19.8 | 4.6 | 14 | 675 |
| control (without synthetic peptides) | | | 17.4 | 1.6 | 12.4 | 10.6 | 23.0 | 13.1 | 44.0 | 57.1 | 0.3 | 0.1 | 0.2 | 10 | 686 |

Fig. 7 (Continued)

Peptides Derived from Natural Casein Stimulate Leukocyte Proliferation in Irradiated, Bone Marrow Reconstituted Balb Mice.

| Days After Treatment | 2 Control | 2 Chay-13 | 4 Control | 4 Chay-13 | 6 Control | 6 Chay-13 | 9 Control | 9 Chay-13 | 12 Control | 12 Chay-13 | 15 Control | 15 Chay-13 |
|---|---|---|---|---|---|---|---|---|---|---|---|---|
| 1 | 6 | 9 | 6 | 32 | 55 | 55 | 90 | 205 | 100 | 280 | 500 | 800 |
| 2 | 10 | 10 | 18 | 34 | 40 | 45 | 135 | 100 | 160 | 280 | 440 | 540 |
| 3 | 4 | 6 | 14 | 40 | 20 | 85 | 100 | 130 | 140 | 220 | 380 | 800 |
| 4 | 6 | 6 | 8 | 14 | 35 | 58 | 130 | 125 | 280 | 440 | 600 | 640 |
| 5 | 12 | 6 | 16 | 18 | 75 | 60 | 70 | 155 | 40 | 340 | 520 | 600 |
| 6 | 8 | 10 | 18 | 90 | 25 | 45 | 85 | 90 | 320 | 160 | 380 | 640 |
| Mean | 7.67 | 7.83 | 13.33 | 38* | 41.67 | 58* | 101.67 | 134.17 | 173.33 | 286.67 | 470 | 670 |
| SD | 2.69 | 1.86 | 4.71 | 24.95 | 18.63 | 13.42 | 23.57 | 38.01 | 97.75 | 88.44 | 78.95 | 97.81 |

* $p < 0.008$

Peptides Derived from Natural Casein Stimulate Thrombocyte Proliferation in Irradiated, Bone Marrow Reconstituted CBA Mice.

| Days After Treatment | 11 Control | 11 Chay-13 | 13 Control | 13 Chay-13 | 15 Control | 15 Chay-13 |
|---|---|---|---|---|---|---|
| 1 | 43 | 50 | 75 | 103 | 98 | 110 |
| 2 | 48 | 54 | 71 | 105 | 99 | 128 |
| 3 | 68 | 68 | 80 | 110 | 102 | 111 |
| 4 | 64 | 64 | 104 | 104 | 96 | 103 |
| 5 | 67 | 67 | 91 | 101 | 104 | 133 |
| 6 | 63 | 54 | 90 | 90 | 97 | 114 |
| 7 | 54 | 45 | 104 | 107 | 87 | 104 |
| 8 | | 63 | | 104 | | 116 |
| 9 | | 61 | | 93 | | 115 |
| 10 | | 57 | | 116 | | 112 |
| Mean | 58.14 | 58.3 | 87.86 | 103.3* | 97.57 | 114.6** |

* $p<0.01$    ** $p<0.0001$

Stimulation of Sup-T₁ Lymphocyte Cell Proliferation by Peptides Derived from Natural Casein

| Chay 13 µg/ml | 3 days | | 7 days | |
|---|---|---|---|---|
| | cpm Counts | Proliferation Index | cpm Counts | Proliferation Index |
| 50 | 9268 | 1.18 | 120954 | 1.10 |
| 100 | 9940 | 1.26 | 112436 | 1.02 |
| 300 | 8425 | 1.07 | 102957 | 0.93 |
| 600 | 9771 | 1.24 | 101987 | 0.93 |
| 1000 | 8390 | 1.06 | 86649 | 0.79 |
| Control | 7862 | | 109560 | |

| Chay 13 µg/ml | 10 days | | 14 days | |
|---|---|---|---|---|
| | cpm Counts | Proliferation Index | cpm Counts | Proliferation Index |
| 50 | 17695 | 1.03 | 22272 | 1.36 |
| 100 | 19168 | 1.12 | 22842 | 1.40 |
| 300 | 21806 | 1.28 | 15318 | 0.93 |
| 600 | 22826 | 1.34 | 17368 | 1.06 |
| 1000 | 21764 | 1.28 | 10034 | 0.61 |
| Control | 17046 | | 16313 | |

Fig. 11

Peptides Derived from Natural Casein Inhibit of HIV-1 Infection of CEM Cells: Cell Proliferation vs. $P^{24}$ Antigen Levels

|  | Chay 13 µg/ml | CEM cells ||
| --- | --- | --- | --- |
|  |  | Cell No. (x$10^6$) 15 days | $P^{24}$Ag ng/ml |
| 3H | 50 | 0.29 | 16.39 |
|  | 100 | 0.55 | 7.73 |
|  | 300 | 0.54 | 1.61 |
|  | 600 | 0.75 | 0.18 |
|  | 1000 | 0.57 | 0.19 |
| 24H | 50 | 0.40 | 0.24 |
|  | 100 | 0.48 | 4.21 |
|  | 300 | 0.56 | 2.94 |
|  | 600 | 0.62 | 0.18 |
|  | 1000 | 0.79 | 4.03 |
| 48H | 50 | 0.37 | 10.05 |
|  | 100 | 0.50 | 9.16 |
|  | 300 | 0.56 | 3.21 |
|  | 600 | 0.70 | 16.49 |
|  | 1000 | 0.84 | 2.16 |
| Control | IF | 0.35 | 11.42 |
|  | UIF | 0.42 | 0.17 |

Fig. 12

Synthetic Casein-Derived Peptides Inhibit HIV-1 Infection of CEM Cells: Cell Proliferation vs. $P^{24}$ Antigen Levels

| Peptide (3 hr. pretreatment) | Conc. μg/ml | CEM cells | |
|---|---|---|---|
| | | Cell No (x10$^6$) 7 days | $P^{24}$Ag ng/ml |
| 1P (SEQ ID No. 3) | 100 | 1.29 | 0.17 |
| | 500 | 2.01 | 0.14 |
| 3P (SEQ ID No. 5) | 10 | 1.17 | 0.26 |
| | 25 | 1.26 | 0.18 |
| 4P (SEQ ID No. 6) | 25 | 1.26 | 0.42 |
| | 100 | 1.00 | 0.14 |
| | 250 | 1.59 | 0.10 |
| Control | IF | 1.06 | 0.52 |
| | UIF | 0.42 | 0.17 |

Fig. 13

Total Cholesterol (TC), LDL & HDL levels in
Hypercholesterolemic/Hyperlipidemic C57 Bl/6J

| Sample* | Group** | Food | TC | HDL | | LDL |
|---|---|---|---|---|---|---|
| 1 | Normal | Normal | 91 | 44 | 48 | <1 |
| 2 | | Normal | 92 | 51 | 56 | <1 |
| 3 | Control | Enriched | 375 | 53 | 58 | 305 |
| 4 | | Enriched | 411 | 46 | 51 | 348 |
| 5 | B | Enriched | 442 | 47 | 52 | 372 |
| 6 | | Enriched | 445 | 38 | 42 | 386 |
| 7 | C | Enriched | 409 | 47 | 52 | 341 |
| 8 | | Enriched | 411 | 34 | 37 | 361 |
| 9 | 2a | Enriched | 279 | 33 | 36 | 229 |
| 10 | | Enriched | 278 | 43 | 47 | 213 |
| 11 | 3P | Enriched | 312 | 38 | 42 | 251 |
| 12 | | Enriched | 305 | 39 | 43 | 243 |

\* One Blood Sample Represents Blood Drawn from 2 Mice.
\** Each Group Included 4 Mice.

MEAN VALUES

| | | TC | HDL | LDL |
|---|---|---|---|---|
| 1+2 | Normal | 91.5 | 49.75 | <1 |
| 3+4 | Control | 393 | 52 | 326.5 |
| 5+6 | B | 443.5 | 44.75 | 379 |
| 7+8 | C | 410 | 42.5 | 351 |
| 9+10 | 2a | 278.5 | 40 | 221 |
| 11+12 | 3P | 308.5 | 40.5 | 247 |

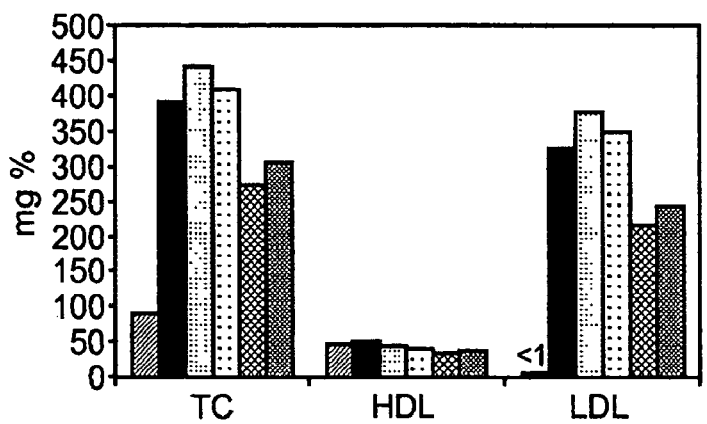

Fig. 15

Cholesterol, HDL & LDL in C57 Bl/6J Treated with Peptides

Effects of Peptides Derived from Natural Casein on Cancer Patients Hematopoiesis

| Patient | WBC before | WBC after | PLT before | PLT after | RBC before | RBC after | HGB before | HGB after |
|---|---|---|---|---|---|---|---|---|
| 1 | 1,200 n | 4,100 n+241% | 17,000 n | 224,000 n+1217% | 3.27 n | 4.05 n+23% | 10.4 n | 12.6 n+21% |
| 2 | 5,400 n | 6,300 n+16.6% | 204,000 n | 259,000 n+26.9% | 3.37 n | 3.46 n+2.6% | 10.8 n | 11.0 n+1.8% |
| 3 | 3,400 n | 5,100 n+50% | 12,700 n | 17,900 n+40% | 4.49 n | 4.71 n+8.4% | 12.9 n | 13.2 n+2.3% |
| 4 | 4,900 n | 6,400 n+30% | | | | | | |
| 5 | 700 n | 4,600 n+557% | 47,000 n | 151,000 n+221% | 2.88 n | 3.45 n+19.7% | 8.6 n | 10.5 n+22% |

Fig. 16

WBC = White blood cells
PLT = Platelets
RBC = Red blood cells
HGB = Hemoglobin

Peptides Derived from Native Casein Stimulate
Thrombocytopoiesis in Acute Myeloid Leukemia (Patient M-1)

| X | Y |
|---|---|
| 0 | 11 |
| 1 | 10 |
| 3 | 10 |
| 5 | 32.5 |
| 7 | 15 |
| 8 | 27.5 |
| 12 | 40 |
| 14.25 | 28 |
| 17 | 35 |
| 21 | 45 |
| 26.35 | 70.3 |
| 31.7 | 74 |
| 40 | 100.7 |

| X | Y |
|---|---|
| 0 | 23 |
| 1 | 18.5 |
| 2 | 25 |
| 3 | 16 |
| 4 | 20.8 |
| 6 | 20.8 |
| 7 | 20 |
| 8 | 23.5 |
| 9 | 26 |
| 10 | 19.5 |
| 11 | 23 |
| 13 | 18.5 |
| 14 | 18.5 |
| 15 | 20 |
| 17.2 | 22 |
| 20.3 | 30 |
| 24 | 44 |
| 29 | 75.6 |
| 36.5 | 86.4 |
| 41 | 139.5 |

Peptides Derived from Native Casein Stimulate Thrombocytopoiesis in Acute Myeloid Leukemia (Patient M-2)

CASEIN DERIVED PEPTIDES AND USES THEREOF IN THERAPY

This is a continuation of U.S. Ser. No. 09/942,121, filed Aug. 30, 2001 now abandoned, which is a continuation-in-part of PCT/IL01/00198, filed Mar. 1, 2001, which claims the benefit of priority from IL 134830, filed 1 Mar. 2000.

FIELD OF THE INVENTION

The present invention relates to biologically active peptides that are derived from or are similar to sequences identical with the N-terminus of the oS1 fraction of milk casein. These peptides are capable of stimulating and enhancing immune response, protecting against viral infection, normalizing serum cholesterol levels, and stimulating hematopoiesis. The casein-derived peptides are non-toxic and can be used to treat and prevent immune pathologies, hypercholesterolemia, hematological disorders and viral-related diseases.

BACKGROUND OF THE INVENTION

Bioactive Molecules from Nutrients:

In addition to the nutritional value of many foods, certain fractions and products of digestive pathways possess the ability to influence physiological processes. Some of these "extranutritional" constituents are present in their active form in the whole nutriment, such as the immunoglobulins in mother's milk and colostrums, phytoestrogens found in soy-based foods, polyphenolic antioxidants from fruits and vitamins. Others are encrypted within nutrient molecules, and are released in an active form during digestion or food processing, for example antihypertensive peptides from lactoglobin [Kitts, D. D. (1999), Can. J. Physiol. Pharmacol. 72:4; 423-434].

Biological Activity in Milk Proteins:

Casein, the predominant milk protein, has been traditionally defined as composed of three fractions, o, β and γ, according to their electrophoretic mobility [N. J. Hipp, et al. (1952), Dairy Sci., 35:272]. Today casein is defined according to the amino acid sequences of each of the subgroups oS1, oS2, β and κ [W. N. Engel et al. (1984), J. Dairy Sci. 67: 1599].

In the course of digestion, the casein proteins are subjected to proteolytic cleavage by acid proteases such as chymosin (rennin), trypsin and pepsin, producing shorter peptides and causing curdling and calcium sequestration by the resultant protein fragments. A few studies with milk compounds demonstrated casein-related bacteriocidal activity. U.S. Pat. No. 3,764,670 discloses proteolytic casein digests possessing antibiotic properties against microorganisms. Israel Patent No. 42863 describes a casein-derived peptide consisting of 23 amino acids of the N-terminus of casein, possessing antibacterial activity. In addition, other physiologically active properties, such as opioid and growth factor-like activities have been proposed for casein or its derivatives [Kitts, D. D., (1999), ibid.].

Immune modulating activity has also been observed in casein peptides. Coste et al. (1992, Immun. Lett. 33: 41-46) observed enhancement of rat lymphocyte proliferation following treatment with a peptide derived from the C-terminus of β casein. However, none of these studies have determined the specific sequences in these casein peptides which confer their "extranutritional" properties.

Hematopoiesis in Cancer Therapy:

Following high-dose chemotherapy, especially following myeloablative doses of chemoradiotherapy supported by autologous bone marrow or peripheral blood stem cell transplantation (ASCT) or allogeneic bone marrow transplantation (BMT), patients are at high risk due to pancytopenia. Granulocytopenia may lead to development of serious, occasionally fatal infectious complications from common bacterial, viral, fungal and parasitic agents in the immediate post transplant period. Similarly, thrombocytopenia frequently results in bleeding tendency and occasionally, in long lasting platelet dependence. Whenever resistance to platelets develops, bleeding episodes can be life threatening and hemorrhagic complications are frequently lethal. The risk due to granulocytopenia can be partially overcome by supportive measures and most effectively by administration of recombinant human cytokines that can enhance reconstitution of granulocytes, particularly granulocyte colony stimulation factor (G-CSF) and granulocyte macrophage colony stimulating factor (GM-CSF). These agents are extremely expensive (approximately $200-400/day/patient) and infrequently cause side effects due to hypersensitivity reactions, fever, bone pain and occasionally vascular leak syndromes, including pericarditis and pleuritis. Some of the side effects may be due to other cytokines that may be intrinsically released by these hematopoietic growth factors. Moreover, the use of these hematopoietic growth factors may be prohibitive in patients with tumor cells bearing G-CSF or GM-CSF receptors such as in acute and chronic myeloid leukemias and in myelodysplastic syndromes. Whereas major progress in treating patients at risk of pancytopenia has been achieved from the use of hematopoietic cytokines, no progress has been made in the treatment of thrombocytopenia. Following high dose chemotherapy and especially following ASCT, patients are at risk for thrombocytopenia which may last for many months even up to 3 years and some thromboctyopenic patients may never recover. Many patients previously treated with multiple blood products become platelet resistant and hence thrombocytopenia may be impossible to overcome, even transiently, despite intensive and frequent platelet transfusions from a single donor. Resistance to platelets and protracted thrombocytopenia represent a common cause of death at ASCT centers worldwide.

Currently, several new recombinant cytokines such as recombinant human interleukin-3 (rhIL3) and recombinant human interleukin-6 (rhIL6) are being investigated as potential agents for enhancing megakaryocytopoiesis and platelet reconstitution. Unfortunately, preliminary clinical trials showed that although rhIL3 and rhIL6 may enhance platelet reconstitution, such effects are by no means dramatic and may take considerable time.

Clearly, protracted thrombocytopenia represents a major problem in clinical Bone Marrow Transplant centers today, for which no satisfactory solution has yet been found.

There is thus a widely recognized need for, and it would be highly advantageous to have a safe, inexpensive, rapidly effective and well-defined stimulator of hematopoiesis, and specifically megakaryocytopoiesis, devoid of the above limitations.

Thrombopoetin (TPO) in Regulation of Hematopoiesis and Platelet Function:

TPO appears to be the major regulator of platelet production in vivo, although increase in the kidney- and liver-derived growth factor in platelet deficiencies is not caused by adaptation of TPO biosynthesis in these organs. Rather, a "feedback loop" seems to exist in which the number of circulating platelets determines how much of the circulating TPO is available to the bone marrow for platelet production. In addition, it has been demonstrated that TPO is an early acting cytokine with important multilineage effects: TPO alone, or in combination with other early acting cytokines, can (i)

promote viability and suppress apoptosis in progenitor cells; (ii) regulate hematopoietic stem cell production and function; (iii) trigger cell division of dormant multipotent cells; (iv) induce multilineage differentiation and (v) enhance formation of multilineage colonies containing granulocytes, erythrocytes, macrophages, and megakaryocytes (MK, CFU-GEMM). Moreover, TPO stimulates the production of more limited progenitors for granulocyte/monocyte, megakaryocyte and erythroid colonies, and stimulates adhesion of primitive human bone marrow and megakaryocytic cells to fibronectin and fibrinogen. Thus, TPO is an important cytokine for clinical hematologists/transplanters: for the mobilization, amplification and ex vivo expansion of stem cells and committed precursor cells for autologous and allogeneic transplantation (von dem Borne, A. E. G. Kr., et al., (1998) Thrombopoietin: it's role in platelet disorders and as a new drug in clinical medicine. In Bailliers Clin. Hematol. June:11 (2), 427-45.

In addition to TPO effects in hematopoiesis, this potent growth factor primes platelets for various agonists and modulates platelet-extracellular matrix interactions. Although it does not itself cause platelet aggregation, TPO upregulates ADP-induced aggregation, especially on the second wave of aggregation, upregulates granule (ADP, ATP, serotonin, etc.) release and production of thromboxane B2, increases platelet attachment to collagen and potentiates shear-induced platelet aggregation. TPO also stimulates PMN activation, inducing IL-8 release and priming oxygen metabolite production, likely enhancing antimicrobial defense.

Clinical studies suggest TPO's value in understanding and treating a variety of hematological conditions. In patients with idiopathic aplastic anemia (AA), elevated TPO levels persist even in remission following immunosuppressive therapy, indicating a hematopoietic defect. TPO is elevated in other forms of aplastic thrombocytopenia as well, but not in conditions of increased platelet destruction. Apparently, the reactive increase in TPO production is insufficient in cases of destructive thrombocytopenia. Thus, TPO is not only a therapeutic option for aplastic, but also for destructive thrombocytopenia.

Thrombopoietic agents are of great clinical interest, for prevention and/or treatment of pathological or treatment-induced thrombocytopenia, and as a substitute for platelet transfusions. Of the cytokines evaluated, all but the marginally potent IL-11 have been deemed unacceptable for clinical use. TPO is widely believed to become the cytokine of choice for throbocytopenia treatment. Recombinant human TPO (Genentech) has recently become available, enabling accurate pharmacokinetic determinations and clinical trials. Thus, TPO's potential applications encompass the realms of supportive care (post chemo/radio-therapy, bone marrow and stem cell transplantation), hematological disease (AA, myelodysplasia, congenital and acquired thrombocytopenia), liver diseases, transfusion (expansion, harvest, mobilization and storage of platelets) and surgery (including liver transplantation). Of particular interest is the potential use of TPO/EPO/G-CSF cocktail for myelodysplasia, G-CSF and TPO combination for peripheral stem cell mobilization and TPO in harvesting CD 34+ cells and ex vivo expansion of megakaryocytes for superior platelet reconstitution. However, similar to other hematopoietic agents under consideration for clinical application, TPO is costly and potentially antigenic at therapeutically effective levels. Thus, it would be advantageous to have a safe, inexpensive and readily available stimulator of thrombopoiesis capable of augmenting TPO activity.

The oS1 Fraction of Casein:

The oS1 fraction of casein can be obtained from milk proteins by various methods [D. G. Schmidth and T. A. J. Paynes (1963), Biochim., Biophys. Acta, 78:492; M. P. Thompson and C. A. Kiddy (1964), J. Dairy Sci., 47:626; J. C. Mercier, et al. (1968), Bull. Soc. Chim. Biol. 50:521], and the complete amino acid sequence of the oS1 fraction of casein was determined by J. C. Mercier et al. (1971) (Eur. J. Biochem. 23:41). The genomic and coding sequences of bovine oS1 fraction of casein have also been cloned and sequenced employing recombinant DNA techniques [D. Koczan, et al. (1991), Nucl. Acids Res. 19(20): 5591; McKnight, R. A., et al. (1989), J. Dairy Sci. 72:2464-73]. Proteolytic cleavage and identification of N-terminal fragments from the oS1 fraction of casein has been documented [J. C. Mercier, et al. (1970), Eur. J. Biochem. 16:439; P. L. H. McSweeney et al. (1993), J. Dairy Res., 60:401], as has the intestinal absorption and appearance of this fragment in mammalian plasma following ingestion of whole milk proteins [Fiat, A. M., et al. (1998) Biochimie, 80(2):2155-65]. Meisel, H. and Bockelmann, W. [(1999), Antonie Van Leeuwenhoek, 76:207-15] detected amino acid sequences of immunopeptides, casokinins and casomorphins in peptides liberated by lactic acid bacteria digests of o and β casein fractions. Of particular interest is the anti-aggregating and thrombolytic activity demonstrated for C-terminal portions of the o- and κ-casein fractions [Chabance, B. et al. (1997), Biochem. Mol. Biol. Int. 42(1) 77-84; Caen J. et al. (1993), J. Dairy Sci. 76(1): 301-310]. Previous studies documented potential bioactive peptides encrypted in the N-terminal oS1 amino acid sequence, but no mention was made of use of these protein fragments, specific sequences or defined synthetic peptides to enhance hematopoiesis, prevent viral infection or modulate the development of autoimmune diseases.

SUMMARY OF THE INVENTION

According to the present invention there is provided a method of preventing or treating an autoimmune disease, the method comprising administering to a subject in need thereof a therapeutically effective amount of a peptide derived from an N terminus portion of oS1 casein.

Further according to the present invention there is provided a method of preventing or treating a viral disease, the method comprising administering to a subject in need thereof a therapeutically effective amount of a peptide derived from an N terminus portion of oS1 casein.

Further according to the present invention there is provided a method of preventing viral infection, the method comprising administering to a subject in need thereof a therapeutically effective amount of a peptide derived from an N terminus portion of oS1 casein.

Further according to the present invention there is provided a method of inducing hematopoiesis, the method comprising administering to a subject in need thereof a therapeutically effective amount of a peptide derived from an N terminus portion of oS1 casein.

Further according to the present invention there is provided a method of inducing hematopoietic stem cells proliferation, the method comprising administering to a subject in need thereof a therapeutically effective amount of a peptide derived from an N terminus portion of oS1 casein.

Further according to the present invention there is provided a method of inducing hematopoietic stem cells proliferation and differentiation, the method comprising administering to a subject in need thereof a therapeutically effective amount of a peptide derived from an N terminus portion of oS1 casein.

Further according to the present invention there is provided a method of inducing megakaryocytopoiesis, the method comprising administering to a subject in need thereof a therapeutically effective amount of a peptide derived from an N terminus portion of oS1 casein.

Further according to the present invention there is provided a method of inducing erythropoiesis, the method comprising administering to a subject in need thereof a therapeutically effective amount of a peptide derived from an N terminus portion of oS1 casein.

Further according to the present invention there is provided a method of inducing leukocytopoiesis, the method comprising administering to a subject in need thereof a therapeutically effective amount of a peptide derived from an N terminus portion of oS1 casein.

Further according to the present invention there is provided a method of inducing plasma cell proliferation, the method comprising administering to a subject in need thereof a therapeutically effective amount of a peptide derived from an N terminus portion of oS1 casein.

Further according to the present invention there is provided a method of inducing dendritic cell proliferation, the method comprising administering to a subject in need thereof a therapeutically effective amount of a peptide derived from an N terminus portion of oS1 casein.

Further according to the present invention there is provided a method of inducing macrophage cell proliferation, the method comprising administering to a subject in need thereof a therapeutically effective amount of a peptide derived from an N terminus portion of oS1 casein.

Further according to the present invention there is provided a method of preventing or treating thrombocytopenia, the method comprising administering to a subject in need thereof a therapeutically effective amount of a peptide derived from an N terminus portion of oS1 casein. Further according to the present invention there is provided a method of preventing or treating pancytopenia, the method comprising administering to a subject in need thereof a therapeutically effective amount of a peptide derived from an N terminus portion of oS1 casein.

Further according to the present invention there is provided a method of preventing or treating granulocytopenia, the method comprising administering to a subject in need thereof a therapeutically effective amount of a peptide derived from an N terminus portion of oS1 casein.

Further according to the present invention there is provided a method of preventing or treating hyperlipidemia, the method comprising administering to a subject in need thereof a therapeutically effective amount of a peptide derived from an N terminus portion of oS1 casein.

Further according to the present invention there is provided a method of preventing or treating hypercholesterolemia, the method comprising administering to a subject in need thereof a therapeutically effective amount of a peptide derived from an N terminus portion of oS1 casein.

Further according to the present invention there is provided a method of preventing or treating glucosuria, the method comprising administering to a subject in need thereof a therapeutically effective amount of a peptide derived from an N terminus portion of oS1 casein.

Further according to the present invention there is provided a method of preventing or treating diabetes, the method comprising administering to a subject in need thereof a therapeutically effective amount of a peptide derived from an N terminus portion of oS1 casein.

Further according to the present invention there is provided a method of preventing or treating AIDS, the method comprising administering to a subject in need thereof a therapeutically effective amount of a peptide derived from an N terminus portion of oS1 casein.

Further according to the present invention there is provided a method of preventing or treating infection by HIV, the method comprising administering to a subject in need thereof a therapeutically effective amount of a peptide derived from an N terminus portion of oS1 casein.

Further according to the present invention there is provided a method of preventing or treating conditions associated with myeloablative doses of chemoradiotherapy supported by autologous bone marrow or peripheral blood stem cell transplantation (ASCT) or allogeneic bone marrow transplantation (BMT), the method comprising administering to a subject in need thereof a therapeutically effective amount of a peptide derived from an N terminus portion of oS1 casein.

Further according to the present invention there is provided a method of treating a thrombopoietin treatable condition, the method comprising administering to a subject in need thereof a therapeutically effective amount of a peptide derived from an N terminus portion of oS1 casein.

Further according to the present invention there is provided a method of augmenting the effect of thrombopoietin, the method comprising administering to a subject in need thereof a therapeutically effective amount of a peptide derived from an N terminus portion of oS1 casein.

Further according to the present invention there is provided a method of enhancing peripheral stem cell mobilization, the method comprising administering to a subject in need thereof an effective amount of a pharmaceutical composition comprising effective amounts of thrombopoietin and a peptide derived from an N terminus portion of $\alpha$ S1 casein.

Further according to the present invention there is provided a pharmaceutical composition for preventing or treating an autoimmune disease, the pharmaceutical composition comprising, as an active ingredient, a peptide derived from an N terminus portion of oS1 casein and a pharmaceutically acceptable carrier.

Further according to the present invention there is provided a pharmaceutical composition for preventing or treating a viral disease, the pharmaceutical composition comprising, as an active ingredient, a peptide derived from an N terminus portion of oS1 casein and a pharmaceutically acceptable carrier.

Further according to the present invention there is provided a pharmaceutical composition for preventing viral infection, the pharmaceutical composition comprising, as an active ingredient, a peptide derived from an N terminus portion of oS1 casein and a pharmaceutically acceptable carrier.

Further according to the present invention there is provided a pharmaceutical composition for inducing hematopoiesis, the pharmaceutical composition comprising, as an active ingredient, a peptide derived from an N terminus portion of oS1 casein and a pharmaceutically acceptable carrier.

Further according to the present invention there is provided a pharmaceutical composition for inducing hematopoietic stem cells proliferation, the pharmaceutical composition comprising, as an active ingredient, a peptide derived from an N terminus portion of oS1 casein and a pharmaceutically acceptable carrier.

Further according to the present invention there is provided a pharmaceutical composition for inducing hematopoietic stem cells proliferation and differentiation, the pharmaceutical composition comprising, as an active ingredient, a peptide derived from an N terminus portion of oS1 casein and a pharmaceutically acceptable carrier.

Further according to the present invention there is provided a pharmaceutical composition for inducing megakaryocytopoiesis, the pharmaceutical composition comprising, as an active ingredient, a peptide derived from an N terminus portion of oS1 casein and a pharmaceutically acceptable carrier.

Further according to the present invention there is provided a pharmaceutical composition for inducing erythropoiesis, the pharmaceutical composition comprising, as an active ingredient, a peptide derived from an N terminus portion of oS1 casein and a pharmaceutically acceptable carrier.

Further according to the present invention there is provided a pharmaceutical composition for inducing leukocytopoiesis, the pharmaceutical composition comprising, as an active ingredient, a peptide derived from an N terminus portion of oS1 casein and a pharmaceutically acceptable carrier.

Further according to the present invention there is provided a pharmaceutical composition for inducing thrombocytopoiesis, the pharmaceutical composition comprising, as an active ingredient, a peptide derived from an N terminus portion of oS1 casein and a pharmaceutically acceptable carrier.

Further according to the present invention there is provided a pharmaceutical composition for inducing plasma cell proliferation, the pharmaceutical composition comprising, as an active ingredient a peptide derived from an N terminus portion of oS1 casein and a pharmaceutically acceptable carrier.

Further according to the present invention there is provided a pharmaceutical composition for inducing dendritic cell proliferation, the pharmaceutical composition comprising, as an active ingredient a peptide derived from an N terminus portion of oS1 casein and a pharmaceutically acceptable carrier.

Further according to the present invention there is provided a pharmaceutical composition for inducing macrophage proliferation, the pharmaceutical composition comprising, as an active ingredient a peptide derived from an N terminus portion of oS1 casein and a pharmaceutically acceptable carrier.

Further according to the present invention there is provided a pharmaceutical composition for preventing or treating thrombocytopenia, the pharmaceutical composition comprising, as an active ingredient, a peptide derived from an N terminus portion of oS1 casein and a pharmaceutically acceptable carrier.

Further according to the present invention there is provided a pharmaceutical composition for preventing or treating pancytopenia, the pharmaceutical composition comprising, as an active ingredient, a peptide derived from an N terminus portion of oS1 casein and a pharmaceutically acceptable carrier.

Further according to the present invention there is provided a pharmaceutical composition for preventing or treating granulocytopenia, the pharmaceutical composition comprising, as an active ingredient, a peptide derived from an N terminus portion of oS1 casein and a pharmaceutically acceptable carrier.

Further according to the present invention there is provided a pharmaceutical composition for preventing or treating hyperlipidemia, the pharmaceutical composition comprising, as an active ingredient, a peptide derived from an N terminus portion of oS1 casein and a pharmaceutically acceptable carrier.

Further according to the present invention there is provided a pharmaceutical composition for preventing or treating hypercholesterolemia, the pharmaceutical composition comprising, as an active ingredient, a peptide derived from an N terminus portion of oS1 casein and a pharmaceutically acceptable carrier.

Further according to the present invention there is provided a pharmaceutical composition for preventing or treating glucosuria, the pharmaceutical composition comprising, as an active ingredient, a peptide derived from an N terminus portion of oS1 casein and a pharmaceutically acceptable carrier.

Further according to the present invention there is provided a pharmaceutical composition for preventing or treating diabetes, the pharmaceutical composition comprising, as an active ingredient, a peptide derived from an N terminus portion of oS1 casein and a pharmaceutically acceptable carrier.

Further according to the present invention there is provided a pharmaceutical composition for preventing or treating AIDS, the pharmaceutical composition comprising, as an active ingredient, a peptide derived from an N terminus portion of oS1 casein and a pharmaceutically acceptable carrier.

Further according to the present invention there is provided a pharmaceutical composition for preventing or treating infection by HIV, the pharmaceutical composition comprising, as an active ingredient, a peptide derived from an N terminus portion of oS1 casein and a pharmaceutically acceptable carrier.

Further according to the present invention there is provided a pharmaceutical composition for preventing or treating conditions associated with myeloablative doses of chemoradiotherapy supported by autologous bone marrow or peripheral blood stem cell transplantation (ASCT) or allogeneic bone marrow transplantation (BMT), the pharmaceutical composition comprising, as an active ingredient, a peptide derived from an N terminus portion of oS1 casein and a pharmaceutically acceptable carrier.

Further according to the present invention there is provided a pharmaceutical composition for treating a thrombopoietin treatable condition, the pharmaceutical composition comprising, as an active ingredient a peptide derived from an N terminus portion of oS1 casein and a pharmaceutically acceptable carrier.

Further according to the present invention there is provided a pharmaceutical composition for augmenting the effect of thrombopoietin, the pharmaceutical composition comprising, as an active ingredient a peptide derived from an N terminus portion of oS1 casein and a pharmaceutically acceptable carrier.

Further according to the present invention there is provided a pharmaceutical composition for enhancing peripheral stem cell mobilization, the pharmaceutical composition comprising, as active ingredients thrombopoietin and a peptide derived from an N terminus portion of oS1 casein and a pharmaceutically acceptable carrier.

Further according to the present invention there is provided a pharmaceutical composition for enhancing hematopoiesis, the pharmaceutical composition comprising, as active ingredients thrombopoietin and a peptide derived from an N terminus portion of oS1 casein and a pharmaceutically acceptable carrier.

Further according to the present invention there is provided a pharmaceutical composition for enhancing hematopoietic stem cell proliferation, the pharmaceutical composition comprising, as active ingredients thrombopoietin and a peptide derived from an N terminus portion of oS1 casein and a pharmaceutically acceptable carrier.

Further according to the present invention there is provided a pharmaceutical composition for enhancing hematopoietic stem cell proliferation and differentiation, the pharmaceutical composition comprising, as active ingredients thrombopoietin and a peptide derived from an N terminus portion of oS1 casein and a pharmaceutically acceptable carrier.

Further according to the present invention there is provided a pharmaceutical composition for enhancing megakaryocytopoiesis, the pharmaceutical composition comprising, as active ingredients thrombopoietin and a peptide derived from an N terminus portion of oS1 casein and a pharmaceutically acceptable carrier.

Further according to the present invention there is provided a pharmaceutical composition for enhancing erythropoiesis, the pharmaceutical composition comprising, as active ingredients thrombopoietin and a peptide derived from an N terminus portion of oS1 casein and a pharmaceutically acceptable carrier.

Further according to the present invention there is provided a pharmaceutical composition for enhancing leukocytopoiesis, the pharmaceutical composition comprising, as active ingredients thrombopoietin and a peptide derived from an N terminus portion of oS1 casein and a pharmaceutically acceptable carrier.

Further according to the present invention there is provided a pharmaceutical composition for enhancing thrombocytopoiesis, the pharmaceutical composition comprising, as active ingredients thrombopoietin and a peptide derived from an N terminus portion of oS1 casein and a pharmaceutically acceptable carrier.

Further according to the present invention there is provided a pharmaceutical composition for preventing or treating thrombocytopenia, the pharmaceutical composition comprising, as active ingredients thrombopoietin and a peptide derived from an N terminus portion of oS1 casein and a pharmaceutically acceptable carrier.

Further according to the present invention there is provided a pharmaceutical composition for preventing or treating pancytopenia, the pharmaceutical composition comprising, as active ingredients thrombopoietin and a peptide derived from an N terminus portion of oS1 casein and a pharmaceutically acceptable carrier.

Further according to the present invention there is provided a pharmaceutical composition for preventing or treating granulocytopenia, the pharmaceutical composition comprising, as active ingredients thrombopoietin and a peptide derived from an N terminus portion of oS1 casein and a pharmaceutically acceptable carrier.

Further according to the present invention there is provided a pharmaceutical composition for treating or preventing an indication selected from the group consisting of autoimmune disease or condition, viral disease, viral infection, hematological disease, hematological deficiencies, thrombocytopenia, pancytopenia, granulocytopenia, hyperlipidemia, hypercholesterolemia, glucosuria, hyperglycemia, diabetes, AIDS, infection with HIV-1, helper T-cell disorders, dendrite cell deficiencies, macrophage deficiencies, hematopoietic stem cell disorders including platelet, lymphocyte, plasma cell and neutrophil disorders, pre-leukemic conditions, leukemic conditions, immune system disorders resulting from chemotherapy or radiation therapy, human immune system disorders resulting from treatment of diseases of immune deficiency and bacterial infections, the pharmaceutical composition comprising, as an active ingredient, a peptide derived from an N terminus portion of oS1 casein and a pharmaceutically acceptable carrier.

Further according to the present invention there is provided a pharmaceutical composition for treating or preventing an indication selected from the group consisting of hematological disease, hematological deficiencies, thrombocytopenia, pancytopenia, granulocytopenia, dendrite cell deficiencies, macrophage deficiencies, hematopoietic stem cell disorders including platelet, lymphocyte, plasma cell and neutrophil disorders, pre-leukemic conditions, leukemic conditions, myelodysplastic syndrome, aplastic anemia and bone marrow insufficiency, the pharmaceutical composition comprising, as active ingredients, thrombopoietin and a peptide derived from an N terminus portion of oS1 casein and a pharmaceutically acceptable carrier.

Further according to the present invention there is provided a method of enhancing colonization of donated blood stem cells in a myeloablated recipient, the method comprising treating a donor of the donated blood stem cells with a peptide derived from an N terminus portion of oS1 casein prior to donation and implanting the donated blood stem cells in the recipient. Further according to the present invention there is provided a method of enhancing colonization of donated blood stem cells in a myeloablated recipient, the method comprising treating the donated blood stem cells with a peptide derived from an N terminus portion of oS1 casein prior to implanting the donated blood stem cells in the recipient.

Further according to the present invention there is provided a method of enhancing colonization of blood stem cells in a myeloablated recipient, the method comprising treating the blood stem cells with a peptide derived from an N terminus portion of oS1 casein prior to implanting the blood stem cells in the recipient.

Further according to the present invention there is provided a method of enhancing colonization of donated blood stem cells in a myeloablated recipient, the method comprising treating a donor of the donated blood stem cells with a peptide derived from an N terminus portion of oS1 casein and thrombopoietin prior to donation and implanting the donated blood stem cells in the recipient.

Further according to the present invention there is provided a method of enhancing colonization of donated blood stem cells in a myeloablated recipient, the method comprising treating the donated blood stem cells with a peptide derived from an N terminus portion of oS1 casein and thrombopoietin prior to implanting the donated blood stem cells in the recipient.

Further according to the present invention there is provided a method of enhancing colonization of blood stem cells in a myeloablated recipient, the method comprising treating the blood stem cells with a peptide derived from an N terminus portion of oS1 casein and thrombopoietin prior to implanting the blood stem cells in the recipient.

According to further features in preferred embodiments of the invention described below, the peptide is a fragment derived by fragmentation of oS1 casein.

According to still further features in the described preferred embodiments the peptide is a synthetic peptide.

According to still further features in the described preferred embodiments the peptide has a sequence as set forth in one of SEQ ID NOs:1-25.

Further according to the present invention there is provided a purified peptide having an amino acid sequence selected from the group consisting of SEQ ID NOs:1-25.

Further according to the present invention there is provided a pharmaceutical composition comprising a purified peptide having an amino acid sequence selected from the group consisting of SEQ ID NOs:1-25 and a pharmaceutically acceptable carrier.

Further according to the present invention there is provided a pharmaceutical composition comprising thrombopoietin and a purified peptide having an amino acid sequence selected from the group consisting of SEQ ID NOs:1-25 and a pharmaceutically acceptable carrier.

The present invention successfully addresses the shortcomings of the presently known configurations by providing peptides for the treatment of human disease, which peptides are derived from the N terminus portion of o S1 casein and posses no detectable toxicity and high therapeutic efficacy.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 represents NK activity at an effector: target cell ratio of 25:1 and 50:1.

FIG. 2a represents NK activity of two blood samples from the same patient, incubated at different effector:target cell ratios (1:25 and 1:50). FIG. 2b represents NK activity of blood samples from normal and affected donors incubated at the same effector:target cell ratio. Squares represent an effector:target cell ratio of 100:1, diamonds represent an effector:target cell ratio of 50:1.

FIG. 3a represents the percentage of cultured human PBSC binding fluorescent antibody CD$_{56}$ (5 independent samples) after 10 days incubation with (peptides) or without (control) 100 µg per ml peptides derived from natural casein. FIG. 3b represents the percentage of cultured human PBSC cells binding fluorescent anti-CD$_3$ (T cell) antibody, following 14 days of incubation with (peptides) or without (control) 100 µg per ml peptides derived from natural casein. FIG. 3c represents the percentage of cultured human PBSC cells binding fluorescent anti-CD$_3$ (T cell) antibody and cells binding both CD$_3$ and CD$_{56}$ (T and NK-like cells) antibodies after 28 days incubation with (peptides) or without (control) 100 µg per ml peptides derived from natural casein.

FIG. 4 depicts the stimulation of Natural Killer (NK) cell activity in cultured human Peripheral Blood Stem Cells (PBSC) by synthetic peptides derived from casein. Lysis of $^{35}$S labeled K562 target cells by cultured human PBSC (from a breast cancer patient) incubated without (0 µg) or with increasing concentrations (10-500 µg per ml) of synthetic peptides derived from casein is expressed as the fraction of total radioactivity released from the K562 cells into the culture supernatant (% Release). Peptides represent N-terminal sequences of 1-10 (1a, diamonds), 1-11 (2a, squares) and 1-12 (3a, triangles) first amino acids of the N terminus portion of oS1 casein (see Table 3 below for sequences of synthetic peptides).

FIG. 5a represents the incorporation of label into two samples (PBSC 1, squares, 15 days incubation; and PBSC 2, diamonds, 20 days incubation) of human Peripheral Blood Stem Cells incubated with or without (ctrl) 50-600 µg per ml peptides derived from natural casein. FIG. 5b represents the incorporation of [$^3$H]-thymidine into cultured human bone marrow cells after 21 days incubation with or without (ctrl) 50-600 µg per ml peptides derived from natural casein. Bone marrow was donated by cancer patients in remission (BM Auto, squares, BM 1, triangles, and BM 2, -?-) or healthy volunteers (BM normal, diamonds). FIG. 5c represents incorporation of [$^3$H]-thymidine into cultured human Cord Blood cells after 14 days incubation with or without (ctrl) 50-1000 µg per ml peptides derived from natural casein. Cord Blood cells were donated by two separate donors (C.B. 1, triangles, C.B. 2, squares).

FIG. 6 shows a Table depicting the proliferation of blood cell progenitors from human bone marrow and cord blood in response to incubation with peptides derived from natural casein. The relative cell number×10$^4$ per ml, reflecting the proliferation of cultured cells, was determined by counting cells as described in the Examples section that follows. Bone marrow from healthy volunteers (Bone Marrow) and Cord Blood from normal births (Cord Blood) was incubated for 13 (Cord Blood) or 14 (Bone Marrow) days in the presence of growth factors and AB serum, with or without increasing concentrations of peptides derived from natural casein (25-500 µg).

FIG. 7 shows a table depicting the effect of in-vitro incubation with Synthetic peptides derived from casein on the relative distribution of Megakaryocyte, Erythroid, Plasma and Dendritic cells (differential count) in CFU-GEMM colonies from murine bone marrow progenitor cells. Cells were scored in the macroscopic colonies grown from murine bone marrow cells prepared similarly to the CFU-GEMM colonies previously described. Cells were incubated with hematopoietic factors, and 25 µg or more of Synthetic peptides derived from casein for 14 days. The differential count is expressed as the percentage of total cells represented by individual cell types.

FIGS. 10a through 10f are selected images of cells from consecutive incubation times, demonstrating FITC-conjugated peptides derived from natural casein penetrating the Sup-$T_1$ cell membrane (FIGS. 10a, 10b) and concentrating in the nucleus (FIGS. 10c-10f).

FIG. 11 shows a Table depicting the stimulation of Sup-$T_1$ Lymphocyte cell proliferation in response to incubation with peptides derived from natural casein. Sup-$T_1$ cells (5000 per well) were incubated with increasing concentrations (50-1000 μg per ml) of peptides derived from natural casein, counted in their wells at the indicated times post culture and pulsed with [$^3$H]-thymidine for 18 hours. Proliferation index is the ratio of the average of the incorporation of [$^3$H]-thymidine into triplicate samples divided by the incorporation into cells cultured without peptides derived from natural casein (control).

FIG. 12 shows a Table depicting inhibition of HIV-1 infection of CEM lymphocytes by peptides derived from natural casein. CEM cells were preincubated with increasing concentrations (50-1000 μg per ml) of peptides derived from natural casein for the indicated number of hours (3, 24 and 48 hours) before contact with HIV-1 virus, as described in the Examples section that follows. On day 15 post infection, cells were counted for cell numbers and assayed for severity of HIV-1 infection by the P34 antigen assay, as described in the Examples section that follows. Control cultures were IF: CEM cells contacted with HIV-1 virus without pretreatment with peptides derived from natural casein, and UIF: CEM cells cultured under identical conditions without peptides derived from natural casein and without contact with HIV-1 virus.

FIG. 13 shows a Table depicting inhibition of HIV-1 infection of CEM lymphocytes by Synthetic peptides derived from casein. CEM cells were preincubated with various concentrations (10-250 μg per ml) of peptides derived from natural casein (1P, 3P and 4P) for 3 hours before contact with HIV-1 virus, as described in the Examples section that follows. On day 7 post infection, cells were counted for cell numbers and assayed for severity of HIV-1 infection by the P34 antigen assay, as described in the Examples section that follows. Control cultures (IF) were CEM cells contacted with HIV-1 virus without pretreatment with peptides derived from natural casein.

FIG. 15 depicts the reduction by Synthetic peptides derived from casein of diet-induced hypercholesterol/hyperlipidemia in female C57 Black/6j mice. Total cholesterol (TC), High Density (HDL) and Low Density Lipoproteins (LDL) were assayed in pooled blood of two (2) mice per sample from hypercholesterol/hyperlipidemic mice receiving (IP) casein-derived peptides B, C, 2a or 3P, or no treatment (control). "Normal" samples represent control mice not fed the atherogenic diet.

FIG. 16 shows a Table depicting the stimulation of hematopoiesis in cancer patients in response to injections of peptides derived from natural casein. Peripheral blood from five female cancer patients either receiving or having received chemotherapy, as described above, was counted for total White Blood Cells (WBC, ×$10^3$), Platelets (PLT, ×$10^3$), Erythrocytes (RBC, ×$10^3$) and Hemoglobin (gm per dl) before (n) and after (n+ . . . ) intramuscular injections with peptides derived from natural casein, as described above. Patient 1 relates to G.T.; patient 2 relates to E.C.; patient 3 relates to E.S.; patient 4 relates to J.R. and patient 5 relates to D.M.

DESCRIPTION OF THE PREFERRED EMBODIMENTS

Figure 1:
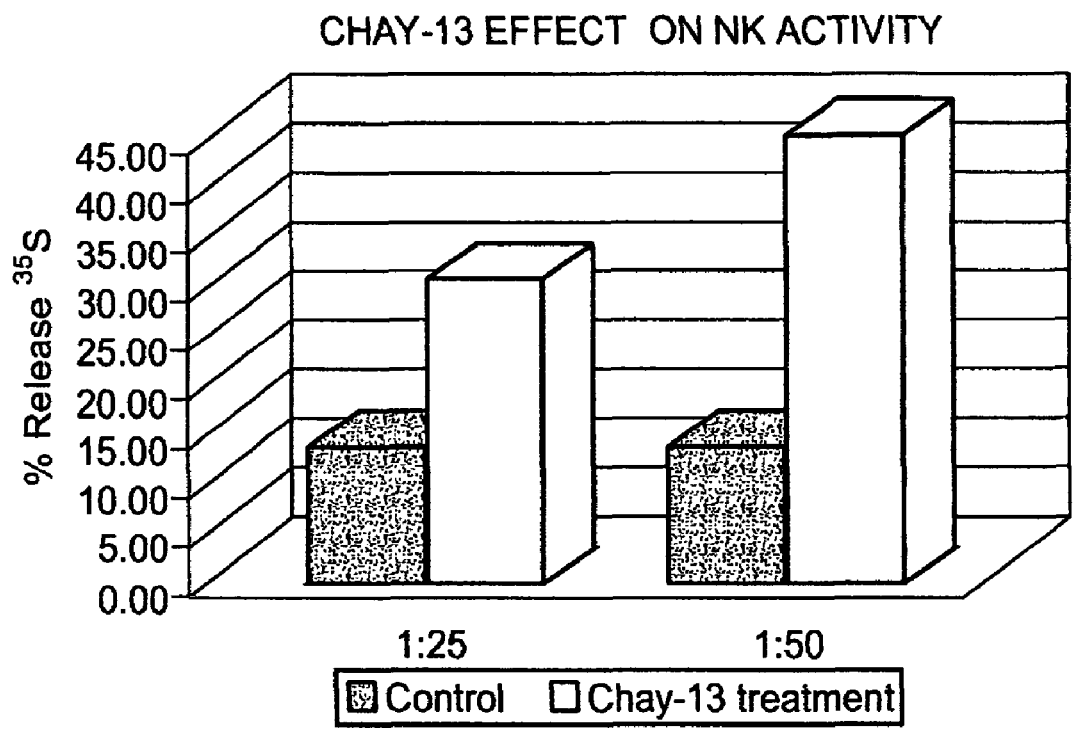
FIG. 1 depicts the stimulation of Natural Killer (NK) cell activity in cultured murine bone marrow cells by peptides derived from natural casein. Lysis of $^{35}$S labeled YAC target cells by cultured murine bone marrow cells incubated in the presence or absence of 100 µg per ml peptides derived from natural casein is expressed as the fraction of total radioactivity released from the YAC cells into the culture supernatant (% Release $^{35}$S).

The present invention is of biologically active peptides that are derived from or are similar to sequences identical with the N-terminus of the oS1 fraction of milk casein, compositions containing same and methods of utilizing same in, for example, stimulating and enhancing immune response, protecting against viral infection, normalizing serum cholesterol levels, and stimulating hematopoiesis. The casein-derived peptides are non-toxic and can be used to treat and prevent, for example, immune pathologies, hypercholesterolemia, hematological disorders and viral-related diseases.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As used herein, the term "treating" includes substantially inhibiting, slowing or reversing the progression of a disease, substantially ameliorating clinical symptoms of a disease.

As used herein, the term "preventing" includes substantially preventing the appearance of clinical symptoms of a disease.

As used herein the term "peptide" includes native peptides (either degradation products, synthetically synthesized peptides or recombinant peptides) and peptido-mimetics (typically, synthetically synthesized peptides), such as peptoids and semipeptoids which are peptide analogs, which may have, for example, modifications rendering the peptides more stable while in a body. Such modifications include, but are not limited to, cyclization, N terminus modification, C terminus modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, backbone modification and residue modification. Methods for preparing peptido-mimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further detail in this respect are provided hereinunder.

Thus, a peptide according to the present invention can be a cyclic peptide. Cyclization can be obtained, for example, through amide bond formation, e.g., by incorporating Glu, Asp, Lys, Orn, di-amino butyric (Dab) acid, di-aminopropionic (Dap) acid at various positions in the chain (—CO—NH or —NH—CO bonds). Backbone to backbone cyclization can also be obtained through incorporation of modified amino acids of the formulas H—N(($CH_2$)$_n$—COOH)—C(R)H—COOH or H—N(($CH_2$)$_n$—COOH)—C(R)H—$NH_2$, wherein n=1-4, and further wherein R is any natural or non-natural side chain of an amino acid.

Cyclization via formation of S—S bonds through incorporation of two Cys residues is also possible. Additional side-chain to side chain cyclization can be obtained via formation of an interaction bond of the formula —(—$CH_2$—)$_n$—S—$CH_2$—C—, wherein n=1 or 2, which is possible, for example, through incorporation of Cys or homoCys and reaction of its free SH group with, e.g., bromoacetylated Lys, Orn, Dab or Dap.

Peptide bonds (—CO—NH—) within the peptide may be substituted, for example, by N-methylated bonds (—N($CH_3$)—CO—), ester bonds (—C(R)H—C—O—O—C(R)—N—), ketomethylen bonds (—CO—$CH_2$—), o-aza bonds (—NH—N(R)—CO—), wherein R is any alkyl, e.g., methyl, carba bonds (—$CH_2$—NH—), hydroxyethylene bonds (—CH(OH)—$CH_2$—), thioamide bonds (—CS—NH—), olefinic double bonds (—CH=CH—), retro amide bonds (—NH—CO—), peptide derivatives (—N(R)—$CH_2$—CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

Tables 1-2 below list all the naturally occurring amino acids (Table 1) and non-conventional or modified amino acids (Table 2).

TABLE 1

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-Carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgin |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |

TABLE 2-continued

| Non-conventional amino acid | Code | Non-conventional amino acid | Code |
|---|---|---|---|
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylaspartate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | Penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | Penicillamine | Pen |
| L-homophenylalanine | Hphe | L-α-methylalanine | Mala |

TABLE 2-continued

| Non-conventional amino acid | Code | Non-conventional amino acid | Code |
|---|---|---|---|
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methylvaline | Mtrp | L-α-methyltyrosine | Mtyr |
| L-α-methylleucine | Mval | L-N-methylhomophenylalanine | Nmhphe |
|  | Nnbhm |  |  |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl ethylamino)cyclopropane | Nmbc |  |  |

A peptide according to the present invention can be used in a self standing form or be a part of moieties such as proteins and display moieties such as display bacteria and phages. The peptides of the invention can also be chemically modified to give active dimers or multimers, in one polypeptide chain or covalently crosslinked chains.

Additionally, a peptide according to the present invention includes at least two, optionally at least three, optionally at least four, optionally at least five, optionally at least six, optionally at least seven, optionally at least eight, optionally at least nine, optionally at least ten, optionally at least eleven, optionally at least twelve, optionally at least thirteen, optionally at least fourteen, optionally at least fifteen, optionally at least sixteen, optionally at least seventeen, optionally at least eighteen, optionally at least nineteen, optionally at least twenty, optionally at least twenty-one, optionally at least twenty-two, optionally at least twenty-three, optionally at least twenty-four, optionally at least twenty-five, optionally at least twenty-six, optionally between twenty-seven and sixty, or more amino acid residues (also referred to herein interchangeably as amino acids).

Accordingly, as used herein the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

As used herein the phrase "derived from an N terminus portion of oS1 casein" refers to peptides as this term is defined herein, e.g., cleavage products of oS1 casein (referred to herein as peptides derived from natural casein), synthetic peptides chemically synthesized to correspond to the amino acid sequence of an N terminus portion of oS1 casein (referred to herein as synthetic peptides derived from casein), peptides similar (homologous) to an N terminus portion of oS1 casein, for example, peptides characterized by one or more amino acid substitutions, such as, but not limited to, permissible substitutions, provided that at least 70%, preferably at least 80%, more preferably at least 90% similarity is maintained, and functional homologues thereof. The terms "homologues" and "functional homologues" as used herein mean peptides with any insertions, deletions and substitutions which do not affect the biological activity of the peptide.

As used herein the term "oS1 casein" refers to oS1 casein of a mammal, including, but not limited to, livestock mammals (e.g., cow, sheep, goat, mare, camel, deer and buffalo) human beings and marine mammals. The following provides a list of oS1 caseins having a known amino acid sequence, identified by their GenBank (NCBI) Accession Nos. and source: CAA26982 (*Ovis aries* (sheep)), CAA51022 (*Capra hircus* (goat)), CAA42516 (*Bos taurus* (bovine)), CAA55185 (*Homo sapiens*), CAA38717 (*Sus scrofa* (pig)), P09115 (rabbit) and O97943 (*Camelus dromedurius* (camel)).

As used herein the term "N terminus portion" refers to M amino acids of αS1 casein derived from the first 60 amino acids of oS1 casein, wherein M is any of the integers between 2 and 60 (including the integers 2 and 60). Preferably, the term refers to the first M amino acids of αS casein.

The peptides of the invention can be obtained by extraction from milk as previously described, or by solid phase peptide synthesis, which is a standard method known to the man skilled in the art. Purification of the peptides of the invention is performed by standard techniques, known to the man skilled in the art, such as high performance liquid chromatography (HPLC). Milk casein fragmentation to obtain the peptides of the invention may be effected using various enzymatic and/or chemical means.

As is further detailed here in under and exemplified in the Examples section that follows, the peptides of the present invention have a variety of therapeutic effects. In the Examples section there are provided numerous assays with which one of ordinary skills in the art can test a specific peptide designed in accordance with the teachings of the present invention for a specific therapeutic effect.

Any of the peptides described herein can be administered per se or be formulated into a pharmaceutical composition which can be used for treating or preventing a disease. Such a composition includes as an active ingredient any of the peptides described herein and a pharmaceutically acceptable carrier.

As used herein a "pharmaceutical composition" refers to a preparation of one or more of the peptides described herein, with other chemical components such as pharmaceutically suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water. Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition.

Suitable routes of administration may, for example, include oral, rectal, transmucosal, transdermal, intestinal or parenteral delivery, including intramuscular, subcutaneous and intramedullary injections as well as intrathecal, direct intraventricular, intravenous, intraperitoneal, intranasal, or intraocular injections.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the active peptides into preparations which, can be used pharmaceutically. Proper formulation is dependent upon the route of administration chosen.

For injection, the peptides of the invention may be formulated in aqueous solutions, preferably in physiologically compatible buffers such as Hank's solution, Ringer's solution, or physiological saline buffer with or without organic solvents such as propylene glycol, polyethylene glycol. For transmucosal administration, penetrants are used in the formulation. Such penetrants are generally known in the art.

For oral administration, the peptides can be formulated readily by combining the active peptides with pharmaceutically acceptable carriers well known in the art. Such carriers enable the peptides of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethyl-cellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active ingredient doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active peptides may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the peptides according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The peptides described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active peptides may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the peptides to allow for the preparation of highly concentrated solutions.

Alternatively, the active ingredient may be in powder form for constitution with a suitable vehicle, e.g., sterile, pyrogen-free water, before use.

The peptides of the present invention may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Persons ordinarily skilled in the art can easily determine optimum dosages and dosing methodology for any of the peptides of the invention.

For any peptide used in accordance with the teachings of the present invention, a therapeutically effective amount, also referred to as a therapeutically effective dose, which can be estimated initially from cell culture assays or in vivo animal assays. For example, a dose can be formulated in animal models to achieve a circulating concentration range that includes the $IC_{50}$ or the $IC_{100}$ as determined in cell culture. Such information can be used to more accurately determine useful doses in humans. Initial dosages can also be estimated from in vivo data. Using these initial guidelines one having ordinary skill in the art could determine an effective dosage in humans.

Moreover, toxicity and therapeutic efficacy of the peptides described herein can be determined by standard pharmaceutical procedures in cell cultures or experimental animals, e.g., by determining the $LD_{50}$ and the $ED_{50}$.

The dose ratio between toxic and therapeutic effect is the therapeutic index and can be expressed as the ratio between $LD_{50}$ and $ED_{50}$. Peptides which exhibit high therapeutic indices are preferred. The data obtained from these cell cultures assays and animal studies can be used in formulating a dosage range that is not toxic for use in human. The dosage of such peptides lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition (see, e.g., Fingl et al., 1975, In: The Pharmacological Basis of Therapeutics, chapter 1, page 1).

Dosage amount and interval may be adjusted individually to provide plasma levels of the active ingredient which are sufficient to maintain therapeutic effect. Usual patient dosages for oral administration range from about 50-2000 mg/kg/administration, commonly from about 100-1000 mg/kg/administration, preferably from about 150-700 mg/kg/administration and most preferably from about 250-500 mg/kg/administration. In some cases, therapeutically effective serum levels will be achieved by administering multiple doses each day. In cases of local administration or selective uptake, the effective local concentration of the drug may not be related to plasma concentration. One having skill in the art will be able to optimize therapeutically effective local dosages without undue experimentation.

Depending on the severity and responsiveness of the condition to be treated, dosing can also be a single administration of a slow release composition, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc. Compositions of the present invention may, if desired, be presented in a pack or dispenser device, such as FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a peptide of the invention formulated in a compatible pharmaceutical carrier may also be prepared, placed in an appropriate container, and labeled for treatment or prevention of an indicated condition or induction of a desired event. Suitable indicia on the label may include treatment and/or prevention of an autoimmune disease or condition, viral disease, viral infection, bacterial infection, hematological disease, hematological deficiencies, thrombocytopenia, pancytopenia, granulocytopenia, hyperlipidemia, hypercholesterolemia, glucosuria, hyperglycemia, diabetes, AIDS, infection with HIV-1, helper T-cell disorders, dendrite cell deficiencies, macrophage deficiencies, hematopoietic stem cell disorders including platelet, lymphocyte, plasma cell and neutrophil disorders, hematopoietic stem cell proliferation, hematopoietic stem cell proliferation and differentiation, pre-leukemic conditions, leukemic conditions, immune system disorders resulting from chemotherapy or radiation therapy, and human immune system disorders resulting from treatment of diseases of immune deficiency.

The pharmaceutical compositions according to the invention may be useful in maintaining and/or restoring blood system constituents, in balancing blood cell counts, in balancing levels of metabolites in the blood including sugar, cholesterol, calcium, uric acid, urea and enzymes such as alkaline phosphatase. Further, the pharmaceutical compositions of the invention may be useful in inducing blood cell proliferation, modulating white and/or red blood cell counts, particularly increasing white and/or red blood cell counts, elevating haemoglobin blood level and in modulating platelet counts.

The term "balancing" as used herein with relation to levels of certain physiological parameters, means changing the levels of referred parameters and bringing them closer to normal values.

The term "normal values" as used herein with relation to physiological parameters, means values which are in the range of values of healthy humans or animals.

In specifically preferred embodiments, the peptides of the invention balance counts of red blood cells, white blood cells, platelets and haemoglobin level. The pharmaceutical compositions of the invention may be used for activating blood cell proliferation.

In addition, the pharmaceutical compositions may be used for the treatment and/or prevention of hemopoietic stem cell disorders, including platelet, lymphocyte, plasma cell and neutrophil disorders, as well as deficiency and malfunction in pre-leukemic and leukemic conditions and thrombocytopenia.

Further, the pharmaceutical compositions may be used for the treatment and/or prevention of cell proliferative diseases. In this connection, it is worth noting that the pharmaceutical compositions of the invention are advantageous in the stimulation of the immune response during chemotherapy or radiation treatments, in alleviating the negative effects, reducing chemotherapy and irradiation-induced vomiting and promoting a faster recovery.

Still further, the pharmaceutical compositions of the invention may be used for the stimulation of human immune response during treatment of diseases associated with immune deficiency, for example HIV and autoimmune diseases.

The compositions of the invention may also be intended for veterinary use.

The pharmaceutical compositions of the invention may be used in the treatment and/or prevention of, for example, disorders involves abnormal levels of blood cells, disorders involving hemopoietic stem cells production and differentiation, treatment of platelet, lymphocyte and/or neutrophil disorders, for the treatment of pre-leukemic and leukemic conditions and for the treatment of thrombocytopenia. The pharmaceutical compositions of the invention may also be used in the treatment of cell proliferative diseases and diseases involving immune deficiency, such as HIV, and of autoimmune diseases. Further, the pharmaceutical compositions of the invention may be used for modulating the immune response during chemotherapy or radiation treatments, for example for reducing chemotherapy-associated vomiting.

While reducing the present invention to practice, it was surprisingly observed that the peptides of the invention exert a synergistic effect on human hematopoietic stem cell proliferation and differentiation with addition of other hematopoietic growth factors. Of notable significance was the dose-dependent enhancement of thrombopoietin (TPO) induction of megakaryocyte proliferation by peptides of the present invention. Thrombopoietin is an early acting cytokine with important multilineage effects: TPO alone, or in combination with other early acting cytokines, can (i) promote viability and suppress apoptosis in progenitor cells; (ii) regulate hematopoietic stem cell production and function; (iii) trigger cell division of dormant multipotent cells; (iv) induce multilineage differentiation and (v) enhance formation of multilineage colonies containing granulocytes, erythrocytes, macrophages, and megakaryocytes (MK, CFU-GEMM). Moreover, TPO stimulates the production of more limited progenitors for granulocyte/monocyte, megakaryocyte and erythroid colonies, stimulates adhesion of primitive human bone marrow and megakaryocytic cells to fibronectin and fibrinogen. Thus, TPO is an important cytokine for clinical hematologists/transplanters: for the mobilization, amplification and ex vivo expansion of stem cells and committed precursor cells for autologous and allogeneic transplantation. In addition, administration of TPO to healthy platelet donors has been employed to enhance pheresis yields. However, clinical application of TPO therapy is complicated by, among other considerations, relatively high costs of the recombinant human cytokine rhTPO, and the potential antigenicity of TPO with repeated administration.

Combined treatment with TPO and the peptide of the present invention, either together in a pharmaceutical composition comprising both, or separately, can provide inexpensive, proven non-toxic augmentation of TPOs effects on target cell proliferation and function. In such a combination, the peptide of the present invention may be applied to the treatment of, in addition to the abovementioned conditions, disorders such as myelodysplastic syndrome (MDS), aplastic anemia and complications of liver failure. Pre-treatment of platelet donors with the peptide of the present invention, alone or in combination with TPO, may even further enhance the efficiency of pheresis yields.

Thus, according to the present invention there is provided a method of treating a thrombopoietin treatable condition, the method effected by administering to a subject in need thereof a therapeutically effective amount of a peptide derived from an N terminus portion of oS1 casein.

Further according to the present invention there is provided a method of augmenting the effect of thrombopoietin, the method effected by administering to a subject in need thereof a therapeutically effective amount of a peptide derived from an N terminus portion of oS1 casein.

Further according to the present invention there is provided a method of enhancing peripheral stem cell mobilization, the method effected by administering to a subject in need thereof an effective amount of a pharmaceutical composition comprising effective amounts of thrombopoietin and a peptide derived from an N terminus portion of α S1 casein.

Further according to the present invention there is provided a pharmaceutical composition for treating a thrombopoietin treatable condition, the pharmaceutical composition comprising, as an active ingredient a peptide derived from an N terminus portion of oS1 casein and a pharmaceutically acceptable carrier.

Further according to the present invention there is provided a pharmaceutical composition for augmenting the effect of thrombopoietin, the pharmaceutical composition comprising, as an active ingredient a peptide derived from an N terminus portion of oS1 casein and a pharmaceutically acceptable carrier.

Further according to the present invention there is provided a pharmaceutical composition for enhancing peripheral stem cell mobilization, the pharmaceutical composition comprising, as active ingredients thrombopoietin and a peptide derived from an N terminus portion of α S1 casein and a pharmaceutically acceptable carrier.

Further according to the present invention there is provided a pharmaceutical composition for inducing hematopoiesis, the pharmaceutical composition comprising, as active ingredients, thrombopoietin and a peptide derived from an N terminus portion of oS1 casein and a pharmaceutically acceptable carrier.

Further according to the present invention there is provided a pharmaceutical composition for inducing hematopoietic stem cells proliferation, the pharmaceutical composition comprising, as active ingredients, thrombopoietin and a peptide derived from an N terminus portion of oS1 casein and a pharmaceutically acceptable carrier.

Further according to the present invention there is provided a pharmaceutical composition for inducing hematopoietic stem cells proliferation and differentiation, the pharmaceutical composition comprising, as active ingredients, thrombopoietin and a peptide derived from an N terminus portion of oS1 casein and a pharmaceutically acceptable carrier.

Further according to the present invention there is provided a pharmaceutical composition for inducing megakaryocytopoiesis, the pharmaceutical composition comprising, as active ingredients, thrombopoietin and a peptide derived from an N terminus portion of oS1 casein and a pharmaceutically acceptable carrier.

Further according to the present invention there is provided a pharmaceutical composition for inducing erythropoiesis, the pharmaceutical composition comprising, as active ingredients, thrombopoietin and a peptide derived from an N terminus portion of oS1 casein and a pharmaceutically acceptable carrier.

Further according to the present invention there is provided a pharmaceutical composition for inducing leukocytopoiesis, the pharmaceutical composition comprising, as active ingredients, thrombopoietin and a peptide derived from an N terminus portion of oS1 casein and a pharmaceutically acceptable carrier.

Further according to the present invention there is provided a pharmaceutical composition for inducing thrombocytopoiesis, the pharmaceutical composition comprising, as active ingredients, thrombopoietin and a peptide derived from an N terminus portion of oS1 casein and a pharmaceutically acceptable carrier.

Further according to the present invention there is provided a pharmaceutical composition for preventing or treating thrombocytopenia, the pharmaceutical composition comprising, as active ingredients, thrombopoietin and a peptide derived from an N terminus portion of oS1 casein and a pharmaceutically acceptable carrier.

Further according to the present invention there is provided a pharmaceutical composition for preventing or treating pancytopenia, the pharmaceutical composition comprising, as active ingredients, thrombopoietin and a peptide derived from an N terminus portion of oS1 casein and a pharmaceutically acceptable carrier.

Further according to the present invention there is provided a pharmaceutical composition for preventing or treating granulocytopenia, the pharmaceutical composition comprising, as active ingredients, thrombopoietin and a peptide derived from an N terminus portion of oS1 casein and a pharmaceutically acceptable carrier.

Further according to the present invention there is provided a pharmaceutical composition for treating or preventing an indication selected from the group consisting of hematological disease, hematological deficiencies, thrombocytopenia, pancytopenia, granulocytopenia, dendrite cell deficiencies, macrophage deficiencies, hematopoietic stem cell disorders including platelet, lymphocyte, plasma cell and neutrophil disorders, pre-leukemic conditions, leukemic conditions, myelodysplastic syndrome, aplastic anemia and bone marrow insufficiency, the pharmaceutical composition comprising, as active ingredients, thrombopoietin and a peptide derived from an N terminus portion of oS1 casein and a pharmaceutically acceptable carrier.

Further according to the present invention there is provided a pharmaceutical composition comprising thrombopoietin and a purified peptide having an amino acid sequence selected from the group consisting of SEQ ID NOs:1-25 and a pharmaceutically acceptable carrier.

Further according to the present invention there is provided a method of enhancing colonization of donated blood stem cells in a myeloablated recipient, the method effected by treating a donor of the donated blood stem cells with a peptide derived from an N terminus portion of oS1 casein and thrombopoietin prior to donation and implanting the donated blood stem cells in the recipient.

Further according to the present invention there is provided a method of enhancing colonization of donated blood stem cells in a myeloablated recipient, the method effected by treating the donated blood stem cells with a peptide derived from an N terminus portion of oS1 casein and thrombopoietin prior to implanting the donated blood stem cells in the recipient.

Further according to the present invention there is provided a method of enhancing colonization of blood stem cells in a myeloablated recipient, the method comprising treating the blood stem cells with a peptide derived from an N terminus portion of oS1 casein and thrombopoietin prior to implanting the blood stem cells in the recipient.

The invention further relates to anti-bacterial pharmaceutical compositions comprising as active ingredient at least one peptide of the invention and to the use of the peptides of the invention as anti-bacterial agents.

Thus, according to the present invention there is provided a method of preventing or treating an autoimmune disease, the method is effected by administering to a subject in need thereof a therapeutically effective amount of a peptide derived from an N terminus portion of oS1 casein.

Further according to the present invention there is provided a method of preventing or treating a viral disease, the method is effected by administering to a subject in need thereof a therapeutically effective amount of a peptide derived from an N terminus portion of oS1 casein.

Further according to the present invention there is provided a method of preventing viral infection, the method is effected by administering to a subject in need thereof a therapeutically effective amount of a peptide derived from an N terminus portion of oS1 casein.

Further according to the present invention there is provided a method of inducing hematopoiesis, the method is effected by administering to a subject in need thereof a therapeutically effective amount of a peptide derived from an N terminus portion of oS1 casein.

Further according to the present invention there is provided a method of inducing hematopoietic stem cells proliferation, the method is effected by administering to a subject in need thereof a therapeutically effective amount of a peptide derived from an N terminus portion of oS1 casein.

Further according to the present invention there is provided a method of inducing hematopoietic stem cells proliferation and differentiation, the method is effected by administering to a subject in need thereof a therapeutically effective amount of a peptide derived from an N terminus portion of oS1 casein.

Further according to the present invention there is provided a method of inducing megakaryocytopoiesis, the method is effected by administering to a subject in need thereof a therapeutically effective amount of a peptide derived from an N terminus portion of oS1 casein.

Further according to the present invention there is provided a method of inducing erythropoiesis, the method is effected by administering to a subject in need thereof a therapeutically effective amount of a peptide derived from an N terminus portion of oS1 casein.

Further according to the present invention there is provided a method of inducing leukocytopoiesis, the method is effected by administering to a subject in need thereof a therapeutically effective amount of a peptide derived from an N terminus portion of oS1 casein.

Further according to the present invention there is provided a method of inducing thrombocytopoiesis, the method is effected by administering to a subject in need thereof a therapeutically effective amount of a peptide derived from an N terminus portion of oS1 casein.

Further according to the present invention there is provided a method of inducing plasma cell proliferation, the method is effected by administering to a subject in need thereof a therapeutically effective amount of a peptide derived from an N terminus portion of oS1 casein.

Further according to the present invention there is provided a method of inducing dendritic cell proliferation, the method is effected by administering to a subject in need thereof a therapeutically effective amount of a peptide derived from an N terminus portion of oS1 casein.

Further according to the present invention there is provided a method of inducing macrophage cell proliferation, the method is effected by administering to a subject in need thereof a therapeutically effective amount of a peptide derived from an N terminus portion of oS1 casein.

Further according to the present invention there is provided a method of preventing or treating thrombocytopenia, the method is effected by administering to a subject in need thereof a therapeutically effective amount of a peptide derived from an N terminus portion of oS1 casein.

Further according to the present invention there is provided a method of preventing or treating pancytopenia, the method is effected by administering to a subject in need thereof a therapeutically effective amount of a peptide derived from an N terminus portion of oS1 casein.

Further according to the present invention there is provided a method of preventing or treating granulocytopenia, the method is effected by administering to a subject in need thereof a therapeutically effective amount of a peptide derived from an N terminus portion of oS1 casein.

Further according to the present invention there is provided a method of preventing or treating hyperlipidemia, the method is effected by administering to a subject in need thereof a therapeutically effective amount of a peptide derived from an N terminus portion of oS1 casein.

Further according to the present invention there is provided a method of preventing or treating hypercholesterolemia, the method is effected by administering to a subject in need thereof a therapeutically effective amount of a peptide derived from an N terminus portion of oS1 casein.

Further according to the present invention there is provided a method of preventing or treating glucosuria, the method is effected by administering to a subject in need thereof a therapeutically effective amount of a peptide derived from an N terminus portion of oS1 casein.

Further according to the present invention there is provided a method of preventing or treating diabetes, the method is effected by administering to a subject in need thereof a therapeutically effective amount of a peptide derived from an N terminus portion of oS1 casein.

Further according to the present invention there is provided a method of preventing or treating AIDS, the method is effected by administering to a subject in need thereof a therapeutically effective amount of a peptide derived from an N terminus portion of oS1 casein.

Further according to the present invention there is provided a method of preventing or treating infection by HIV, the method is effected by administering to a subject in need thereof a therapeutically effective amount of a peptide derived from an N terminus portion of oS1 casein.

Further according to the present invention there is provided a method of preventing or treating conditions associated with myeloablative doses of chemoradiotherapy supported by autologous bone marrow or peripheral blood stem cell transplantation (ASCT) or allogeneic bone marrow transplantation (BMT), the method is effected by administering to a subject in need thereof a therapeutically effective amount of a peptide derived from an N terminus portion of oS1 casein.

Further according to the present invention there is provided a pharmaceutical composition for preventing or treating an autoimmune disease, the pharmaceutical composition comprising, as an active ingredient, a peptide derived from an N terminus portion of oS1 casein and a pharmaceutically acceptable carrier.

Further according to the present invention there is provided a pharmaceutical composition for preventing or treating a viral disease, the pharmaceutical composition comprising, as an active ingredient, a peptide derived from an N terminus portion of oS1 casein and a pharmaceutically acceptable carrier.

Further according to the present invention there is provided a pharmaceutical composition for preventing viral infection, the pharmaceutical composition comprising, as an active ingredient, a peptide derived from an N terminus portion of oS1 casein and a pharmaceutically acceptable carrier.

Further according to the present invention there is provided a pharmaceutical composition for inducing hematopoiesis, the pharmaceutical composition comprising, as an active ingredient, a peptide derived from an N terminus portion of oS1 casein and a pharmaceutically acceptable carrier.

Further according to the present invention there is provided a pharmaceutical composition for inducing hematopoietic stem cells proliferation, the pharmaceutical composition comprising, as an active ingredient, a peptide derived from an N terminus portion of oS1 casein and a pharmaceutically acceptable carrier.

Further according to the present invention there is provided a pharmaceutical composition for inducing hematopoietic stem cells proliferation and differentiation, the pharmaceutical composition comprising, as an active ingredient, a peptide derived from an N terminus portion of oS1 casein and a pharmaceutically acceptable carrier.

Further according to the present invention there is provided a pharmaceutical composition for inducing megakaryocytopoiesis, the pharmaceutical composition comprising, as an active ingredient, a peptide derived from an N terminus portion of oS1 casein and a pharmaceutically acceptable carrier.

Further according to the present invention there is provided a pharmaceutical composition for inducing erythropoiesis, the pharmaceutical composition comprising, as an active ingredient, a peptide derived from an N terminus portion of oS1 casein and a pharmaceutically acceptable carrier.

Further according to the present invention there is provided a pharmaceutical composition for inducing leukocytopoiesis, the pharmaceutical composition comprising, as an active ingredient, a peptide derived from an N terminus portion of oS1 casein and a pharmaceutically acceptable carrier.

Further according to the present invention there is provided a pharmaceutical composition for inducing thrombocytopoiesis, the pharmaceutical composition comprising, as an active ingredient, a peptide derived from an N terminus portion of oS1 casein and a pharmaceutically acceptable carrier.

Further according to the present invention there is provided a pharmaceutical composition for inducing plasma cell proliferation, the pharmaceutical composition comprising, as an active ingredient a peptide derived from an N terminus portion of oS1 casein and a pharmaceutically acceptable carrier.

Further according to the present invention there is provided a pharmaceutical composition for inducing dendritic cell proliferation, the pharmaceutical composition comprising, as an active ingredient a peptide derived from an N terminus portion of oS1 casein and a pharmaceutically acceptable carrier.

Further according to the present invention there is provided a pharmaceutical composition for inducing macrophage proliferation, the pharmaceutical composition comprising, as an active ingredient a peptide derived from an N terminus portion of oS1 casein and a pharmaceutically acceptable carrier.

Further according to the present invention there is provided a pharmaceutical composition for preventing or treating thrombocytopenia, the pharmaceutical composition comprising, as an active ingredient, a peptide derived from an N terminus portion of oS1 casein and a pharmaceutically acceptable carrier.

Further according to the present invention there is provided a pharmaceutical composition for preventing or treating pancytopenia, the pharmaceutical composition comprising, as an active ingredient, a peptide derived from an N terminus portion of oS1 casein and a pharmaceutically acceptable carrier.

Further according to the present invention there is provided a pharmaceutical composition for preventing or treating granulocytopenia, the pharmaceutical composition comprising, as an active ingredient, a peptide derived from an N terminus portion of oS1 casein and a pharmaceutically acceptable carrier.

Further according to the present invention there is provided a pharmaceutical composition for preventing or treating hyperlipidemia, the pharmaceutical composition comprising, as an active ingredient, a peptide derived from an N terminus portion of oS1 casein and a pharmaceutically acceptable carrier.

Further according to the present invention there is provided a pharmaceutical composition for preventing or treating hypercholesterolemia, the pharmaceutical composition comprising, as an active ingredient, a peptide derived from an N terminus portion of oS1 casein and a pharmaceutically acceptable carrier.

Further according to the present invention there is provided a pharmaceutical composition for preventing or treating glucosuria, the pharmaceutical composition comprising, as an active ingredient, a peptide derived from an N terminus portion of oS1 casein and a pharmaceutically acceptable carrier.

Further according to the present invention there is provided a pharmaceutical composition for preventing or treating diabetes, the pharmaceutical composition comprising, as an active ingredient, a peptide derived from an N terminus portion of oS1 casein and a pharmaceutically acceptable carrier.

Further according to the present invention there is provided a pharmaceutical composition for preventing or treating AIDS, the pharmaceutical composition comprising, as an active ingredient, a peptide derived from an N terminus portion of oS1 casein and a pharmaceutically acceptable carrier.

Further according to the present invention there is provided a pharmaceutical composition for preventing or treating infection by HIV, the pharmaceutical composition comprising, as an active ingredient, a peptide derived from an N terminus portion of oS1 casein and a pharmaceutically acceptable carrier.

Further according to the present invention there is provided a pharmaceutical composition for preventing or treating conditions associated with myeloablative doses of chemoradiotherapy supported by autologous bone marrow or peripheral blood stem cell transplantation (ASCT) or allogeneic bone marrow transplantation (BMT), the pharmaceutical composition comprising, as an active ingredient, a peptide derived from an N terminus portion of oS1 casein and a pharmaceutically acceptable carrier.

Further according to the present invention there is provided a purified peptide having an amino acid sequence selected from the group consisting of SEQ ID NOs:1-25.

Further according to the present invention there is provided a pharmaceutical composition comprising a purified peptide having an amino acid sequence selected from the group consisting of SEQ ID NOs:1-25 and a pharmaceutically acceptable carrier.

The present invention successfully addresses the shortcomings of the presently known configurations by providing peptides for the treatment of human disease, which peptides are derived from the N terminus portion of o S1 casein and posses no detectable toxicity and high therapeutic efficacy.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Materials and Experimental Methods

Preparation of peptides derived from natural casein: The casein fraction of cow's milk was isolated as described by Hipp et al. (1952), ibid., and subjected to exhaustive proteolytic digestion with chymosin (also known as rennin) (20 ng per ml) at 30° C. Upon completion of the reaction, the solution was heated to inactivate the enzyme, and the digest was precipitated as paracaseinate by acidification with an organic acid, acetic or trichloracetic acid. Paracaseinate was separated by centrifugation, and the supernatant fraction, containing the peptide fragments of interest, was dialyzed and re-precipitated as caseicidin by higher acid concentrations. The resulting caseicidin, following re-suspension, dialysis and neutralization was lyophilized. The resulting powdered preparation was assayed for biological activity as described below, and separated by HPLC for peptide analysis.

HPLC analysis of peptides derived from natural casein: Peptides derived from natural casein as described above were analyzed by HPLC in two stages. Initially, the lyophilized casein digests were separated using a C 18 reversed phase with a 0.1% water triflouroacetic acid (w/w)-acetonitrile gradient. Detection was according to UV absorption at 214 nm. Following this the samples were analyzed by HPLC-Mass Spectroscopy (MS) equipped with an electrospray source. Mass calculations represent the mass of the ionized peptide samples, as derived from the retention times. Following separation, the amino acid composition of the peptides was determined with a gas-phase microsequencer (Applied Biosystems 470A).

The following data is representative: Eight peptide peaks were typically observed of which 3 were major peaks having Rt values of 17.79, 19.7, 23.02 and 5 were minor peaks having Rt values of 12.68, 14.96, 16.50, 21.9 and 25.1, which Rt values represent molecular mass of 2764, 1697, 1880, 2616, 3217, 2333, 1677 and 1669 Da, respectively. At Rt of 17.79 (corresponding to 2,764 Da) a major peak of a peptide of 23 amino acids representing amino acids 1-23 of oS1 casein, having the sequence RPKHPIKHQGLPQEVLNENLLRF (SEQ ID NO:15, see McSweeny et al., 1993, ibid., for the complete sequence of oS1 casein). Other peptides were from positions 208-224 of β casein, positions 16-37 of oS1 casein and positions 197-222 of oS2 like casein precursor. Other peptides were also present.

Synthetic peptides derived from casein: Peptides of increasing lengths corresponding to the N-terminal 1-25 amino acids of oS1 casein were synthesized by NoVetide Ltd., Haifa, Israel, with purity of >95% (HPLC). Quality Control included: HPLC, Mass Spectrometry (EI), Amino acid analysis and Peptide Content. Table 3 below provides the sequence of these peptides:

TABLE 3

| Identification | Sequence (N terminus-C terminus) | No. of amino acids | SEQ ID NO: |
|---|---|---|---|
| 74 | RP | 2 | 1 |
| 1P | RPK | 3 | 2 |
| 2P | RPKH | 4 | 3 |
| 3P | RPKHP | 5 | 4 |
| 4P | RPKHPI | 6 | 5 |
| 5P | RPKHPIK | 7 | 6 |
| Y | RPKHPIKH | 8 | 7 |
| X | RPKHPIKHQ | 9 | 8 |

TABLE 3-continued

| Identification | Sequence (N terminus-C terminus) | No. of amino acids | SEQ ID NO: |
|---|---|---|---|
| 1a | RPKHPIKHQG | 10 | 9 |
| 2a | RPKHPIKHQGL | 11 | 10 |
| 3a | RPKHPIKHQGLP | 12 | 11 |
| A | RPKHPIKHQGLPQ | 13 | 12 |
| B | RPKHPIKHQGLPQE | 14 | 13 |
| C | RPKHPIKHQGLPQEV | 15 | 14 |
| D | RPKHPIKHQGLPQEVL | 16 | 15 |
| E | RPKHPIKHQGLPQEVLN | 17 | 16 |
| F | RPKHPIKHQGLPQEVLNE | 18 | 17 |
| G | RPKHPIKHQGLPQEVLNEN | 19 | 18 |
| H | RPKHPIKHQGLPQEVLNENL | 20 | 19 |
| I | RPKHPIKHQGLPQEVLNENLL | 21 | 20 |
| J | RPKHPIKHQGLPQEVLNENLLR | 22 | 21 |
| K | RPKHPIKHQGLPQEVLNENLLRF | 23 | 22 |
| L | RPKHPIKHQGLPQEVLNENLLRFF | 24 | 23 |
| M | RPKHPIKHQGLPQEVLNENLLRFFV | 25 | 24 |
| N | RPKHPIKHQGLPQEVLNENLLRFFVA | 26 | 25 |

Juvenile (Type I, IDDM) Diabetes in Non-Obese Diabetic (NOD) Mice:

Peptides Derived from Natural Casein:

NOD mice are a commonly used model for research of autoimmune disease and human Juvenile Diabetes. Six week old female NOD mice received either one or two injections per week of 100 μg of peptides derived from natural casein, for a total of 5 or 11 treatments. Control mice received no treatment. The severity of disease was determined according to glucosuria, which was measured using Combi test sticks [Gross, D. J. et al. (1994), Diabetology, 37:1195]. Results were expressed as the percent of glucosuria-free mice in each sample over a 365-day period.

Synthetic Peptides Derived from Casein:

In another experiment, 6 week old female NOD mice received one injection per week of 100 μg of Synthetic peptides derived from casein for a total of 5 treatments. Control mice received no treatment. Results were expressed as the number of healthy mice in the various treated groups.

Intraperitoneal Glucose Tolerance Test (IPGTT):

The glucose tolerance test is the definitive method for investigating glucose metabolism and diabetic tendencies in mammals. Twenty five (25) weeks after receiving Synthetic peptides derived from casein, response to a glucose load was assessed with an intraperitoneal glucose tolerance test. Glucose injection consisted of 1 g/kg body weight. Glycemic values were determined from blood drawn prior to test (0 minutes) and 60 minutes after loading. Plasma glucose levels were determined with a Glucose Analyzer 2 (Beckman Instruments, Fullerton, Calif.) and expressed as mmol/L. Normal values do not exceed 140 mmol/L.

Stimulation of Proliferation of Natural Killer (NK) Cells:

From human Peripheral Blood Stem Cells (PBSC): PBSC of G-CSF treated subjects were separated on a FICOLL gradient, washed twice with RPMI-1640 medium and seeded into 1.5 ml wells with or without peptides derived from natural casein or synthetic peptides derived from casein, as indicated, (0-500 μg per ml). Following two days incubation the cells were assayed for Natural Killer activity by measuring radioactivity released from $^{35}$S-labeled K562 target cells (NEG-7Q9A, 185.00 MBq, 2.00 mCi EASYTAGth Methionine, L-[$^{35}$S] 43.48 TBq per mmol, 1175.0 Ci per mmol, 0.488 ml, Boston USA). Two concentrations of effector cells (2.5× $10^4$ and $5×10^4$ cells per well) were incubated with $5×10^3$ target cells per well (effector:target cell ratios of 50:1 and 100:1, respectively) in U-bottomed 96 well tissue culture plates. The cells were incubated for 5 hours at 37° C. in 5% $CO_2$, 95% air and precipitated by 5 minutes centrifugation at 1000 rpm. $^{35}$S release was measured in 50 μl samples of the supernatant liquid.

From murine Bone Marrow (BM) cells: Bone marrow was collected from 4 untreated BALB/c and C57B1/6 mice. Bone marrow was harvested from the long bones of front and hind limbs of the mice by injection of medium using a 25 Gauge needle. Aspirated cells were washed with RPMI 1640, counted in a haemocytometer and vital-stained (20 μl of cells in 380 μl acetic acid-trypan blue), then seeded in culture bottles at 2-5×$10^6$ cells per ml in RPMI-1640 containing 10% Fetal Calf Serum, antibiotics and glutamine with or without 100 μg per ml peptides derived from natural casein. The cell cultures were incubated in 5% $CO_2$, 95% air for 12-15 days at 37° C., harvested by 10 minutes centrifugation at 1500 rpm, counted, and seeded in U-bottom wells with $^{51}$Cr (Chromium-51, 740 MBq, 2.00 mCi activity) or $^{35}$S (NEG-709A, 185.00 MBq, 2.00 mCi EASYTAGth Methionine, L-[$^{35}$S] 43.48 TBq per mmol, 1175.0 Ci per mmol, 0.488 ml, Boston USA) labeled murine lymphoma (YAC) cells at either 25:1 or 50:1 effector:target cell ratio. NK activity is expressed as the percent radioactivity in the cell-free supernatants.

Proliferation of human cells in culture: Peripheral blood (PB) was collected from healthy or affected patients. Affected patients received no treatment other than G-CSF supplementation prior to plasmapheresis. Bone marrow (BM) cells were collected from consenting healthy patients or affected patients in remission following chemotherapy by medium injection into the medullary space and aspiration. Umbilical cord blood was collected during normal births. Human cells of the various origins were separated on a FICOLL gradient, washed twice with RPMI-1640 medium, and seeded into 0.2 ml flat bottom tissue culture wells at the indicated concentrations with or without peptides derived from natural casein or with or without synthetic peptides derived from casein, as indicated. All treatments, including controls, were repeated in triplicate. Cell proliferation was measured by addition of radioactive thymidine [thymidine (methyl-[$^3$H]) Specific activity 6.7 Ci per ml 37 MBq per ml, ICN Corp.] following incubation for the indicated number of days. Cells were then incubated 16-20 hours with the label, harvested and washed twice with medium. Incorporated radioactivity was measured in a β scintillation counter.

Proliferation of K562 leukemia and colon cancer cell lines: Colon and K526 are established lines of cancer cells grown in culture. Both cell lines were grown in culture bottles in 5% $CO_2$, 95% air at 37° C., harvested and washed with medium before seeding in tissue culture wells at $4×10^5$ cells (K562) or $3×10^3$ cells (Colon) per well. Peptides derived from natural casein were added to the wells, at the indicated concentrations, and after 9 (K562) or 3 (Colon) days of incubation labeled thymidine was added as described above. Harvesting and measurement of radioactive uptake was as described above.

Fluorescent Antibody Detection of NK and T Cell Proliferation in Human Peripheral Blood Stem Cells (PBSC):

Peripheral Blood Stem cells (PBSC) from human subjects receiving G-CSF treatment were collected by plasmapheresis, separated on a FICOLL gradient, washed twice with RPMI-1640 medium containing 10% Fetal Calf Serum and incubated in culture bottles at 37° C. in 5% $CO_2$, 95% air with or without peptides derived from natural casein at the indicated concentrations. Following 10, 14 or 28 days incubation with peptides derived from natural casein, the presence of T cells ($CD_3$ surface antigen) and NK cells ($CD_{56}$ surface antigen) was detected by direct immunofluorescence using anti-$CD_3$ fluorescent antibody ($CD_3$/FITC clone $UHCT_1$), anti-$CD_{56}$ fluorescent antibody ($CD_{56}$/RPE clone MOC-1) (DAKO A/S, Denmark) and mouse IgG1/RPE and IgG1/FITC antibodies as a control. Detection of fluorescently tagged cells was performed using fluorescence activated cell sorting (FACS) and fluorescent microscopy.

Stimulation of Hematopoiesis from Bone Marrow (BM) Cells in Culture:

Proliferation of megakaryocytes in multipotential colonies (CFU-GEMM) from murine Bone Marrow cells: Primary bone marrow cells ($1 \times 10^5$ per ml) from 8-12 week-old C3H/HeJ mice were grown in serum-free methyl cellulose-IMDM medium for 8-9 days at 5% $CO_2$, 95% air, at 37° C. The medium, appropriate for the growth of multipotential colonies (CFU-GEMM), contained 1% BSA (Sigma), $10^{-4}$ M thioglycerol (Sigma), $2.8 \times 10^{-4}$ M human transferrin (TF, Biological industries, Israel), 10% WEHI-CM as a source of IL-3 and 2 units per ml erythropoietin (rhEPO, R & D Systems, Minneapolis). Colonies were scored after 8-9 days using an Olympus dark field microscope. They were picked with a micropipette, cytocentrifuged and stained with May-Grunwald-Giemsa for differential counts. At least 700 cells were counted for each preparation.

Proliferation of Dendritic cells in CFU-GEMM: Multipotent (CFU-GEMM) colonies grown from primary bone marrow cells as described for the assay of megakaryocyte proliferation above were collected, stained and counted for dendritic cells. At least 700 cells were counted for each preparation.

Proliferation of Plasma cells in CFU-GEMM: Multipotent (CFU-GEMM) colonies grown from primary bone marrow cells as described for the assay of megakaryocyte proliferation above were collected, stained and counted for plasma cells. At least 700 cells were counted for each preparation.

Proliferation of Macrophage cells in CFU-GEMM: Multipotent (CFU-GEMM) colonies grown from primary bone marrow cells as described for the assay of megakaryocyte proliferation above were collected, stained and counted for macrophage cells. At least 700 cells were counted for each preparation.

Proliferation of Red Blood Cells in CFU-GEMM: Multipotent (CFU-GEMM) colonies grown from primary bone marrow cells as described for the assay of megakaryocyte proliferation above were collected, stained and counted for red blood cells. At least 700 cells were counted for each preparation.

Proliferation of Polymorphonuclear Cells (PMN) in CFU-GEMM: Multipotent (CFU-GEMM) colonies grown from primary bone marrow cells as described for the assay of megakaryocyte proliferation above were collected, stained and counted for polymorphonuclear cells. At least 700 cells were counted for each preparation.

Proliferation of megakaryocyte- and erythroid forming cells from human bone marrow and cord blood cells: A sample of bone marrow from an apparently healthy human being was processed by density gradient separation using Histopaque-107 (Sigma Diagnostics) to obtain a purified population of mononuclear cells (MNC). Colony assays were performed in a plating medium containing final concentrations of 0.92% methyl cellulose (4000 centripase powder, Sigma Diagnostic), rehydrated in Iscoves modified Dulbecco's medium containing 36 mM sodium bicarbonate (Gibco), 30% fetal bovine serum (FBS) (Hyclone), 0.292 mg/ml glutamine, 100 units per ml penicillin and 0.01 mg per ml streptomycin (Biological Industries, Beit Haemek). Cord blood from normal births was collected and prepared as mentioned above.

Colony assay medium containing $10^5$ MNC per ml was plated in triplicate wells within a 24 well tissue culture plate (Greiner), 0.33 ml per well. The cultures were incubated at 37° C. in 5% $CO_2$, 95% air and 55% relative humidity with or without peptides derived from natural casein or synthetic peptides derived from casein, at the indicated concentrations. Plates were scored after 14 days for colonies containing more than 50 cells. Megakaryocytes were identified by indirect immunofluorescence using a highly specific rabbit antibody recognizing human platelet glycoproteins, and an FITC-conjugated goat anti-rabbit IgG. Added growth factors included 15 ng per ml leucomax (GM-CSF) (Sandoz Pharma), and 5% vol. per vol. human phyto-hemagglutinin-m (Difco Lab)-induced conditioned medium (CM) to induce development of granulocyte-monocyte colonies (CFU-GM). Erythropoietin (EPO) 2 units/ml was used to induce formation of erythroid colonies.

Alternatively, human bone marrow cells from consenting volunteer donors or patients undergoing autologous bone marrow transplantation were precultured in medium containing 10-1000 μg per ml peptides derived from natural casein, grown in semi-solid agar, and scored for granulocyte-macrophage hematopoietic colonies (GM-CFU) at 7 or 14 days post treatment.

Megakaryocytopoiesis was measured in normal bone marrow cells from healthy consenting human donors by either scoring of the number of megakaryocytes in samples of liquid culture (RPMI-1640 plus 10% human AB serum, glutamine and antibiotics) with or without 100 μg per ml peptides derived from natural casein, or in a methylcellulose assay for assessing colony formation. $2 \times 10^5$ bone marrow cells were seeded in the presence of a standard growth factor combination with or without peptides derived from natural casein. In the methylcellulose assay megakaryocytes were counted with an inverted microscope on days 12-14 after seeding.

Clinical trials using peptides derived from natural casein: In one series of trials, a single dose containing 50 mg peptides derived from natural casein was administered intra-muscular to human subjects in 3 depots, over a period of 2 hours. Clinical parameters were monitored at the indicated intervals. In other trials, patients at various stages of treatment for and/or remission from cancer and metastatic disease received peptides derived from natural casein once or twice, and were monitored for changes in the cell count of peripheral blood.

Inhibition of in vitro HIV infection of human lymphocyte cells:

Peptides: Peptides (either peptides derived from natural casein or synthetic peptides derived from casein (1-25 amino acids in length, see table 3) supplied as lyophilized powder were resuspended in RPMI complete medium and added to cell cultures at a final concentrations of 50 to 1000 μg per ml.

Cells: Several types of freshly isolated human cells (primary cells) and cell lines are known to be susceptible to in vitro HIV-1 infection, although essentially any cell displaying even low surface levels of the $CD_4$ molecule can be considered a potential target for HIV-1 infection. Two commonly used human cell lines which are highly sensitive for HIV-1 infection were chosen, CEM and Sup-T1.

CEM is a human T4-lymphoblastoid cell line initially derived by G. E. Foley et al. [(1965), Cancer 18:522] from peripheral blood buffy coat of a 4-year old caucasian female with acute lymphoblastic leukemia. These cells were continuously maintained in suspension in medium, and have been used widely for analysis of infectivity, antiviral agents and neutralizing antibodies.

Sup-T1 is a human T-lymphoblastoid cell line isolated from a pleural effusion of an 8-year old male with Non-Hodgkin's T-cell lymphoma [Smith, S. D. et al. [(1984) Cancer Research 44:5657]. This cell expresses high levels of surface $CD_4$ and is useful in studies of cell fusion, cytopathic effect and infectivity of HIV-1. Sup-T1 cells are grown in suspension in enriched medium.

Medium: Cells were grown in RPMI-1640 complete medium enriched with 10% Fetal bovine serum, 2 mM glutamine and 2 mM penicillin-streptomycin (GIBCO).

Virus: The HIV virus strain employed was HIV-1IIIB, originally designated HTLV-IIIB. Concentrated culture fluids of peripheral blood from several patients with AIDS or related diseases were used to establish a permanent productive infection in H-9 cells. This subtype B virus has high capacity to replicate in human T-cell lines. Viral titer was 5.38 ng per ml in stock solution.

FITC-labeled peptides: FITC F-1300 (Fluorescein isothiocyanate, isomer I, Sigma (F25o-2) St. Louis, Mich., USA) having excitation/emission maxima of about 494/520 nm, respectively, was employed. The amine-reactive fluorescein derivative is probably the most common fluorescent derivatization reagent for covalently labeling proteins. FITC-conjugated peptides derived from natural casein were prepared by covalent binding of FITC to the amine groups of lysine.

HIV-1 P24 antigen capture assay: An HIV-1 P24 Antigen capture assay kit employed was designed to quantitate the HIV-1 P24 core antigen, which is proportionally related to the degree of viral production in cells. This kit was purchased from the AIDS Vaccine program of the SAIC-NCI-Frederick Cancer Research Institute, P.O. Box B, Frederick, Md. 21702, USA and included 96 well plates coated with monoclonal antibody to HIV-1 P24, primary antibody-rabbit anti-HIV P24 serum, secondary antibody-Goat anti-rabbit-IgG (H+ L) peroxidase conjugated antibody, TMB peroxidase substrate system and lysed HIV-1 P24 standard. The HIV-1 P24 antigen capture assay was analyzed by Organon-Technica ELISA reader at 450 nm with a reference at 650 nm.

HIV-1 P24 antigen capture ELISA: HIV infection was measured with an indirect enzyme immunoassay which detects HIV-1 P24 core antigens in tissue culture media. Tissue culture supernatant was reacted with primary rabbit anti-HIV-1 P24 antigen and visualized by peroxidase conjugated goat anti rabbit IgG. The reaction was terminated by adding 4N $H_2SO_4$, wherein the intensity of the color developed is proportional to the amount of HIV-1 antigen present in the tissue culture supernatant.

Biological hazard level (BL-3) laboratory: All virus production isolation and infection, tissue culture of HIV-1 infected cells, P24 antigen containing supernatant harvesting and P24 antigen capture ELISA, were performed in BL-3 facility of the Hebrew University, Hadassah Medical School and were in accordance with the bio safety practices set by the NIH and CDC (USA).

Flow cytometry: A FACSort cell sorter (Becton & Dickinson, San Jose, Calif. USA) was used to (i) determine the percentage of $CD_4$ positive CEM and sup-T1 cells batches before infection with HIV-1 in order to assure the same degree of infection in each experiment; and (ii) detect T cells that harbor FITC conjugated peptides derived from natural casein in their cytoplasm and nuclei.

$CO_2$ incubator: For viral culture production cells with HIV-1, cells and virus pretreated with peptides derived from natural casein and cells which were further incubated with HIV-1, were all kept in humidified $CO_2$ incubator for the duration of the experiment.

HIV infection of human cultured $CD_{4+}$ cells: The cells (CEM, Sup-T1) were preincubated with several increasing concentrations of peptides derived from natural casein (50-1000 µg per ml) or synthetic peptides derived from casein (10-500 µg per ml) for 3, 24 (for synthetic and natural peptides) and 48 (only for natural peptides) hours and HIV-1IIIB (45 µg per ml final concentration) was added to each well thereafter. HIV-1IIIB was preincubated with the peptides for 3 hours and then added to cells (5000 cells/well) in tissue culture plates. Controls were IF (Infected, cells cultured with HIV-1 and without peptides), UIF (Uninfected, cells cultured without HIV-1 and without peptides) and UIF+Ch (Uninfected+peptides derived from natural casein, cells cultured in the presence of peptides derived from natural casein {50-1000 µg per ml}) to test the effect of peptides derived from natural casein and synthetic peptides derived from casein on cell viability and growth. Cells were counted for viability and proliferation rate on day 7, 10 and day 14 post infection (the day of P24 antigen culture supernatant harvest). Cells and tissue culture supernatants (media) were harvested and lysed immediately in 1/10 volume of 10% Triton X-100. These samples were further incubated at 37° C. for 1 hour and kept at −80° C. until tested for p24 antigen.

Confocal microscopy: A Zeiss LSM 410 confocal laser scanning system attached to TW Zeiss Axiovert 135M inverted microscope, employing the laser scanning confocal microscopy technique, was used to detect penetration of FITC conjugated peptides into cells. T cells were incubated with FITC conjugated peptides derived from natural casein in a 5% $CO_2$, 95% air, 37° C. incubator, after which the cells were washed 3 times with phosphate buffer saline (PBS) to remove unbound FITC-peptides. Cells were fixed with 3.8% formalin for 10 minutes, washed twice with PBS and resuspended in 50-100 µl PBS before viewing the cells under the microscope. Selected images of cells from different time points of incubation (15 minutes, 30 minutes, 1 hour, 1.5 hour and 3 hours) displaying various amounts of FITC-peptides derived from natural casein in their cytoplasms and nuclei were stored on 3.5" Zip derive (230 MB) and processed for pictures using Photoshop software.

[$^3$H]-thymidine incorporation test: In order to test the effect of peptides derived from natural casein on T cell proliferation, several concentrations of peptides derived from natural casein (1 µg/ml stock in RPMI) were added to Sup-T1 cell cultures in 96 flat bottom microwell plate (5000 cells/well), as described for HIV-1 infection in Sup-T1 cells. Cells were counted and their viability was determined by trypan blue dye exclusion. They were pulsed with [$^3$H]-thymidine at each time point (3, 7, 10 and 14 days) for 18 hours (over night) and harvested on glass fiber filters for radioactivity reading (Incorporation of [$^3$H]-thymidine into cellular DNA is proportional to degree of cell proliferation).

Toxicity of peptides derived from natural casein in normal, myeloablated and transplant recipient mice and guinea pigs: Intramuscular, or intravenous injections of up to 5,000 mg peptides derived from natural casein per kg animal were administered in a single dose, or in three doses to normal. A variety of strains were employed, including BALB/c, C3H/HeJ and Non-Obese Diabetic (NOD) mice. The mice were either monitored for 10 months before sacrifice and post-mortem examination (toxicity assay) or observed for 200 days (survival rate). Guinea pigs received a single intramuscular injection of 20 mg peptides derived from natural casein per animal. Fifteen days later they were sacrificed and examined for pathology.

Leukocyte and platelet reconstitution in bone marrow transplant recipient mice: BALB/c mice were lethally irradiated at a source to skin distance of 70 cm, dosage of 50 cGy per minute, for a total of 600 cGy. The irradiated mice were reconstituted with syngeneic bone marrow as described above and injected intravenously 24 hours later with 1 mg per animal peptides derived from natural casein, synthetic peptides derived from casein (13-26 amino acids, see Table 3 above), or human serum albumin (controls), following a double-blinded protocol. Leukocyte reconstitution was determined according to cell count in peripheral blood collected at indicated intervals from 6 to 12 days post treatment. Platelet reconstitution was determined by cell count in blood collected from the retro orbital plexus, into heparinized capillaries, at indicated intervals from day 6 to day 15 post treatment.

In an additional series of experiments, CBA mice were lethally irradiated (900 cGy), reconstituted and treated with peptides derived from natural casein or human serum albumin as described above. Platelet reconstitution was assayed as mentioned above.

In a third series of experiments, the mice were irradiated (800 cGy), reconstituted and injected intraperitoneally with 100 µg synthetic peptides derived from casein (peptides 3a and 4P, representing the first 6 and 12 amino acids of the N terminus of αS1 casein, respectively—see Table 3 above) daily, on days 4, 5, 6 and 7 post-transplantation. Platelet reconstitution was assayed at 10 and 12 days post-transplantation.

Reconstitution of bone marrow transplant recipient mice: C57/Black/6 mice were lethally irradiated at a source to skin distance of 70 cm, dosage of 50 cGy per minute, for a total of 600 cGy. The irradiated mice were reconstituted with syngeneic bone marrow from mice which were either treated a day prior to bone marrow aspiration with 1 mg per animal peptides derived from natural casein or not treated, following a double-blinded protocol. In one experiment mice survival was monitored for 18 days. In another experiment mice were sacrificed after 10 days and spleen colonization monitored.

Synthetic peptides derived from casein significantly reduce Cholesterol levels:

The ability of synthetic casein derived peptides to reduce cholesterol levels in 7-week old female C57Bl/6j mice was assessed after feeding an atherogenic diet. The mice were divided into groups of 8. One control group was fed a normal diet. A second control group was fed the modified Thomas Hartroft diet containing cholate (#TD 88051: Teklad, Madison, Wis.) [Gerber, D. W. et al. (2000), Journal of Lipid Research. 42, 2001]. The remaining experimental groups were all fed the modified Thomas Hartroft diet. After one week on the diet, serum cholesterol values increased significantly and the synthetic peptides derived from casein were injected intraperitoneally, 1 mg per mouse, followed by a second injection of 0.1 mg one week later.

Cholesterol blood levels were determined according to Roche Cholesterol Assay based on Roeschlou & Allin enzymatic method (Roche, Inc., Germany).

Experimental Results

Peptides derived from natural casein: Originating from the observation that curdled milk occasionally failed to support bacterial growth, a casein fragment possessing bacteriocidal properties was isolated from milk proteins (U.S. Pat. No. 3,764,670 to Katzirkatchalsky, et al.). Crude peptides derived by proteolysis of natural casein were prepared by acid precipitation of the soluble fraction of the casein proteolytic digest, dialysis and lyophilization. When tested for biological activity after extended storage, it was noted that this crude preparation, when lyophilized and stored at 4° C., remained active (in vitro and in vivo) for at least 24 months.

In order to identify the active peptides contained in the peptides derived from natural casein the lyophilized crude preparation was fractionated using high performance liquid chromatography (HPLC), as described hereinabove. All of the lyophilized samples analyzed demonstrated similar retention time profiles, with contents as described above.

Thus, a major component of the crude peptides derived from natural casein preparation is the N-terminal fragment of oS1 casein.

Peptides derived from natural casein are non-toxic in rodents and humans: Extensive investigation of the short and long term effects of high doses of peptides derived from natural casein on mice, guinea pigs and human volunteers confirmed the absence of toxicity, teratogenicity or adverse side effects of the preparation. In one series of tests, single doses representing 7,000 times the estimated effective dose of peptides derived from natural casein were administered intra muscularly to mice. Standard post-mortem pathology examination of the mice at 14 days post treatment revealed no toxic effects on internal organs or other abnormalities. Similar toxicity tests in guinea pigs revealed no abnormalities two weeks after single 20 mg intramuscular doses of peptides derived from natural casein. In another series of experiments, high doses of peptides derived from natural casein administered to healthy mice had no effect on several hematological parameters measured two weeks later, including white blood cells (WBC), red blood cells (RBC), hemoglobin (HGB), electrolytes, glucose and others. A third series of experiments tested repeated high doses of 100 mg per kg body weight in mice and rats for two weeks, revealing no allergic, delayed cutaneous or anaphylactic responses and no pathological effects upon post-mortem examination. When peptides derived from natural casein were tested for their effect on the long-term survival of irradiated, bone marrow reconstituted BALB/c and C3H/HeJ mice, survival of the treated mice (18 of 27 BALB/c and C3H/HeJ; 66%) clearly exceeded the survival rates of the albumin-treated controls (4 of 26 BALB/c and C3H/HeJ; 15%). Standard teratogenicity tests [for details see, for example, Drug Safety in Pregnancy, Folb and Dakes, p. 336, Elsevier; Amsterdam, N.Y., Oxford (1990)] in mice treated with peptides derived from natural casein revealed no effect of the peptides on any developmental parameters.

Similar to its lack of toxicity or side effects when tested in rodents, peptides derived from natural casein were safe when administered to humans as well. Comparison of blood and urine samples from seven healthy human volunteers before, during and 7 days after intramuscular injection of peptides derived from natural casein revealed no changes in any of the clinical parameters. No other negative effects were observed.

Thus, high dose and extended treatment of rodents with peptides derived from natural casein revealed no apparent toxic, pathological, hypersensitivity, teratogenic, serological or any other negative effects. Moreover, peptides derived from natural casein administration to irradiated mice, at risk for short-and long-term complications, conferred a significant survival advantage over 200-300 days. These, and the absence of any undesirable effects in healthy human volunteers receiving peptides derived from natural casein via injections clearly demonstrate the peptide's safety in parenteral administration.

Reconstitution of bone marrow in transplant recipient mice: When C57/Black/6 mice were lethally irradiated and reconstituted with syngeneic bone marrow from mice that were either treated a day prior to bone marrow aspiration with 1 mg per animal peptides derived from natural casein or not so treated, survival of irradiated mice that received bone marrow from treated mice far exceeded that of irradiated mice that received bone marrow from non treated mice (survival of irradiated mice that received bone marrow from treated mice was 15 out of 18, 10 days post irradiation; whereas survival of irradiated mice that received bone marrow from non treated mice was 4 out of 17, 10 days post irradiation). Spleens derived from irradiated mice that received bone marrow from treated mice included about twice to three times as many colonies per spleen, as compared to spleens of irradiated mice that received bone marrow from non treated mice (1-5 colonies as compared to 0-3 colonies).

Figures 2A, 2B:
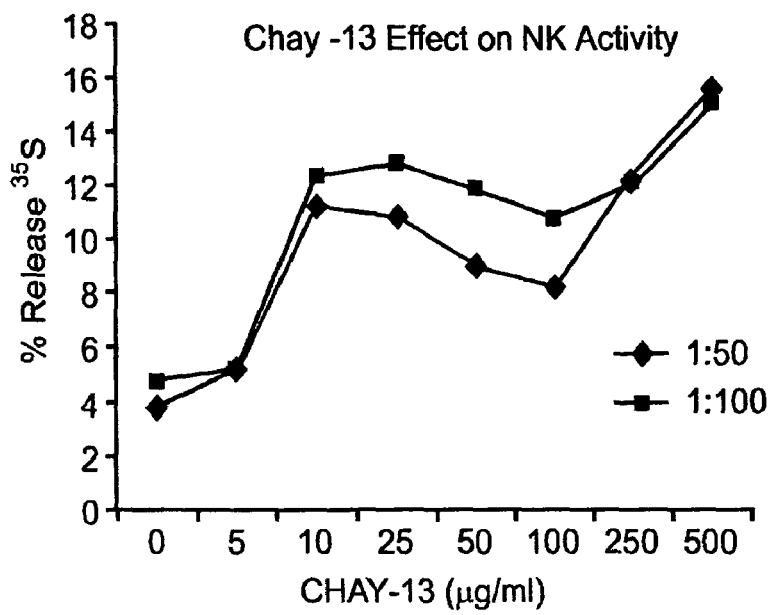
FIGS. 2a and 2b depict the stimulation of Natural Killer (NK) cell activity in cultured human Peripheral Blood Stem Cells (PBSC) by peptides derived from natural casein. Lysis of $^{35}$S labeled K562 target cells by cultured human PBSC from Granulocyte Colony Stimulating Factor (G-CSF) treated donors incubated without (0 µg) or with increasing concentrations (5-500 µg per ml) of peptides derived from natural casein is expressed as the fraction of total radioactivity released from the K562 cells into the culture supernatant (% Release $^{35}$S).

Peptides derived from natural casein stimulate the proliferation of lymphocytes: Natural killer (NK) and cytotoxic T cells are crucial to the immune system's ability to protect against invasion by both infectious pathogens and cancer cells, by both active cytotoxicity and the secretion of immunoregulatory lymphokines. Immune compromise, such as in AIDS or following chemotherapy, results in abnormal, weakened T or NK cell activity. When normal murine bone marrow cells from BALB/c and C57B1/6 mice were cultured in the presence of 100 μg per ml peptides derived from natural casein, a clear increase in NK activity was observed in both effector:target cell ratio groups. Moreover, comparison between the two groups revealed a clear dose response relationship. At the 1:25 effector:target cell ratio the average NK activity was elevated from 13.93% to 30.77% and at the 1:50 effector:target cell ratio the average NK activity was elevated from 13.68% to 44.05% (FIG. 1). Similar experiments using human Peripheral Blood Stem Cells from Granulocyte Colony Stimulating Factor-treated donors demonstrated an even more significant, concentration-dependent stimulation of target cell lysis by peptides derived from natural casein In the first set of experiments (FIG. 2a), NK activity was measured in blood samples taken from one patient and incubated at two effector:target cell ratios with increasing peptides derived from natural casein concentration. Only 4% $^{35}$S release was measured in the control, untreated PBSC culture. Almost the same percent radioactivity (4%) was found at the lowest peptide concentration (5 μg per ml). However, at higher peptide concentrations, in the range of 10 μg per ml up to 100 μg per ml, a release of 10.8-14.9% $^{35}$S was measured for effector:target cell ratios of 100:1 and 8.3-14.5% $^{35}$S for effector target cell ratios of 50:1 (FIG. 2a).

When PBS cells from normal (patient 1) and affected (patients 2-6) human donors were incubated with increasing concentrations of the peptides derived from natural casein, a significant enhancement of affected patients' NK cell activity could be measured. Thus, while the peptides derived from natural casein had a minimal effect on the normal patient's NK activity (increased from 13-15% $^{35}$S release, patient 1), PBS cells from both breast cancer and Non-Hodgkins Lymphoma patients (patients 3 and 4, for example) exhibited dramatic, dose-dependent increases in NK activity (3.5-10.8% $^{35}$S; 12.2-19.1% $^{35}$S, respectively) (FIG. 2b).

Figure 3A:
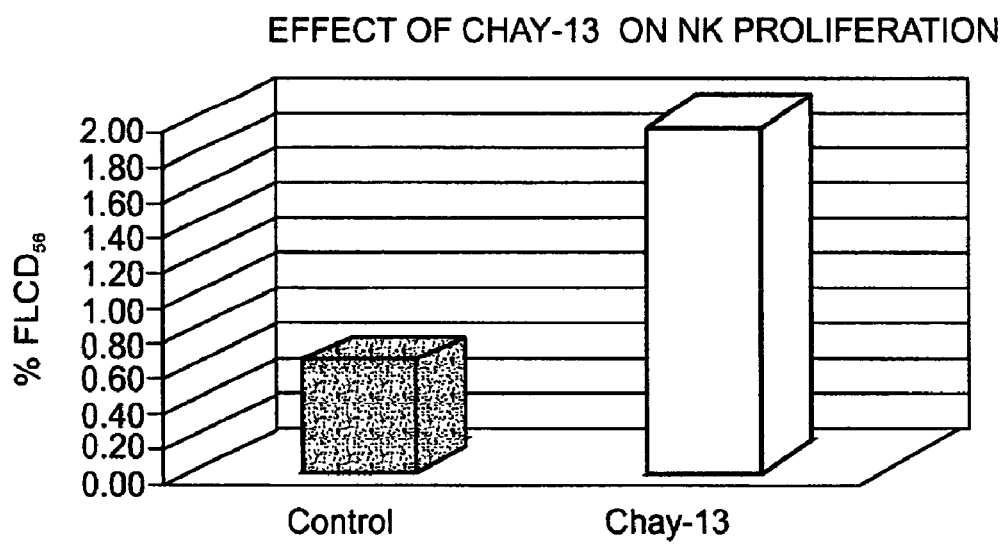
FIGS. 3a-c depict the stimulation of proliferation of Natural Killer (NK) and T-lymphocyte (T) cells from cultured human Peripheral Blood Stem Cells (PBSC) by peptides derived from natural casein. NK and T cell proliferation in cultured PBSC from Granulocyte Colony Stimulating Factor treated donors incubated with or without peptides derived from natural casein is expressed as the percentage (%) of cells binding the anti-CD$_3$/FITC fluorescent anti-T cell antibody UCHT$_1$, or the anti CD$_{56}$/RPE fluorescent anti-NK cell antibody MOC-1 (DAKO A/S Denmark). Controls are FITC and RPE-conjugated anti-mouse IgG antibody.

Peptides derived from natural casein stimulate the proliferation of CD56 surface antigen positive (NK) cells: In another series of experiments Peripheral Blood Stem Cells (PBSC) from 5 human donors receiving GCSF treatment were incubated with peptides derived from natural casein for 10, 14, or 28 days, then assayed for proliferation of the CD 56 antigen. A sometimes dramatic increase in CD 56 antigen detection was observed in the peptide-treated cells from all the donors but one (patient 1). A representative response is depicted in FIG. 3a: Following 10 days of incubation with or without peptides derived from natural casein, the presence of CD56 surface antigen-positive (NK) cells was detected by direct immunofluorescent staining. % Overall, incubation with peptides derived from natural casein increased the mean percentage of the cells positively stained for CD56 from 0.64% in the control group to 2.0% following treatment (FIG. 3a).

Figure 3B:
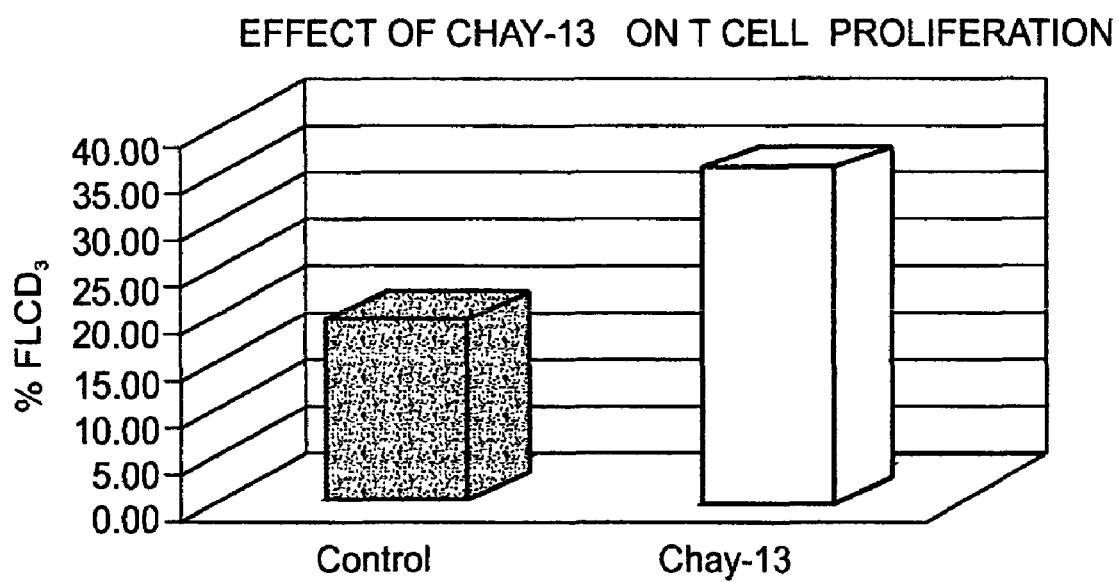

Peptides derived from natural casein stimulate the proliferation of CD3 surface antigen-positive (T) cells: The effect of peptides derived from natural casein on the proliferation of CD3 surface antigen-positive (T) cells in PBS cells from 5 subjects was assayed by direct immunofluorescence. In all but one patient (patient 4), 14 days incubation with peptides derived from natural casein significantly increased T-cell proliferation, up to more than 5 fold in some. Taken together, the mean percentage of the cells positively stained for CD3 increased from 19.45% in the control group to 35.54% in the treated group (FIG. 3b).

Figure 3C:
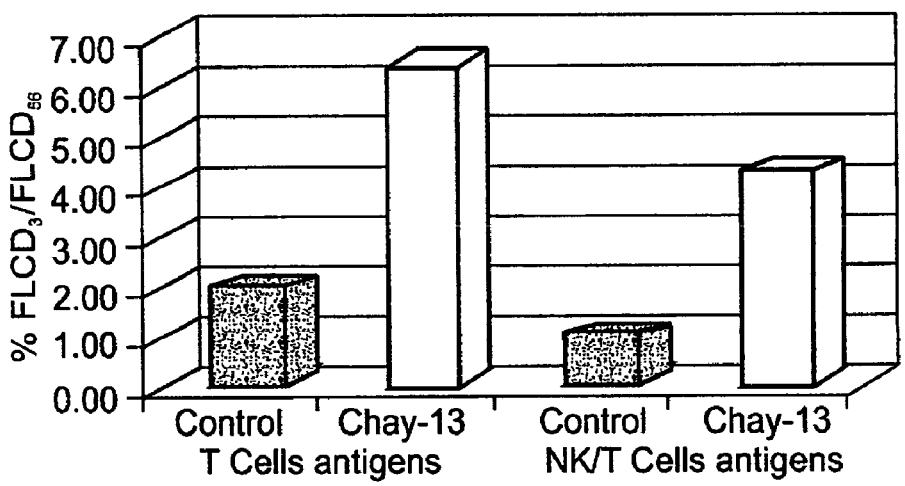

Peptides derived from natural casein stimulate the proliferation of—CD56 and CD3 (NK/T-cells) positive cells: In an additional experiment PBSCs from 7 patients were incubated with peptides derived from natural casein for 28 days, and the effect on proliferation of NK/T cells (CD56 and CD3 surface antigen-positive) was detected by direct immunofluoresence. Incubation with peptides derived from natural casein stimulated proliferation of T-cell up greater than 5 fold in some cases (patient 6), while the mean percentage of the CD3-positive (T-) cells increased from 2.08% in the control group to 6.49% in the treated group The number of both CD56 and CD3 surface antigen-positive (NK/T) cells was increased from 1.1% in the control to 4.3% in the treated group (FIG. 3c). Thus, peptides derived from natural casein stimulate the proliferation of both T-lymphocytes and Natural Killer cells from normal murine and human blood cell progenitors. Significantly, the greatest immune-stimulatory effect of the peptides derived from natural casein was noted in human donors having initially low T- and NK cell levels (FIGS. 3a-c).

Synthetic peptides derived from casein stimulate human lymphocyte proliferation in vitro: When synthetic peptides derived from casein representing the first 3 to 26 residues of oS1 casein were incubated with human PBSC cells from healthy and cancer patients (see below), a significant increase in NK cell activity was observed. Target cell lysis was greatest (from 3 to greater than 5 fold that of controls) in Non-Hodgkin's Lymphoma and Breast Cancer patient's PBSC cultures after two days incubation with as little as 10 μg per ml of peptides containing the first 9 or more residues of o S1 casein (FIG. 4). Under identical conditions, none of the peptides tested had a significant effect on NK activity in PBSC cultures from healthy human donors. Thus, even low concentrations of peptides containing the first 10 residues of the N-terminal sequence of oS1 casein are capable of selectively stimulating in vitro lymphocyte proliferation in cells from cancer patients. Similar stimulation of NK cell activity was observed when PBS cells from human donors with hematopoietic disease were incubated with Synthetic peptides derived from casein representing the first 3 amino acid residues of o S1 casein. Incubation of the PBS cells with the peptides increased target cell lysis from 2- to greater then 8-fold that of the untreated controls. Of the 5 patients tested, three (3) responded to 25 μg/ml peptide concentration, one (1) responded to 100 μg/ml peptide concentration and one (1) to 250 μg/ml. Three out of the five (5) patients responded at 25 μg/ml. No significant effect on NK activity in PBSC cultures from healthy human donors treated with the synthetic peptide representing the first 3 amino acids of oS1 casein, was observed, confirming the selective nature of the human lymphocyte-stimulating properties of casein-derived peptides.

Figure 5A:
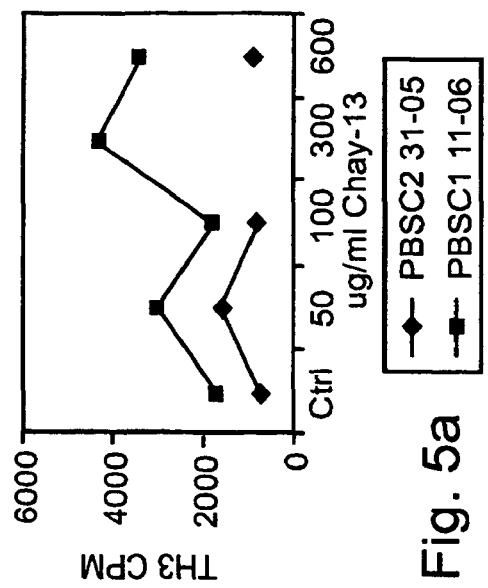
FIGS. 5a-c depict the stimulation of proliferation of cultured human cells of diverse origin by peptides derived from natural casein. Proliferation of the cultured human cells after 14-21 days incubation with increasing concentrations of the peptides derived from natural casein is expressed as the amount of [$^3$H]-thymidine incorporated into each sample.
Figure 5C:
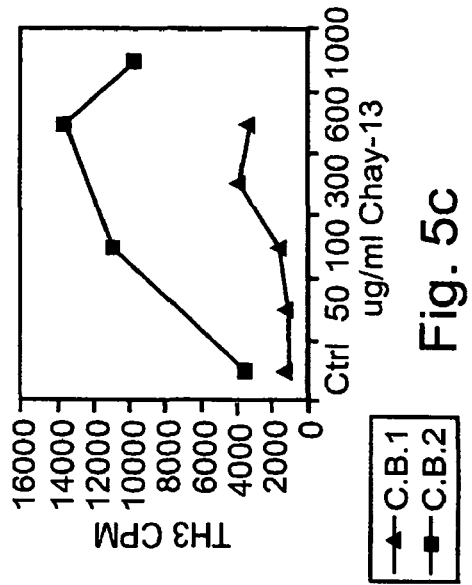
Figure 5B:
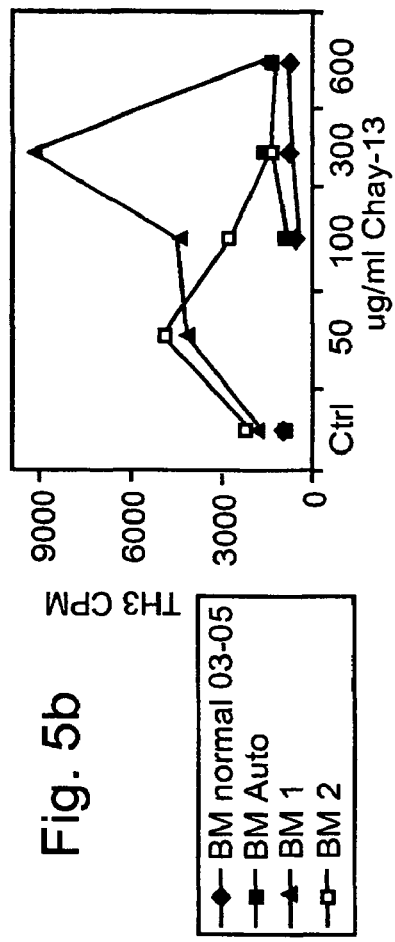

Stimulation of hematopoiesis in human blood cell progenitors: Blood cell progenitors differentiate into a variety of blood cells: macrophages, monocytes, granulocytes, lymphocytes, erythrocytes and megakaryocytes. Progenitor cells are abundant in bone marrow, but are also found in peripheral blood after Granulocyte Colony Stimulating Factor treatment (PBSC cells), in fresh Cord Blood. When increasing concentrations (50-600 μg per ml) of peptides derived from natural casein were added to cultures of human Bone Marrow, PBSC and Cord Blood, an increase in cell proliferation, as measured by [$^3$H]-thymidine incorporation was noted (FIGS. 5a-5c). Human PBSC proliferation was most greatly effected by 300 μg per ml (FIG. 5a) after 15 days in culture. An even greater effect was noted for Cord Blood cells in culture (3 to 4 fold increase in [$^3$H]-thymidine incorporation) after 14 days incubation (but not after 7 days) with peptides derived from natural casein (600 μg per ml, FIG. 5c). Cultured human bone marrow cells from three out of four donors also reacted strongly (3 to 5 fold increase in incorporation) to peptides derived from natural casein (300 μg per ml) after 21 days incubation (FIG. 5b). Thus, peptides derived from natural casein stimulate proliferation of human blood cell progenitors from bone marrow as well as other sources. Interestingly, incubation of cultured human K562 (Chronic Myeloid Leukemia) and Colon (Colon cancer) cell lines with high concentrations (up to 500 μg per ml) of peptides derived from natural casein under similar conditions had no effect on [$^3$H]-thymidine incorporation. Thus, peptides derived from natural casein stimulate proliferation of human blood cell progenitors but not growth of cancerous cells.

Stimulation of Megakaryocytopoiesis by Peptides Derived from Casein:

Peptides derived from natural casein stimulate megakaryocyte progenitor proliferation in cultured murine bone marrow cells: Multinucleated megakaryocytes develop in the bone marrow from primitive stem cells, mature to giant cells and give rise to thousands of thrombocytes per megakaryocyte. Thrombocytes are crucial for clot formation and thrombocytopenia is a major concern in myeloablative conditions (following chemotherapy or radiotherapy).

Primary bone marrow cell cultures can be induced to form CFU-GM (Granulocyte and Megakaryocyte) colonies, giving rise to megakaryocytes, and CFU-GEMM (Granulocyte, Erythroid, Macrophage and Megakaryocyte) colonies, containing additional blood cell types. Colony counts reflect expansion of specific progenitors, cell numbers reflect proliferation rates and differential cell counts reflect which specific cell lineages have developed [Patenkin, D. et al. (1990), Mol. Cel. Biol. 10, 6046-50]. In cultured murine bone marrow cells incubated with erythropoietin and IL-3, addition of 25 μg per ml peptides derived from natural casein for 8 days increased the number of CFU-GEMM two and one half fold over controls, stimulating a three fold increase in relative cell numbers per colony in the CFU-GEMM. In a similar series of experiments, addition of peptides derived from natural casein to bone marrow cells incubated with erythropoietin and conditioned medium (see Materials and Experimental Methods) stimulated a concentration-dependent increase in the percentage of early and late megakaryocytes (15% megakaryocytes without peptides, to 50% with 500 μg per ml peptides derived from natural casein). Thus, 8 days treatment with peptides derived from natural casein stimulated a significant increase in megakaryocyte formation and development in primary murine bone marrow cultures.

Synthetic Peptides Derived from Casein Stimulate Megakaryocyte Progenitor Proliferation in Cultured Murine Bone Marrow Cells:

Similar to the above and under similar experimental conditions, synthetic peptides derived from casein representing the first 5 to 24 amino acids of oS1 casein increase the percentage of early and late megakaryocytes from 15% without the synthetic peptide to more than 40% with 25 μg per ml of synthetic peptides (FIG. 7). Thus, 8 days treatment with synthetic casein derived peptides representing the first 5, 6, 11, 12, 17, 18, 19, 20, 21 and 24 amino acids stimulated a significant increase in megakaryocyte formation and development in primary murine bone marrow culture. Somewhat milder, yet appreciable, stimulation was observed with the other synthetic peptides derived from casein.

Peptides derived from natural casein stimulate Megakaryocytopoiesis in cultured human bone marrow cells: When 100 μg per ml peptides derived from natural casein were added under similar conditions to human bone marrow cell cultures from healthy donors, CFU-GM colony formation was increased with or without additional stimulating factors (GM-CSF, CM). Peptides derived from natural casein also stimulated erythroid cell forming colonies in the presence of erythropoietin. Treatment of the human bone marrow cells with thrombopoietin (TPO) stimulates megakaryocyte (MK) colony formation. Addition of 300 μg per ml peptides derived from natural casein to TPO-treated cells stimulates a more than twofold increase (16 colonies per 2×10$^5$ cells without peptides, 35 colonies per 2×10$^5$ with peptides derived from natural casein) in MK colony proliferation.

In the presence of additional hematopoietic factors, such as erythropoietin, human IL-3, hSCF and AB serum, 14 days incubation with peptides derived from natural casein stimulated a nearly three fold increase in CFU-GEMM colonies from human bone marrow cells (158 colonies with 500 μg per ml peptides derived from natural casein, 68 colonies with the factors alone), but had a smaller (one and one half fold) effect on cultured cord blood CFU-GEMM formation. The relative cell number counts in the cultured human bone marrow and cord blood colonies reflect megakaryocyte cell proliferation in response to addition of 25 μg per ml peptides derived from natural casein (see Table shown in FIG. 6). Thus, incubation of cultured human primary bone marrow and cord blood cells with peptides derived from natural casein stimulates the development and proliferation of both committed megakaryocyte and erythroid cell colonies. Significantly, the synergy observed between TPO and peptides derived from natural casein in stimulating megakaryocytopoiesis indicates a probable role for this potent hematopoietic growth factor in the mechanism of peptides derived from casein's stimulatory properties, and further suggests the likelihood of similar augmentation of a wide range of TPO-mediated effects by peptides derived from natural casein.

Synthetic peptides derived from casein stimulate Dendrific cells proliferation in murine CFU-GEMM: The effect of Synthetic peptides derived from casein on dendritic cell proliferation in murine primary bone marrow cells was assessed under the same conditions outlined for the stimulation of megakaryocytes. Synthetic peptides derived from casein representing the first: 2, 3, 5, 6, 7, 9, 11, 12, 16, 23, 24 and 26 amino acids of oS1 casein stimulated the proliferation of dendritic cells, from 2.2% and up to 23% of total cells compared with 0.1-0.2% dendritic cells in the cell samples incubated without Synthetic peptides derived from casein (FIG. 7).

Synthetic peptides derived from casein stimulate Plasma cell proliferation in murine CFU-GEMM: The effect of Synthetic peptides derived from casein on plasma cell proliferation in murine primary bone marrow cells was demonstrated under the same conditions outlined for the stimulation of megakaryocytes. Synthetic peptides derived from casein representing the first: 2, 3, 5, 7, 11, 16, 17, 18, 19, 20, 21, 22, 23 and 24 and 26 amino acids of oS1 casein, significantly stimulated the proliferation of plasma cells, from 1.5% and up 12.3% of total cell count, compared with 0.3% of total without Synthetic peptides derived from casein (FIG. 7).

Synthetic peptides derived from casein stimulate Macrophage proliferation in CFU-GEMM: The effect of Synthetic peptides derived from casein on macrophage proliferation in murine primary bone marrow cells was demonstrated under the same conditions outlined for the stimulation of megakaryocytes. Incubation of cells with synthetic peptides derived from casein representing the first: 7, 9, 16, and 23 amino acids of oS1 casein significantly stimulated the proliferation of macrophages, from approximately 17% of total cell count in unincubated controls, to nearly 30% of total in cells incubated with Synthetic peptides derived from casein (FIG. 7).

Synthetic peptides derived from casein stimulate Red Blood Cells proliferation in CFU-GEMM: The effect of Synthetic peptides derived from casein on red blood cell proliferation in murine primary bone marrow cells was demonstrated under the same conditions outlined for the stimulation of megakaryocytes. Incubation of cells with Synthetic peptides derived from casein representing the first 4 amino acids from the N terminus of oS1 casein significantly stimulated the proliferation of red blood cells, from 53% of total cell count in unincubated controls, to 71% of total in cells incubated with the synthetic peptide derived from casein (FIG. 7).

Synthetic peptides derived from casein stimulate Polymorphonuclear (PMN) cell proliferation in CFU-GEMM: The effect of Synthetic peptides derived from casein on the proliferation of polymorphonuclear (PMN) cells in murine primary bone marrow cells was demonstrated under the same conditions outlined for the stimulation of megakaryocytes. Incubation of cells with Synthetic peptides derived from casein representing the first: 3, 6, 7, 9, 16 and more, up to and including 26 amino acids of oS1 casein significantly stimulated the proliferation of PMNs, from 1.6% of total cell count in unincubated controls, to between 2.9% and 14.9% of total in cells incubated with Synthetic peptides derived from casein (FIG. 7).

Peptides derived from natural casein stimulate hematopoiesis in vivo following irradiation and bone marrow transplant: Myeloablative therapy may lead to life-threatening reduction in thrombocytes and leukocytes, which may persist despite administration of blood cells and growth factors. The following demonstrates the effect of peptides derived from natural casein following irradiation and bone marrow transplantation.

Figure 8:
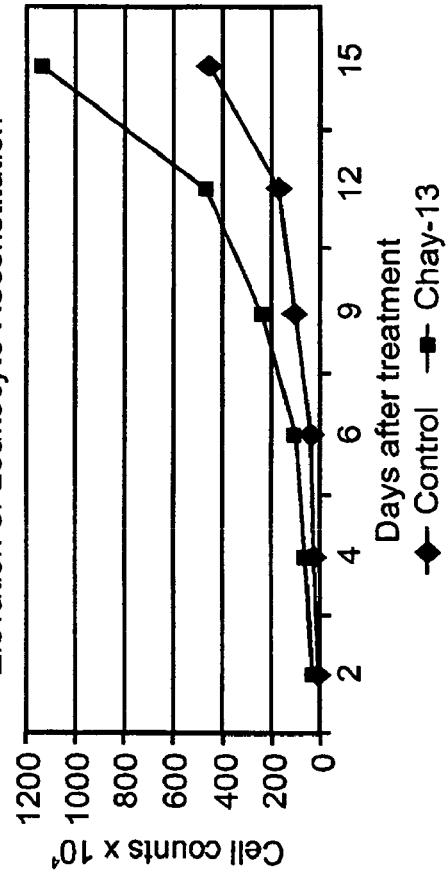
FIG. 8 depicts the stimulation of peripheral white blood cell reconstitution in myeloablated, bone marrow transplanted mice in response to treatment with peptides derived from natural casein. Cell counts represent the number of white blood cells (×10$^4$ per ml, as counted in a haemocytometer). The mice (n=6 per group) received lethal irradiation and syngeneic bone marrow transplantation ($10^6$ cells per mouse) on the following day, and intravenous administration of 1 mg per recipient peptides derived from natural casein (peptides: squares) or 1 mg per recipient human serum albumin (CONTROL: diamonds) one day later.
Figure 9:
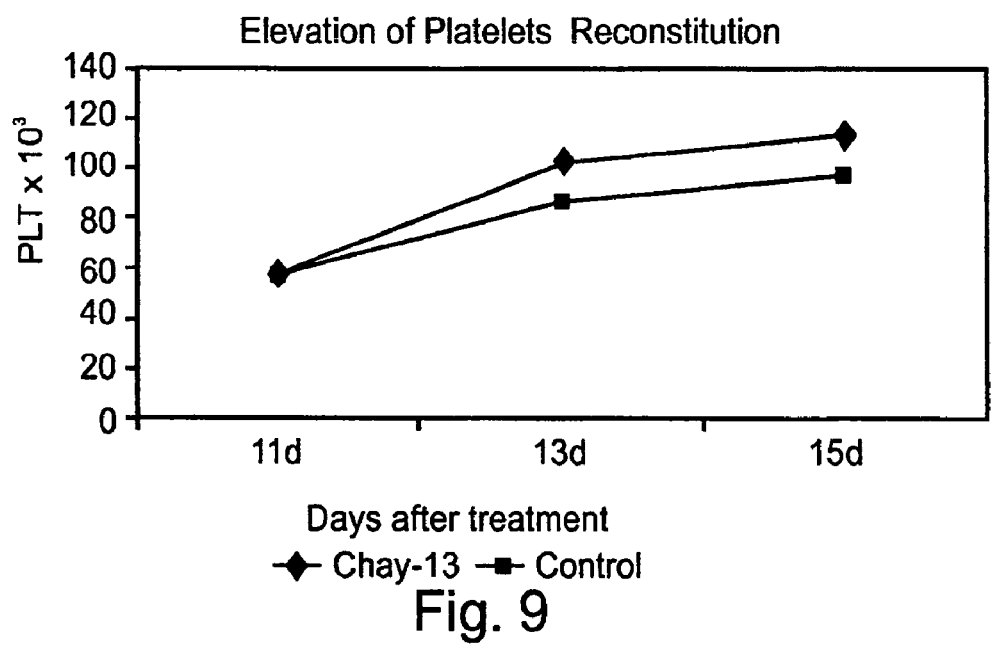
FIG. 9 depicts the stimulation of platelet reconstitution in myeloablated, bone marrow transplanted mice in response to treatment with peptides derived from natural casein. Platelet (PLT) counts represent the number of thrombocytes (×103 per ml, as counted in a haemocytometer). The mice (n=60 per group) received lethal irradiation and syngeneic bone marrow transplantation ($10^6$ cells per mouse) on day 1, and intravenous administration of 1 mg per recipient peptides derived from natural casein (Peptides, diamonds) or 1 mg per recipient human serum albumin (control, squares).

Peptides derived from natural casein enhance leukocyte and platelet reconstitution following syngeneic bone marrow transplantation in mice: When lethally irradiated (600 cGy), minimally bone marrow-reconstituted, BALB/c mice (n=12) received 1 mg per mouse peptides derived from natural casein via intravenous injection along with the bone marrow cells, significant increases in peripheral white blood cell counts on days 4, 6 and 15 post-treatment were noted, compared to controls receiving human serum albumin (FIG. 8). Platelet counts in the peripheral blood of both the treated and control irradiated, bone marrow transplanted mice were equally depressed up to 8 days post treatment. However, by the thirteenth day a clear advantage was noted for the mice treated with the peptides derived from natural casein, demonstrating a significant increase over the human serum albumin-treated controls which became even more pronounced by day 15 (FIG. 9). Thus, peptides derived from natural casein enhance platelet and leukocyte reconstitution following transplantation with limiting numbers of bone marrow cells. It is expected that this effect will be further increased in reconstitution with optimal, rather than limiting numbers of bone marrow cells.

Synthetic peptides derived from casein enhance leukocyte reconstitution following syngeneic bone marrow transplantation in mice: When lethally irradiated (600 cGy), minimally bone marrow-reconstituted, BALB/c mice (n=5 per synthetic peptide, n=10 in the control group) received 1 mg per mouse synthetic peptides (15-26 amino acids in length, see Table 3) derived from casein via an intraperitoneal injection along with the bone marrow cells, a clear enhancement of leukocyte reconstitution was observed. Significant increases in peripheral white blood cell counts over a 10 to 14 day period were noted with peptides having 13 (day 10: $17.2 \times 10^6$ cells per dl; day 12: $65.4 \times 10^6$ cells per dl) and 17 (day 10: $27.4$ cells$\times 10^6$ per dl; day 12: $52.0 \times 10^6$ cells per dl) amino acids (see Table 3), compared to controls receiving human serum albumin (day 10: $16.7 \times 10^6$ cells per dl; day 12: $46.4 \times 10^6$ cells per dl). Thus, synthetic peptides derived from casein enhance leukocyte reconstitution following transplantation with limiting numbers of bone marrow cells.

Synthetic peptides derived from casein enhance platelet reconstitution following syngeneic bone marrow transplantation in mice: In order to confirm the observed ability of synthetic peptides derived from casein to enhance megakaryocyte proliferation in hematopoietic stem cell cultures (see FIGS. 6 and 7), the peptides' effects on platelet reconstitution in vivo was investigated. When lethally irradiated (800 cGy), minimally bone marrow-reconstituted, mice (n=5 per group) received 100 µg per mouse synthetic peptides 4P and 3a (6 and 12 amino acids in length, respectively—see Table 3) in 4 daily intraperitoneal injections (4-7 days post-transplantation), a clear enhancement of platelet reconstitution over untreated controls was observed. Significant increases in platelet counts at 10 and 12 days post transplantation were noted for both peptides. Treatment with peptide 4P increased counts by 29% ($872 \times 10^3$/ml compared with $676 \times 10^3$/ml in the control group) at 12 days post transplantation while treatment with peptide 3a increased counts by up to 35.5% ($229 \times 10^3$/ml compared with $169 \times 10^3$/ml in the control group) at 10 days, and up to 13.5% ($622 \times 10^3$/ml compared with $461 \times 10^3$/ml in the control group) at 12 days post transplantation. Thus, the same synthetic peptides derived from casein enhance megakaryocyte proliferation in vitro and platelet reconstitution following bone marrow transplantation in vivo.

Figure 10A:
FIGS. 10a-f depict the penetration and nuclear uptake of FITC-conjugated peptides derived from natural casein in cultured human T-lymphocyte cells, as recorded by fluorescent microscopy. F1 and F2 are identical fractions of the FITC-conjugated peptides derived from natural casein. Sup-$T_1$ cells were incubated with 100 μg per ml FITC-conjugated peptides derived from natural casein as described in the Examples section that follows. At the indicated times, the cells were washed of free label, fixed in formalin and prepared for viewing and recording by Laser Scanning Confocal Microscopy.
Figure 10B:
Figure 10C:
Figure 10D:
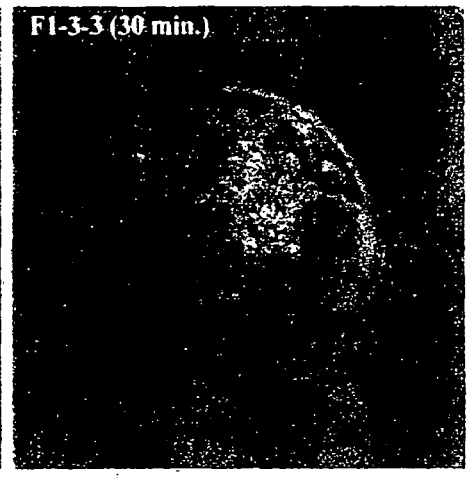
Figure 10E:
Figure 10F:
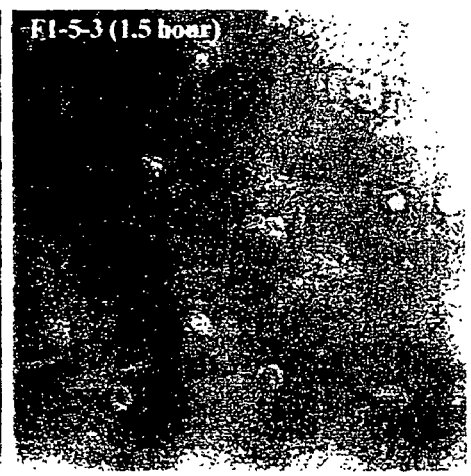

Peptides derived from natural casein inhibit in vitro infection of lymphocytic T cell lines by HIV-1 virus: In order to investigate the mechanisms of immune stimulatory and antiviral effects of peptides derived from natural casein, susceptible Sup-T1 and CEM cultured human T-cells were treated with peptides derived from natural casein prior to in vitro infection with HIV-1 virus. Fluorescent microscopy revealed that FITC-conjugated peptides derived from natural casein (100 µg per ml) penetrated the Sup-T1 cells when incubated therewith as described above (FIGS. 10a-f). A small amount of label was observed in the cytoplasm of the cells after 15 minutes (FIGS. 10a-b). At 30 minutes (FIGS. 10c-d) more label was observed in the cytoplasm, with limited nuclear uptake. From 1 hour incubation and on (FIGS. 10e-f), FITC-labeled peptides derived from natural casein were observed in the cytoplasm, but mostly they were concentrated in the cell nucleus. Analysis of the Sup-T1 cells by flow cytometry confirmed increasing uptake of the labeled peptides derived from natural casein from 5 minutes post incubation.

Peptides derived from natural casein enhance human lymphocyte proliferation: The presence of peptides derived from natural casein in the culture medium resulted in increased Sup-T$_1$ cell counts over a period of 14 days. The greatest increases in cell number at 7 days was observed for 50 µg per ml peptides derived from natural casein (42%), for 1000 µg at 10 days (30%) and for 600 µg (32%) at 14 days incubation (data not shown).

Measurement of [$^3$H]-thymidine incorporation by the cultured cells, providing a proliferation index, reflected the increase in cell number, with the most significant effect noted for 600 µg per ml peptides derived from natural casein on day 10 and 50 µg per ml on day 14 (FIG. 11). The reduced proliferation indices at 14 days probably reflect cell overgrowth and nutrient depletion.

Synthetic peptides derived from casein enhance human lymphocyte proliferation: The presence of synthetic peptides derived from casein (all peptides listed in Table 3) in the culture medium resulted in increased Sup-T1 cell counts over a period of 10 days. The increase was similar for all synthetic peptides. The greatest increases in lymphocyte cell number in infected cells were observed for 250 µg and 500 µg per ml of peptide representing the first 9 amino acids (80% and 33%, respectively) (data not shown).

Peptides derived from natural casein inhibit HIV-1 infection in human lymphocyte cells: Susceptible CEM lymphocyte cells pretreated with peptides derived from natural casein (50-1000 µg per ml) 3, 24 or 48 hours prior to incubation with HIV-1 exhibited enhanced cell proliferation and reduced levels of viral infection compared to untreated controls. Cell counts and HIV-1 P24 antigen assay at 15 days post infection revealed 100% inhibition of viral infection after 3 hours incubation with 600-1000 µg per ml peptides derived from natural casein and 98% and 99% inhibition after 24 hours incubation with 50 and 600 µg per ml peptides, respectively (comparing cell numbers with uninfected controls UIF). Longer incubation times were not found to be more effective (FIG. 12). Although increasing concentrations of peptides derived from natural casein enhanced cell proliferation at 3 and 24 hours post infection, viral infection is most significantly inhibited in these fastest growing cultures. An even more dramatic enhancement of cell proliferation and inhibition of HIV-1 infection was observed in Sup-T1 cells pretreated with peptides derived from natural casein before HIV-1 infection (average inhibition of viral infection of 96.7%, 88.7% and 95.7% for 3 hours, 24 hours and 48 hours pretreatment, respectively) (not shown). Thus, peptides derived from natural casein penetrate human cultured lymphocyte cells and their nuclei, enhance cell growth, and significantly reduce the susceptibility of $CD_{4+}$ cells to HIV-1 infection. As such, peptides derived from natural casein are expected to be useful both at preventing HIV infection and for post infection treatment of HIV infected and AIDS patients.

Synthetic peptides derived from casein inhibit HIV-1 infection in human lymphocyte cells: The ability of Synthetic peptides derived from casein to inhibit HIV-1 infection in human lymphocyte cells was demonstrated using CEM-lymphocyte cells under the same conditions outlined above. Three hours pretreatment of CEM lymphocytes with the synthetic peptide derived from casein representing the first 3 amino acids of oS1 casein conferred a significant degree of resistance to infection following incubation with HIV-1. Lymphocyte cell numbers were $1.29 \times 10^6$ (100 µg per ml) and $2.01 \times 10^6$ (500 µg per ml) in the treated cells as compared to the infected HIV-1 control of $1.06 \times 10^6$ (FIG. 13). HIV-1 infection levels in the same cells, measured by the HIV-P$^{24}$ antigen assay at 7 days post infection, was significantly reduced in the peptide treated cells (0.17 and 0.14 ng P24 Antigen/ml with 100 µg/ml and 500 µg/ml respectively), as compared to the untreated controls (0.52 ng P Ag/ml).

Likewise, significant inhibition of HIV-1 infection was observed in the CEM cells pre-treated (3 hours) with the synthetic casein derived peptide representing the first 5 amino acids of oS1 casein.

Cell counts in the cultures incubated with 10 and 25 µg peptide 3P per ml were $1.17 \times 10^6$ and $1.26 \times 10^6$ respectively, as compared to the infected HIV-1 control of $1.06 \times 10^6$.

HIV-P24 antigen assay at 7 days post infection, revealed significant reduction in HIV-1 infection levels in treated cultures (0.26 and 0.18 ng P24 Ag per ml for 10 and 25 µg per ml respectively, as compared to the control of 0.52 ng P24 Ag per ml).

Likewise, 3 hours preincubation with the synthetic peptide derived from casein4P, representing the first 6 amino acids of oS1 casein had a significant effect on the susceptibility of CEM lymphocyte cells to infection with HIV-1. Cell numbers were most affected at concentrations of 25 and 250 µg per ml ($1.26 \times 10^6$, and $1.59 \times 10^6$ respectively, as compared to the infected control value of $1.06 \times 10^6$).

Assay of HIV-P$^{24}$ antigen at 7 days post infection, revealed a dose dependent reduction in viral particles as compared to the untreated, infected control cultures (FIG. 13). Thus, the protection from HIV-1 infection afforded lymphocyte cells by the peptides derived from natural casein is retained in Synthetic peptides derived from casein representing as few as the first five N-terminal amino acids of αS-1 casein.

Figure 14:
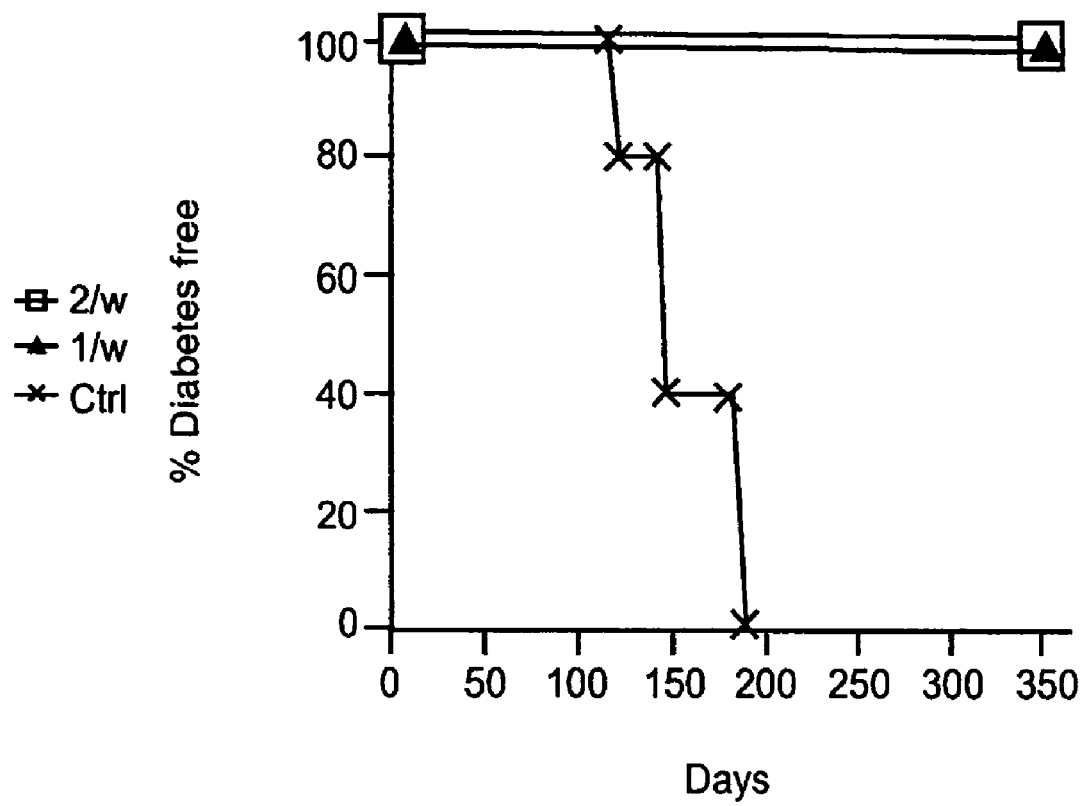
FIG. 14 depicts the prevention by peptides derived from natural casein of Juvenile (Type I, IDDM) Diabetes in female Non Obese Diabetic mice. Glucosuria was monitored at intervals during 365 days post treatment in female NOD mice receiving a once (triangles) or twice (squares) weekly injection of 100 μg peptides derived from natural casein for 5 weeks (6 or 11 injections total) and untreated controls. All the controls developed glucosuria and subsequently died.

Peptides derived from natural casein prevent development of glucosuria in Non-Obese Diabetic (NOD) mice: Non-Obese Diabetic (NOD) mice spontaneously develop Juvenile (Type I, IDDM) Diabetes, an autoimmune condition causing inflammation of the pancreatic P cells and ending in disease and death. Female NOD mice are extremely susceptible, demonstrating evidence of macrophage invasion of the pancreatic islet interstitial matrix as early as 5 weeks old. A once or twice weekly injection of 100 µg peptides derived from natural casein for 5 weeks (6 or 11 injections total) were completely effective in preventing the glucosuria associated with the onset and course of the disease. By 200 days 100% of the untreated control mice (n=5) had become diabetic, and subsequently died, while the treated mice (n=5) remained 100% euglycemic, all still surviving at 365 days (FIG. 14). Thus, peptides derived from natural casein effectively protected genetically susceptible mice against the onset of this autoimmune inflammatory condition.

Synthetic Peptides Derived from Casein Prevent Development of Glucosuria in Non-Obese Diabetic (NOD) Mice:

The preventative effect of Synthetic peptides derived from casein on the development of glucosuria in NOD mice was demonstrated under the same conditions outlined above, except that the mice were injected only once weekly for five (5) weeks with 100 μg of Synthetic peptides derived from casein. The results of these experiments are presented in Table 4 below:

TABLE 4

The effect of synthetic peptides on IDDM in NOD mice

| Peptide Derivative code | Healthy/Total* | Urine Sugar | IPGT TEST 0 min. (pre-load) | 60 min. post load |
|---|---|---|---|---|
| Y | 1/5 | Negative | 121 | 138 |
| X | 3/5 | Negative | 94 | 114 |
|  |  | Negative | 104 | 119 |
|  |  | Negative | 141 | 114 |
| 1a | 1/5 | Negative | 88 | 106 |
| 2a | 4/5 | Negative | 215 | 183 |
|  |  | Negative | 112 | 119 |
|  |  | Negative | 95 | 107 |
|  |  | Negative | 159 | 204 |
| 3a | 3/5 | Negative | 135 | 137 |
|  |  | Negative | 205 | 197 |
|  |  | Negative | 201 | 211 |
| A | 2/5 | Negative | 134 | 164 |
|  |  | Negative | 105 | 107 |
| B | 2/5 | Negative | 130 | 117 |
|  |  | Negative | 130 | 97 |
| D | 2/5 | Negative | 99 | 108 |
|  |  | Negative | 130 | 136 |
| I | 2/5 | Negative | 324 | not tested |
|  |  | Negative | 124 | 138 |
| J | 3/5 | Negative | 166 | not tested |
|  |  | Negative | 193 | not tested |
|  |  | Negative | 186 | not tested |
| K | 2/5 | Negative | 116 | 143 |
|  |  | Negative | 443 | not tested |
| Chay-13 | 2/5 | Negative | 123 | 130 |
|  |  | Negative | 111 | 111 |
| Chay-13 | 2/5 | Negative | 128 | 116 |
|  |  | Negative | 113 | 125 |
| Control | 0/5 |  |  |  |

Blood was drawn from the paraorbital plexus at 0 min and 60 min after the intraperitoneal injection of glucose 1 g/kg body weight.
Plasma glucose levels were determined with a Glucose Analyzer 2 (Beckman Instruments, Fullerton, CA) and expressed as mmol/L.
*Healthy and well = Sugar not detected in urine.
Glucosuria = >1000 mg/dL.
IPGTT performed with 6 healthy female control mice: 0 min - 110 mmol/L; 60 min - 106 mmol/L blood glucose.

The synthetic peptides derived from casein representing the first 9 (X), 11 (2a) and 12 (3a) amino acids and higher chain length of αS1 casein, were highly effective in preventing the glucosuria associated with the onset and course of the disease.

Effect of treatment with synthetic peptides derived from casein was evaluated after 25 weeks. At that time, all 5 mice in the untreated control group (n=5) had become diabetic, as indicated by the presence of frank (>1000 mg/dl) glucosuria (Table 4).

No glucosuria was detected in three of the five (3/5) NOD mice treated with the synthetic peptide representing the first nine (9) amino acids from the N terminal of αS1 casein. Of the group injected with the synthetic peptide of eleven (11) amino acids from the N terminal of αS1 casein, no glucosuria was detected in four out of five (4/5) of the NOD mice In the groups of peptide treated mice in which glucosuria was detected, the onset was generally significantly delayed (by 3-5 weeks) relative to the onset of glucosuria in untreated controls (data not shown), indicating a clearly protective effect of the peptides even when incomplete.

The protective effects of shorter Synthetic peptides derived from casein have also been studied in NOD mice. In an additional series of experiments similar to the abovementioned, administration of peptides representing the first 3 (1P) and 4 (2P) N-terminal amino acids of αS1 casein effectively prevented the onset of glucosuria in the treated mice (assayed at week 16), while the untreated controls had all become diabetic (100% glucosuria) (data not shown).

The glucose tolerance (IPGT) test performed after 25 weeks with the healthy and well NOD mice, of the group injected with the synthetic casein derived peptide of the first 9 amino acids, showed no evidence of abnormal glucose metabolism (normal glycemic values pre- and 60 minutes post-glucose loading).

In the group treated with the synthetic peptide derived from casein representing the first 11 amino acids of the N-terminal of αS1 casein (2a), resting plasma glucose levels were somewhat elevated in two of the five mice (215 and 159 mmol/L), and remained mildly elevated at (183 and 204 mmol/L) 60 minutes post load, indicating mild diabetic tendencies. The other two mice remained within normal glycemic range throughout the test (Table 4). In general, the normal results of the IPGTT reflected the absence of glucosuria in the healthy, surviving peptide-treated mice (Table 4). Thus, synthetic peptides representing only a few amino acids from the N-terminal of αS1 casein, as well as peptides derived from native casein dramatically reduce the susceptibility of genetically predisposed NOD mice to onset of autoimmune diabetic disease.

Synthetic casein-derived peptides significantly reduce Total Cholesterol blood levels (TC), Low Density Lipoprotein (LDL) and High Density Lipoprotein (HDL): Intraperitoneal administration of Synthetic peptides derived from casein caused a significant reduction in the blood lipid (HDL, LDL and TC) values in experimentally hypercholesterolemic mice. After one week of the atherogenic Thomas Hartroft diet, the blood cholesterol levels of the mice had risen to the levels of 318 mg/dl.

One week post treatment with 1 mg synthetic peptides derived from casein per mouse, the group treated with the Synthetic peptides derived from casein representing the first 5 (3P) and 11 (2a) amino acids of αS1 casein, had significantly reduced TC, HDL and LDL values, compared to those of the control group [TC: 308 and 279 mg/dl respectively; HDL: 41 mg/dl and 40 mg/dl respectively and LDL: 247 mg/dl and 221 mg/dl respectively as compared to 393 mg/dl (TC), 52 mg/dl (HDL) and 326 mg/dl (LDL) in the diet-induced hypercholesterol-/hyperlipidemic control group] (FIG. 15). Thus, synthetic peptides representing the first few N-terminal amino acids of αS 1 casein effectively reduced experimentally induced hyperlipidemia and hypercholesterolemia within 1 week after a single, intraperitoneal administration.

Clinical Trials with Peptides Derived from Natural Casein:

Patients received intramuscular injections of 50 mg peptides derived from natural casein each, in one or three depots, as indicated.

Peptides derived from natural casein stimulates hematopoiesis in cancer patients: The hematology profiles of six cancer patients who had received or were receiving chemotherapy were examined before and following administration of peptides derived from natural casein, as indicated. Special attention was paid to changes in the Platelet (PLT), Leukocyte (WBC), Erythrocyte (RBC) and Hemoglobin (HGB) values, representing thrombocytopoiesis, leukocytopoiesis, and erythrocytopoiesis, respectively.

G.T., (Female patient, Patient 1): Patient had ovarian cancer, undergone a hysterectomy followed by chemotherapy. She received two intramuscular injections of peptides derived from natural casein at two and then two and one half months post operation. No chemotherapy was administered between the first and second administrations of peptides derived from natural casein. Blood tests from 6 days post first injection, 7, and 13 days post second injection reflect a considerable increase in platelet and WBC components, as well as increased RBC (FIG. 16).

E.C., (Female patient, Patient 2): Patient underwent a radical mastectomy for lobular carcinoma in 1983, and six years later suffered from gastric metastases. Three days prior to commencement of chemotherapy, she received one intramuscular peptides derived from natural casein by injection, and a second 10 days after the chemotherapy. Although the blood counts from 10 and 16 days post chemotherapy indicated an attenuation of the is depressed hematological profile usually encountered following chemotherapy, the most significant effects of peptides derived from natural casein were noted 3 days after the first injection, prior to the chemotherapy (FIG. 16).

E.S., (Female patient, Patient 3): Patient was suffering from widespread metastatic dissemination of a breast carcinoma first discovered in 1987. Two years later, she received a first intramuscular injection of peptides derived from natural casein, and a second 23 days later. No additional therapy was administered during this period. Blood tests indicate a strong enhancement of PLT seven days after the first treatment and a significant increase in RBC and WBC seven days after the second treatment (FIG. 16).

J.R., (Female patient, Patient 4): Patient's diagnosis is breast cancer with bone metastases. She received one intramuscular injection of peptides derived from natural casein 8 days before commencing chemotherapy, and another, 14 days later. The most significant effect is clearly seen in the rapid return of WBC levels following chemotherapy-induced depression (FIG. 16).

D.M., (Female patient, Patient 5): Patient suffering from hepatic cancer with widespread metastatic dissemination. She received three intramuscular injections of peptides derived from natural casein at 10, 8 and 6 days before receiving chemotherapy. A second series of injections was initiated 10, 12 and 14 days following the chemotherapy treatment. Although a significant effect on the hematological profile is noted following the first series of injections and prior to the chemotherapy, the most dramatic improvements are seen in the rapid return of depressed post-chemotherapy values to normalized cell counts following the second series of peptides derived from natural casein injections (FIG. 16).

Thus, administration of peptides derived from natural casein to cancer patients results in improved hematological profiles, specifically enhanced erythropoiesis, leukocytopoiesis and thrombocytopoiesis, and is capable of moderating and shortening the duration of chemotherapy-induced depression of blood components.

Peptides derived from natural casein stimulates thrombocytopoiesis in transplant recipients with resistant thrombocytopenia: Prolonged transfusion-resistant thrombocytopenia with episodes of severe bleeding, may be a life threatening complication of bone marrow transfusion, especially where traditional therapies are ineffective. Two patients with severe resistant thrombocytopenia were treated with peptides derived from natural casein.

Figure 17:
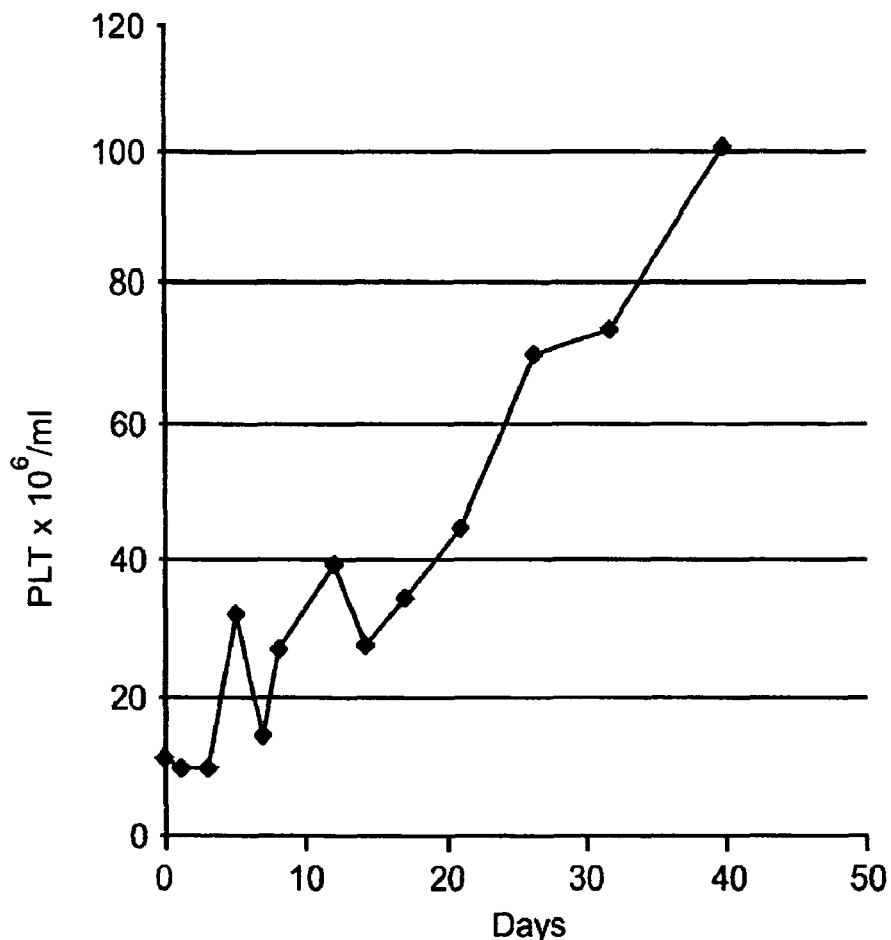
FIG. 17 depicts the stimulation by peptides derived from natural casein of thrombocytopoiesis in a platelet-resistant patient with Acute Myeloid Leukemia (M-1). Thrombocyte reconstitution was expressed as the change in platelet content of peripheral blood (PLA, ×$10^6$ per ml), counted as described above at the indicated intervals following intramuscular injection (as described in the Examples section that follows) of 100 μg peptides derived from natural casein.

M-1 (Female patient): 32 year old patient suffering from Acute Myeloid Leukemia in complete remission, following autologous stem cell transfusion. She had experienced two life-threatening bleeding episodes, involving pulmonary hemorrhage and a large obstructive hematoma in the soft palate. At more than 114 days post transfusion, platelet counts were refractive to rhIL-3, rhIL-6, intravenous gamma globulin, and recombinant erythropoietin. Following a single intra muscular treatment with 50 mg peptides derived from natural casein, divided into three depots, her condition improved immediately. Along with the rapid return of normal platelet counts (FIG. 17), her distal limb bleeding with exertion and patechyae subsided, she was able to resume walking, and returned to her home overseas with no complications or side effects.

Figure 18:
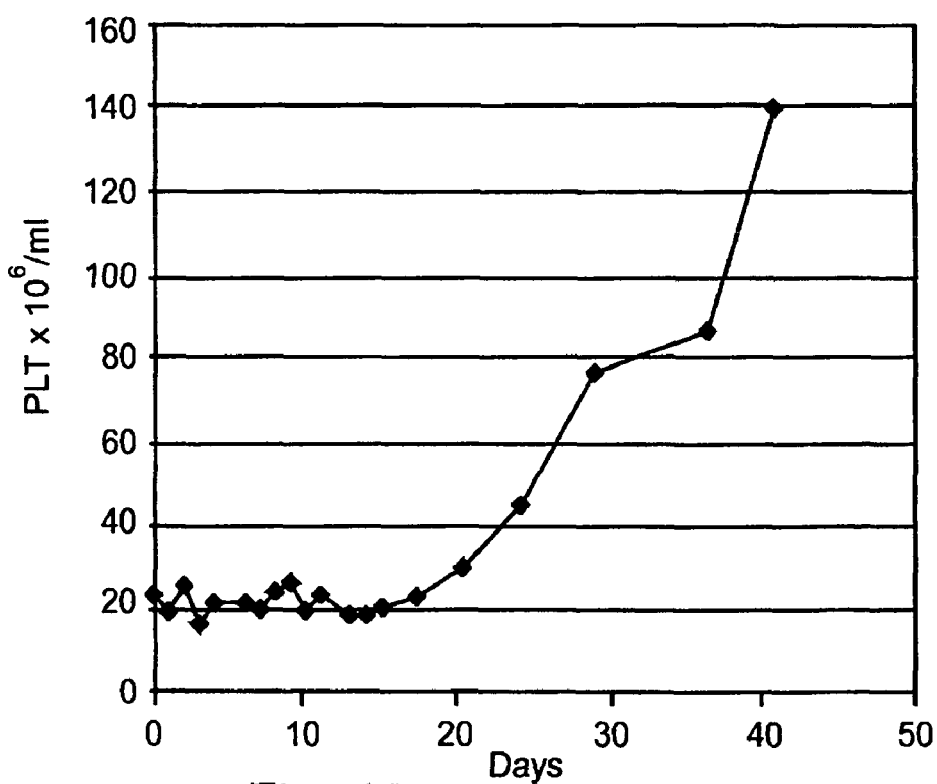
FIG. 18 depicts the stimulation by peptides derived from natural casein of thrombocytopoiesis in a platelet-resistant patient with Acute Myeloid Leukemia (M-2). Thrombocyte reconstitution was expressed as the change in platelet content of peripheral blood (PLA, ×10 per ml), counted as described above at the indicated intervals following intramuscular injection (as described in the Examples section that follows) of 100 μg peptides derived from natural casein.

M-2 (Male patient): 30 year old patient suffering from Acute Myeloid Leukemia in a second complete remission following autologous stem cell transfusion, exhibiting totally resistant platelet counts and massive gastrointestinal bleeding episodes. He required daily transfusions of packed cells, had developed hypoalbuminia, and failed to respond to extensive therapy with rhIL-3, rhIL-6 and gamma globulin. Following one intramuscular administration of 50 mg peptides derived from natural casein in three depots 86 days post transfusion, rapid platelet reconstitution (FIG. 18) and gradual discontinuation of the bleeding was observed. No further treatment was required, and the patient is presently completely asymptomatic with normal platelet count.

Thus, one course of intramuscular administration of peptides derived from natural casein at 1 mg per kg body weight, divided into three depots was effective in rapidly reconstituting platelet counts and diminishing associated clinical symptoms in patients suffering from prolonged, transfusion resistant thrombocytopenia with life-threatening bleeding episodes.

Peptides Derived from Natural Casein Decreases Triglycerides and LDL-cholesterol in Familial Hyperlipidemia:

M.S. (Female patient): Patient is a 38 year old female with family history of hyperlipidemia. Before treatment with peptides derived from natural casein, blood chemistry profile revealed elevated total cholesterol (321 mg per dl), triglycerides (213 mg per dl; normal range 45-185 mg per dl) and elevated LDL-cholesterol (236.4 mg per dl; normal range 75-174 mg per dl). One month after administration of 50 mg peptides derived from natural casein in three intra muscular depots the hyperlipidemia was stabilized: total cholesterol was reduced to 270 mg per dl, triglycerides were 165 mg per dl and LDL-cholesterol was 201 mg per dl, still higher than normal range but significantly reduced from the pretreatment value. No additional treatment was administered. Thus, treatment with peptides derived from natural casein is effective in rapidly bringing about a significant reduction in otherwise untreated hyperlipidemia in humans.

Peptides Derived from Natural Casein Stimulate Normoglobinemia in a Case of Occult Bleeding:

D. G. (Male patient): Patient is a 75 year old male suffering from anemia and hypoglobinemia (depressed RBC, HGB, HCT, MCH and MCHC) associated with extensive occult bleeding. One month after receiving one intramuscular injection of 50 mg peptides derived from natural casein in three depots, a significant reduction of the anemia was observed. After two months, RBC approached normal values (4.32 instead of 3.44 M per μl), HGB increased (11.3 instead of 8.9 g per dl) and HCT, MCH and MCHC all improved to nearly normal values, despite the persistence of occult bleeding. Thus, one injection of peptides derived from natural casein seemed capable of stimulating erythropoiesis and reducing anemia associated with blood loss in humans.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences identified by an accession number, mentioned in this specification are herein incorporated in their entirety by reference into the specification, to the same extent as if each individual publication, patent, patent application or sequence was specifically and individually indicated to be incorporated herein by reference. In addition, citation or identification of any reference in this application shall not be construed as an admission that such reference is available as prior art to the present invention.

What is claimed is:

1. A method for inducing or increasing hematopoiesis in a subject, comprising administering to a subject in need thereof a therapeutically effective amount of a casein peptide, wherein said casein peptide consists of an amino acid sequence selected from the group consisting of SEQ ID NOs: 2-21 and 23-25.

2. The method of claim 1, wherein administering said casein peptide increases or induces at least one of hematopoietic stem cell proliferation; hematopoietic stem cell differentiation; megakaryocytopoiesis; leukocytopoiesis, erythrotopoiesis and thrombopoiesis.

3. The method of claim 2, wherein administering said casein peptide increases or induces thrombopoiesis for treating thrombocytopenia.

4. The method of claim 1, wherein said casein peptide is administered for treating a disorder selected from the group consisting of pancytopenia, granulocytopenia, helper T-cell disorders, dendritic cell deficiencies, macrophage deficiencies, hematopoietic stem cell disorders, pre-leukemic conditions, leukemic conditions and a blood cell disorder resulting from chemotherapy or radiation therapy.

5. The method of treatment of claim 4, wherein said hematopoietic stem cell disorders are selected from the group consisting of platelet, lymphocyte, plasma cell and neutrophil disorders.

6. The method of claim 1, wherein said peptide consists of the amino acid of SEQ ID NO: 2.

7. The method of claim 1, wherein said peptide consists of the amino acid of SEQ ID NO:3.

8. The method of claim 1, wherein said peptide consists of the amino acid of SEQ ID NO:4.

9. The method of claim 1, wherein said peptide consists of the amino acid of SEQ ID NO:5.

10. The method of claim 1, wherein said peptide consists of the amino acid of SEQ ID NO:6.

11. The method of claim 1, wherein said peptide consists of the amino acid of SEQ ID NO:7.

12. The method of claim 1, wherein said peptide consists of the amino acid of SEQ ID NO:8.

13. The method of claim 1, wherein said peptide consists of the amino acid of SEQ ID NO:9.

14. The method of claim 1, wherein said peptide consists of the amino acid of SEQ ID NO:10.

15. The method of claim 1, wherein said peptide consists of the amino acid of SEQ ID NO:11.

16. The method of claim 1, wherein said peptide consists of the amino acid of SEQ ID NO:12.

17. The method of claim 1, wherein said peptide consists of the amino acid of SEQ ID NO:13.

18. The method of claim 1, wherein said peptide consists of the amino acid of SEQ ID NO:14.

19. The method of claim 1, wherein said peptide consists of the amino acid of SEQ ID NO:15.

20. The method of claim 1, wherein said peptide consists of the amino acid of SEQ ID NO:16.

21. The method of claim 1, wherein said peptide consists of the amino acid of SEQ ID NO:17.

22. The method of claim 1, wherein said peptide consists of the amino acid of SEQ ID NO:18.

23. The method of claim 1, wherein said peptide consists of the amino acid of SEQ ID NO:19.

24. The method of claim 1, wherein said peptide consists of the amino acid of SEQ ID NO:20.

25. The method of claim 1, wherein said peptide consists of the amino acid of SEQ ID NO:21.

26. The method of claim 1, wherein said peptide consists of the amino acid of SEQ ID NO:23.

27. The method of claim 1, wherein said peptide consists of the amino acid of SEQ ID NO:24.

28. The method of claim 1, wherein said peptide consists of the amino acid of SEQ ID NO:25.

29. A method of treating a disease selected from the group consisting of glucosuria, hyperglycemia and diabetes, comprising administering to a subject in need thereof a therapeutically effective amount of a peptide consisting of the amino acid sequence selected from the group consisting of SEQ ID NOs: 2-21 and 23-25.

30. The method of claim 29, wherein said peptide consists of the amino acid of SEQ ID NO: 2.

31. The method of claim 29, wherein said peptide consists of the amino acid of SEQ ID NO:3.

32. The method of claim 29, wherein said peptide consists of the amino acid of SEQ ID NO:4.

33. The method of claim 29, wherein said peptide consists of the amino acid of SEQ ID NO:5.

34. The method of claim 29, wherein said peptide consists of the amino acid of SEQ ID NO:6.

35. The method of claim 29, wherein said peptide consists of the amino acid of SEQ ID NO:7.

36. The method of claim 29, wherein said peptide consists of the amino acid of SEQ ID NO:8.

37. The method of claim 29, wherein said peptide consists of the amino acid of SEQ ID NO:9.

38. The method of claim 29, wherein said peptide consists of the amino acid of SEQ ID NO:10.

39. The method of claim 29, wherein said peptide consists of the amino acid of SEQ ID NO:11.

40. The method of claim 29, wherein said peptide consists of the amino acid of SEQ ID NO:12.

41. The method of claim 29, wherein said peptide consists of the amino acid of SEQ ID NO:13.

42. The method of claim 29, wherein said peptide consists of the amino acid of SEQ ID NO:14.

43. The method of claim 29, wherein said peptide consists of the amino acid of SEQ ID NO:15.

44. The method of claim 29, wherein said peptide consists of the amino acid of SEQ ID NO:16.

45. The method of claim 29, wherein said peptide consists of the amino acid of SEQ ID NO:17.

46. The method of claim 29, wherein said peptide consists of the amino acid of SEQ ID NO:18.

47. The method of claim 29, wherein said peptide consists of the amino acid of SEQ ID NO:19.

48. The method of claim 29, wherein said peptide consists of the amino acid of SEQ ID NO:20.

49. The method of claim 29, wherein said peptide consists of the amino acid of SEQ ID NO:21.

50. The method of claim 29, wherein said peptide consists of the amino acid of SEQ ID NO:23.

51. The method of claim 29, wherein said peptide consists of the amino acid of SEQ ID NO:24.

52. The method of claim 29, wherein said peptide consists of the amino acid of SEQ ID NO:25.

53. A method for inducing or increasing hematopoiesis in a subject, comprising administering to a subject in need thereof a therapeutically effective amount of a pharmaceutical composition comprising a casein peptide, wherein the casein peptide in said composition consists of the amino acid sequence selected from the group consisting of SEQ ID NOs: 2-21 and 23-25.

54. A method for inducing or increasing hematopoiesis in a subject, comprising administering to a subject in need thereof a therapeutically effective amount of a peptide consisting of the amino acid sequence selected from the group consisting of SEQ ID NOs: 2-21, 23, 24, and 25.

55. A method of treating a disease selected from the group consisting of glucosuria, hyperglycemia and diabetes, comprising administering to a subject in need thereof a therapeutically effective amount of a pharmaceutical composition comprising a casein peptide, wherein the casein peptide in said composition consists of the amino acid sequence selected from the group consisting of SEQ ID NOs: 2-21 and 23-25.

56. A method of treating a disease selected from the group consisting of glucosuria, hyperglycemia and diabetes, comprising administering to a subject in need thereof a therapeutically effective amount of a peptide consisting of the amino acid sequence selected from the group consisting of SEQ ID NOs: 2-21, 23, 24 and 25.

* * * * *

```
                       SEQUENCE LISTING

<160> NUMBER OF SEQ ID NOS: 25

<210> SEQ ID NO 1
<211> LENGTH: 2
<212> TYPE: PRT
<213> ORGANISM: Artificial sequence
<220> FEATURE:
<223> OTHER INFORMATION: Synthetic peptide

<400> SEQUENCE: 1

Arg Pro
1

<210> SEQ ID NO 2
<211> LENGTH: 3
<212> TYPE: PRT
<213> ORGANISM: Artificial sequence
<220> FEATURE:
<223> OTHER INFORMATION: Synthetic peptide

<400> SEQUENCE: 2

Arg Pro Lys
1

<210> SEQ ID NO 3
<211> LENGTH: 4
<212> TYPE: PRT
<213> ORGANISM: Artificial sequence
<220> FEATURE:
<223> OTHER INFORMATION: Synthetic peptide

<400> SEQUENCE: 3

Arg Pro Lys His
1

<210> SEQ ID NO 4
<211> LENGTH: 5
<212> TYPE: PRT
<213> ORGANISM: Artificial sequence
<220> FEATURE:
<223> OTHER INFORMATION: Synthetic peptide

<400> SEQUENCE: 4

Arg Pro Lys His Pro
1               5

<210> SEQ ID NO 5
<211> LENGTH: 6
<212> TYPE: PRT
<213> ORGANISM: Artificial sequence
<220> FEATURE:
<223> OTHER INFORMATION: Synthetic peptide

<400> SEQUENCE: 5
```

```
Arg Pro Lys His Pro Ile
1               5

<210> SEQ ID NO 6
<211> LENGTH: 7
<212> TYPE: PRT
<213> ORGANISM: Artificial sequence
<220> FEATURE:
<223> OTHER INFORMATION: Synthetic peptide

<400> SEQUENCE: 6

Arg Pro Lys His Pro Ile Lys
1               5

<210> SEQ ID NO 7
<211> LENGTH: 8
<212> TYPE: PRT
<213> ORGANISM: Artificial sequence
<220> FEATURE:
<223> OTHER INFORMATION: Synthetic peptide

<400> SEQUENCE: 7

Arg Pro Lys His Pro Ile Lys His
1               5

<210> SEQ ID NO 8
<211> LENGTH: 9
<212> TYPE: PRT
<213> ORGANISM: Artificial sequence
<220> FEATURE:
<223> OTHER INFORMATION: Synthetic peptide

<400> SEQUENCE: 8

Arg Pro Lys His Pro Ile Lys His Gln
1               5

<210> SEQ ID NO 9
<211> LENGTH: 10
<212> TYPE: PRT
<213> ORGANISM: Artificial sequence
<220> FEATURE:
<223> OTHER INFORMATION: Synthetic peptide

<400> SEQUENCE: 9

Arg Pro Lys His Pro Ile Lys His Gln Gly
1               5                   10

<210> SEQ ID NO 10
<211> LENGTH: 11
<212> TYPE: PRT
<213> ORGANISM: Artificial sequence
<220> FEATURE:
<223> OTHER INFORMATION: Synthetic peptide

<400> SEQUENCE: 10

Arg Pro Lys His Pro Ile Lys His Gln Gly Leu
1               5                   10

<210> SEQ ID NO 11
<211> LENGTH: 12
<212> TYPE: PRT
<213> ORGANISM: Artificial sequence
<220> FEATURE:
<223> OTHER INFORMATION: Synthetic peptide

<400> SEQUENCE: 11
```

```
Arg Pro Lys His Pro Ile Lys His Gln Gly Leu Pro
1               5                   10
```

<210> SEQ ID NO 12
<211> LENGTH: 13
<212> TYPE: PRT
<213> ORGANISM: Artificial sequence
<220> FEATURE:
<223> OTHER INFORMATION: Synthetic peptide

<400> SEQUENCE: 12

```
Arg Pro Lys His Pro Ile Lys His Gln Gly Leu Pro Gln
1               5                   10
```

<210> SEQ ID NO 13
<211> LENGTH: 14
<212> TYPE: PRT
<213> ORGANISM: Artificial sequence
<220> FEATURE:
<223> OTHER INFORMATION: Synthetic peptide

<400> SEQUENCE: 13

```
Arg Pro Lys His Pro Ile Lys His Gln Gly Leu Pro Gln Glu
1               5                   10
```

<210> SEQ ID NO 14
<211> LENGTH: 15
<212> TYPE: PRT
<213> ORGANISM: Artificial sequence
<220> FEATURE:
<223> OTHER INFORMATION: Synthetic peptide

<400> SEQUENCE: 14

```
Arg Pro Lys His Pro Ile Lys His Gln Gly Leu Pro Gln Glu Val
1               5                   10                  15
```

<210> SEQ ID NO 15
<211> LENGTH: 16
<212> TYPE: PRT
<213> ORGANISM: Artificial sequence
<220> FEATURE:
<223> OTHER INFORMATION: Synthetic peptide

<400> SEQUENCE: 15

```
Arg Pro Lys His Pro Ile Lys His Gln Gly Leu Pro Gln Glu Val Leu
1               5                   10                  15
```

<210> SEQ ID NO 16
<211> LENGTH: 17
<212> TYPE: PRT
<213> ORGANISM: Artificial sequence
<220> FEATURE:
<223> OTHER INFORMATION: Synthetic peptide

<400> SEQUENCE: 16

```
Arg Pro Lys His Pro Ile Lys His Gln Gly Leu Pro Gln Glu Val Leu
1               5                   10                  15

Asn
```

<210> SEQ ID NO 17
<211> LENGTH: 18
<212> TYPE: PRT
<213> ORGANISM: Artificial sequence
<220> FEATURE:
<223> OTHER INFORMATION: Synthetic peptide

<400> SEQUENCE: 17

Arg Pro Lys His Pro Ile Lys His Gln Gly Leu Pro Gln Glu Val Leu
1               5                   10                  15

Asn Glu

<210> SEQ ID NO 18
<211> LENGTH: 19
<212> TYPE: PRT
<213> ORGANISM: Artificial sequence
<220> FEATURE:
<223> OTHER INFORMATION: Synthetic peptide

<400> SEQUENCE: 18

Arg Pro Lys His Pro Ile Lys His Gln Gly Leu Pro Gln Glu Val Leu
1               5                   10                  15

Asn Glu Asn

<210> SEQ ID NO 19
<211> LENGTH: 20
<212> TYPE: PRT
<213> ORGANISM: Artificial sequence
<220> FEATURE:
<223> OTHER INFORMATION: Synthetic peptide

<400> SEQUENCE: 19

Arg Pro Lys His Pro Ile Lys His Gln Gly Leu Pro Gln Glu Val Leu
1               5                   10                  15

Asn Glu Asn Leu
            20

<210> SEQ ID NO 20
<211> LENGTH: 21
<212> TYPE: PRT
<213> ORGANISM: Artificial sequence
<220> FEATURE:
<223> OTHER INFORMATION: Synthetic peptide

<400> SEQUENCE: 20

Arg Pro Lys His Pro Ile Lys His Gln Gly Leu Pro Gln Glu Val Leu
1               5                   10                  15

Asn Glu Asn Leu Leu
            20

<210> SEQ ID NO 21
<211> LENGTH: 22
<212> TYPE: PRT
<213> ORGANISM: Artificial sequence
<220> FEATURE:
<223> OTHER INFORMATION: Synthetic peptide

<400> SEQUENCE: 21

Arg Pro Lys His Pro Ile Lys His Gln Gly Leu Pro Gln Glu Val Leu
1               5                   10                  15

Asn Glu Asn Leu Leu Arg
            20

<210> SEQ ID NO 22
<211> LENGTH: 23
<212> TYPE: PRT
<213> ORGANISM: Artificial sequence
<220> FEATURE:
<223> OTHER INFORMATION: Synthetic peptide

<400> SEQUENCE: 22

```
Arg Pro Lys His Pro Ile Lys His Gln Gly Leu Pro Gln Glu Val Leu
1               5                   10                  15

Asn Glu Asn Leu Leu Arg Phe
            20

<210> SEQ ID NO 23
<211> LENGTH: 24
<212> TYPE: PRT
<213> ORGANISM: Artificial sequence
<220> FEATURE:
<223> OTHER INFORMATION: Synthetic peptide

<400> SEQUENCE: 23

Arg Pro Lys His Pro Ile Lys His Gln Gly Leu Pro Gln Glu Val Leu
1               5                   10                  15

Asn Glu Asn Leu Leu Arg Phe Phe
            20

<210> SEQ ID NO 24
<211> LENGTH: 25
<212> TYPE: PRT
<213> ORGANISM: Artificial sequence
<220> FEATURE:
<223> OTHER INFORMATION: Synthetic peptide

<400> SEQUENCE: 24

Arg Pro Lys His Pro Ile Lys His Gln Gly Leu Pro Gln Glu Val Leu
1               5                   10                  15

Asn Glu Asn Leu Leu Arg Phe Phe Val
            20                  25

<210> SEQ ID NO 25
<211> LENGTH: 26
<212> TYPE: PRT
<213> ORGANISM: Artificial sequence
<220> FEATURE:
<223> OTHER INFORMATION: Synthetic peptide

<400> SEQUENCE: 25

Arg Pro Lys His Pro Ile Lys His Gln Gly Leu Pro Gln Glu Val Leu
1               5                   10                  15

Asn Glu Asn Leu Leu Arg Phe Phe Val Ala
            20                  25
```